(12) United States Patent
Pollock et al.

(10) Patent No.: US 7,176,179 B1
(45) Date of Patent: Feb. 13, 2007

(54) SELECTIVE INDUCTION OF CELL DEATH BY DELIVERY OF AMINO-TERMINAL INTERLEUKIN-1-α PRO-PIECE POLYPEPTIDE

(75) Inventors: Allan S. Pollock, San Francisco, CA (US); David H. Lovett, Lagunitas, CA (US); Johanna Turck, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/569,698

(22) Filed: May 11, 2000

Related U.S. Application Data

(63) Continuation-in-part of application No. 09/085,305, filed on May 27, 1998, now Pat. No. 6,191,269.

(60) Provisional application No. 60/048,137, filed on May 30, 1997.

(51) Int. Cl.
*A01N 37/18* (2006.01)
*A61K 38/00* (2006.01)

(52) U.S. Cl. .......................................... 514/2; 530/300
(58) Field of Classification Search ................ 530/350; 514/2
See application file for complete search history.

(56) References Cited

U.S. PATENT DOCUMENTS

| | | | | |
|---|---|---|---|---|
| 4,770,781 A | 9/1988 | Schmidt et al. | ............. | 210/635 |
| 4,801,686 A | 1/1989 | Kronheim | .................... | 530/351 |
| 4,894,333 A | 1/1990 | Cerretti et al. | ........... | 435/69.52 |
| 5,017,692 A | 5/1991 | Zurwarski et al. | .......... | 530/351 |
| 5,266,311 A | 11/1993 | Cerretti et al. | ............. | 424/85.2 |
| 5,494,663 A * | 2/1996 | Yamada et al. | ............. | 424/85.2 |
| 5,702,698 A | 12/1997 | Nakai et al. | ................ | 424/85.2 |

FOREIGN PATENT DOCUMENTS

| | | | |
|---|---|---|---|
| EP | 0 188 920 | | 7/1986 |
| EP | 188920 A | * | 7/1986 |
| EP | 0 200 986 | | 11/1986 |
| EP | 0 324 447 | | 7/1989 |
| EP | 32447 A | * | 7/1989 |
| EP | 0 327 360 A2 | | 8/1989 |

OTHER PUBLICATIONS

Lomedico PT.*
Wessendorf et al (J. Biol. Chem. 1993;268(29):22100-22104).*
Chaplin, et al. "Expression of Membrane-Associated Murine Interleukin-1 (IL-1) by Fibroblasts Transfected with Pro-IL-1α cDNA," *FASEB* 2(5):Abstract 5517 (May 1-5, 1988).
Higgins, et al., "Synthesis and Biological Activity of Human IL-1β Propiece In Vitro," *Arthritis and Rheumatism*, 36(9):Abstract B71 (Sep. 1993).
Stevenson, et al., "The N-Terminal 16kDA Propiece of the Interleukin-1α Precursor Persists Intracellularly and is Myristylated on Internal Lysine Residues," *Clinical Research*, 40(2):Abstract p. 186A (May 1992).
Turck, et al., "The N-Terminal Propiece of Interleukin-1α is a Pro-Apoptotic Factor," *JASN*, 6(3):Abstract 2052 (Sep. 1995).
Auron, et al., "Studies on the Molecular Nature of Human Interleukin-1," *J. of Immunol.*, 138(5):1447-1456 (Mar. 1, 1987).
Brody, et al., "Membrane IL-1: IL-1α Precursor Binds to the Plasma Membrane Via a Lectin-Like Interaction," *J. of Immunol.*, 143(4):1183-1187 (Aug. 15, 1989).
Cameron, et al. "Purification to Homogeneity and Amino Acid Sequence Analysis of Two Anionic Species of Human Interleukin 1," *J. Exp. Med.*, 164(1):237-250 (Jul. 1986).
Dixon, et al., "Apoptosis: Its Role in the Development of Malignancies and Its Potential as a Novel Therapeutic Target," *The Annals of Pharmacotherapy*, 31:76-82 (Jan. 1997).
Duvall, et al., "Death and the Cell," *Immunol. Today*, 7:115-119 (1986).
Gerschenson, et al., "Apoptosis: a Different Type of Cell Death," *FASEB*, , 6-2450-2455 (Apr. 1992).
Graves, Bradford J., et al., "Structure of Interleukin 1α at 2.7-Å Resolution", *Biochemistry* (1990) 29:2679-2684.
Guchelear, et al., "Apoptosis: Molecular Mechanics and Implications for Cancer Chemotherapy," *Pharmacy World & Science*, 19(3):119-125 (1997).
Kavita, et al., "Differential Sensitivity of Interleukin-1α and -β Precursor Proteins to Cleavage by Calpain, a Calcium-Dependent Protease," *The J. of Biol. Chem.*, 270(40):27758-27765 (Nov. 17, 1995).
Kronheim, et al., "Human Interleukin 1," *J. Exp. Med.*, 161:490-502 (Mar. 1985).
Lomedico, et al., "Cloning and Expression of Murine Interleukin-1 cDNA in *Escherichia coli*," *Nature*, 312:458-462 (Nov. 1984).
March, et al., "Cloning, Sequence and Expression of Two Distinct Human Interleukin-1 Complimentary DNA's," *Nature*, 315:(Jun. 1985).
Mayer, et al., "Programmed Cell Death: Will it Become a Factor in Cancer Prevention?," *Euro. J. of Cancer Prevention*, 6:323-329 (1997).
Mosley, et al., "The Interleukin-1 Receptor Binds the Human Interleukin-1α Precursor but Not the Interleukin-1β Precursor," *J. of Biol. Chem.*, 262(7):2941-2944 (Mar. 5, 1987).
Mosley, et al., "Determination of the Minumum Polypeptide Lengths of the Functionality Active Sites of Human Interleukins 1α and 1β," *Proc. Nat'l. Acad. Sci.*, 84:4572-4576 (Jul. 1987).

(Continued)

Primary Examiner—Christopher H. Yaen
(74) Attorney, Agent, or Firm—James S. Keddie; Carol L. Francis; Bozicevic, Field & Francis LLP

(57) ABSTRACT

The present invention is directed to compositions and methods for selective induction of apoptosis in cancer cells, particularly malignant cancer cells, by delivery of a IL-1α propiece polypeptide (e.g., a native IL-1α propiece polypeptide, including IL-1α propiece polypeptide variant) to a cancer cell.

9 Claims, 3 Drawing Sheets

OTHER PUBLICATIONS

Siders, et al., Characterization of the Structural Requirements and Cell Type Specificity of IL-1α and IL-1β Secretion, *J. of Biol. Chem.*, 268(29):22170-22174 (Oct. 1993).

Stevenson, et al., "The N-Terminal Propiece of Interleukin 1α is a Transforming Nuclear Oncoprotein," *Proc. Nat'l. Acad. Sci.*, 94:508-513 (Jan. 1997).

Stevenson, et al., "The 31-kDa Precursor of Interleukin 1α is Myristoylated on Specific Lysines Within 16-kDa N-Terminal Propiece," *Proc. Nat'l. Acad. Sci.*, 90:7245-7249 (Aug. 1993).

Tang, et al., "Target to Apoptosis: A Hopeful Weapon for Prostate Cancer," *The Prostate*, 32:284-293 (1997).

Walker, et al., "Patterns of Cell Death," *Meth. Achiev. Exp. Path.*, 13:18-54 (1998).

Wessendorf, et al., "Identification of a Nuclear Localization Sequence Within the Structure of the Human Interleukin-1 Aplpha Precursor," *J. Biol. Chem.* 268(29):22100-22104 (Oct. 15, 1993).

Zav'yalov, et al., "Receptor-Binding Properties of the Peptides Corresponding to the ACTH-Like Sequence of Human Pro-Interleukin-1α," *Immunology Letters*, 46:125-128 (1995).

Zsebo, K.M., et al., "Effects of Hematopoietin-1 and Interleukin 1 Activities on Early Hematopoietic Cells of the Bone Marrow", *Blood* (1988) 71(4):962-968.

\* cited by examiner

Fig. 6

```
                                            10                    20                    30
IL-1apro anal of AC006933 PEPTI
IL1 pro pep (mac)               M A K V P D M F E D L K N C Y S E N E E D S S S I D H L S L 40                    50                    60
IL-1apro anal of AC006933 PEPTI                                   G R H S L S L S L S L
IL1 pro pep (mac)               N Q K S F Y H V S Y G P L H E G   G M D Q S V S L S E T S
                                                                  C         S   S L S   S 70                    80                    90
IL-1apro anal of AC006933 PEPTI S V S - L C F R L S L V Y L N -   G Q V H K K R V Y A I S Q
IL1 pro pep (mac)               K T S K L T F K E S M V A T N     G K V L K K R R L S L S Q
                                S       L . F .   S . V   V .     G . V     K K R     . S Q 100                   110                   120
IL-1apro anal of AC006933 PEPTI F A N N N K A G G I S L S         E E
IL1 pro pep (mac)               S I T D D D L E A I A N D S E     E I I K P R S A P F S F
                                        I                         E E
```

SELECTIVE INDUCTION OF CELL DEATH BY DELIVERY OF AMINO-TERMINAL INTERLEUKIN-1-α PRO-PIECE POLYPEPTIDE

CROSS-REFERENCE TO RELATED APPLICATIONS

This application is a continuation-in-part of U.S. application Ser. No. 09/085,305, filed May 27, 1998 now U.S. Pat. No. 6,191,269, filed Feb. 20, 2001, which application claims the benefit of provisional application Ser. No. 60/048,137, filed May 30, 1997, each of which applications are incorporated herein by reference.

STATEMENT AS TO FEDERALLY SPONSORED RESEARCH

This invention was made with United States Government support under Grant Number DK31398 and Grant Number DK39776, awarded by the National Institutes of Health. The United States Government may have certain rights in this invention.

BACKGROUND OF THE INVENTION

The cytokine interleukin-1 (IL-1) was initially described as a low molecular weight protein that acted in conjunction with plant lectins to stimulate the proliferation of murine thymocytes. The spectrum of IL-1-mediated biologic properties is diverse, and includes modulation of the cellular immune response as well as induction of acute inflammatory mediators, such as prostaglandins. Produced primarily by activated monocytes, macrophages and polymorphonuclear leukocytes, IL-1 exists as two distinct genetic forms, termed Interleukin-1α (IL-1α) and Interleukin-1β (IL-1β). Both IL-1α and IL-1β are synthesized as precursor proteins of 31–33 kDa size and are subsequently cleaved to mature proteins of 15–17 kDa. The C-terminal halves of IL-1α and IL-1β are often referred to as "mature" IL-1β and "mature" IL-α," respectively, while the N-terminal halves are referred to as the N-terminal IL-1α (or IL-1β) propiece. The C-terminal halves of the precursor molecules of IL-1β and IL-1α are not found within cells, suggesting that processing occurs concurrent with release. Notably, it is the C-terminal halves of the IL-1α and IL-1β molecules that specifically interact with the Types I and II plasma membrane IL-1 receptors, and it is this interaction, prior to the current invention, to which all reported activities of IL-1 have been ascribed.

There are distinct differences between the IL-1α and IL-1β molecules in terms of sequence homology, intracellular distribution, kinetics of synthesis and mechanisms of proteolytic processing to the mature, C-terminal forms. For example, the precursor form of IL-1α is processed between Phe118 and Leu119 by calpain, a calcium-dependent protease. The precursor form of IL-β is processed by the specific IL-β converting enzyme (caspase) between Asp116 and Ala117.

Research has focused almost exclusively upon the activities of the processed C-terminal, membrane receptor-binding components of the IL-1 molecules. No specific biologic function has been ascribed to the 16 kDa N-terminal components of the precursors generated by proteolytic processing. Generation of polyclonal rabbit antibodies to synthetic peptides encoding epitopes for the N-terminal and C-terminal propieces of the IL-1α precursor molecule led to the histochemical observation that the N-terminal IL-1α propiece is present within the cell nucleus (Stevenson et al. (1992) *J Cell Physiol* 152:223–231). Subsequent studies using radioimmunoprecipitation of activated human monocyte lysates specifically recovered a 16 kDa protein with pI of 4.45, consistent with the predicted physicochemical properties of the IL-1α N-terminal propiece (Stevenson, et al. (1993) *Proc Natl Acad Sci USA* 90:7245–7249), thus demonstrating the existence of the native N-terminal IL-1α propiece within cells for the first time.

Examination of the cDNA sequence of the N-terminal IL-1α propiece revealed a polybasic region, T76-NGKV-LKKRRL (SEQ ID NO:28), which had characteristics of a nuclear localization sequence (NLS) and could mediate nuclear localization of the propiece (Stevenson et al. (1997) *Proc. Natl. Acad. Sci. USA* 94:508–13). Introduction of the cDNA encoding the N-terminal IL-α propiece into cultured mesangial cells resulted in nuclear accumulation (Stevenson et al. id). Stable expression of the N-terminal IL-1 propiece results in apoptotic death of cultured mesanglial cells and immortalized Rat-1 fibroblasts, which was reported to suggest a role for the polypeptide in the removal of excessive cell populations during the resolution of glomerular inflammation (Turck et al. (1995) *J. Am. Soc. Nephrol.* 6:779, abstract no. 2052).

Apoptosis, or "programmed cell death," is the process by which a cell actively self-destructs in response to certain developmental or environmental stimuli. Apoptosis functions to control cell populations during embryogenesis, immune responses, hormone withdrawal from dependent tissues, normal tissue homeostasis, and tumor regression, as described in Duvall et al. (1986) *Immunol. Today* 7:115–119; Walker et al. (1988) *Meth. Achiev. Exp. Pathol.* 13:18–54; and Gerschenson et al. (1992) *FASEB J.* 6:2450–2455.

Apoptosis may be induced by immunologically mediated methods, such as antibody dependent cell cytotoxicity (K cell attack), viral infection, and attack by cytotoxic T lymphocyte effector cells, lymphotoxins, or natural killer (NK) cells. Further, apoptosis may be induced in tumor cells by a variety of physical, chemical, and biochemical agents, such as gamma radiation, UV light, heat shock, cold shock, cisplatin, etoposide, teniposides, DNA alkylating agents, macromolecular synthesis inhibitors, and the like. The apoptotic death process is associated with profound, well-defined morphological changes in the cell. Cohen et al., (1984) *J. Immunol.* 132, 38–42 (1984).

Current approaches to chemotherapy could benefit from selective induction of apoptosis in cancer cells. For example, while combination chemotherapy is often the treatment of choice, it often involves the use of ill-tolerated drugs and onerous side effects, which are largely associated with the non-specific nature of the therapy (Kruit et al. (1996) *Br. J. Cancer* 74 (6):951). Thus, selective induction of apoptosis would be an attractive tool for cancer therapy. Unfortunately, development of apoptotic-based chemotherapy has met with many obstacles, include the identification of apoptosis-inducing agents that trigger cell death in cancerous cells, but do not substantially effect apoptosis in normal, non-cancerous cells. For recent reviews on the apoptosis in cancer chemotherapy see, e.g., Dixon et al. (1997) *Ann. Pharmacother.* 31:76–82; Guchelaar et al. (1997) *Pharm. World Sci.* 19:119–125; Mayer et al. (1997) *Eur. J. Cancer Prev.* 6:323–329; Tang et al. (1998) *Prostate* 32:284–293.

Thus, there is an urgent need for compositions and methods for use in chemotherapy that are both effective and selectively kill cancerous cells. The present invention addresses this problem.

SUMMARY OF THE INVENTION

The present invention is directed to compositions and methods for selective induction of apoptosis in cancer cells, particularly malignant cancer cells, by delivery of a IL-1α propiece polypeptide (e.g., a native IL-1α propiece polypeptide, including IL-1α propiece polypeptide variants) to a cancer cell.

Thus, in one aspect, the invention features an isolated polypeptide characterized by: a) a nuclear localization sequence, b) amino acid residues 75–108 of SEQ ID NO:2 and equivalents thereof retaining selective apoptosis-inducing activity, and c) an affinity ligand, wherein the polypeptide is characterized by activity in selective induction of apoptosis in a cancer cell. In one embodiment, the nuclear localization sequence and the apoptosis-inducing amino acid sequence are provided by amino acid residues 55–108 or 1–118 of an N-terminal IL-1α propiece polypeptide. In further related aspects, the invention features an isolated nucleic acid molecule encoding such apoptosis-inducing polypeptides.

In related aspects, the invention features an isolated polypeptide characterized by activity in selective induction of apoptosis in a cancer cell, the polypeptide having: a) amino acid residues 1–108, 11–118, 34–118, 55–118, or 55–108 of SEQ ID NO:2 (or of SEQ ID NO:2 having an amino acid other than serine at position 87); b) amino acid residues 75–108 of SEQ ID NO:2 (or of SEQ ID NO:2 having an amino acid other than serine at position 87), where the amino acid sequence is coupled to a heterologous nuclear localization sequence; c) amino acid residues 1–118, 1–108, or 55–108 of SEQ ID NO:2 (or of SEQ ID NO:2 having an amino acid other than serine at position 87) coupled to a leucine zipper domain; and d) equivalents thereof that retain selective apoptosis-inducing activity. In further related aspects, the invention features an isolated nucleic acid molecule encoding such apoptosis-inducing polypeptides.

In another aspect the invention features a method for selectively inducing apoptosis in a cancer cell, wherein the method comprises delivering an apoptosis-inducing polypeptide to a malignant cell in an amount effective to induce apoptosis. Delivery may be accomplished by introduction of an apoptosis-inducing polypeptide-encoding nucleic acid molecule into a cancer cell, extracellular delivery of the polypeptide to the cancer cell, or direct intracellular delivery of the polypeptide into the cancer cell. In preferred embodiments, the cancer cell is cell of a human tumor such as a colonic tumor, a central nervous system tumor, a leukemia cell, a lung tumor, a mammary tumor, a melanoma, an ovarian tumor, a prostate tumor, and a kidney tumor.

BRIEF DESCRIPTION OF THE DRAWINGS

FIG. 6 is schematic illustrating alignment of the amino acid sequence of human IL-1α propiece (1–118) (IL-1 pro pep (mac)) with a polypeptide from *Drosophila melanogaster* (IL-1apro anal of AC00593 PEPTI).

DESCRIPTION OF THE SPECIFIC EMBODIMENTS

Figure 1:
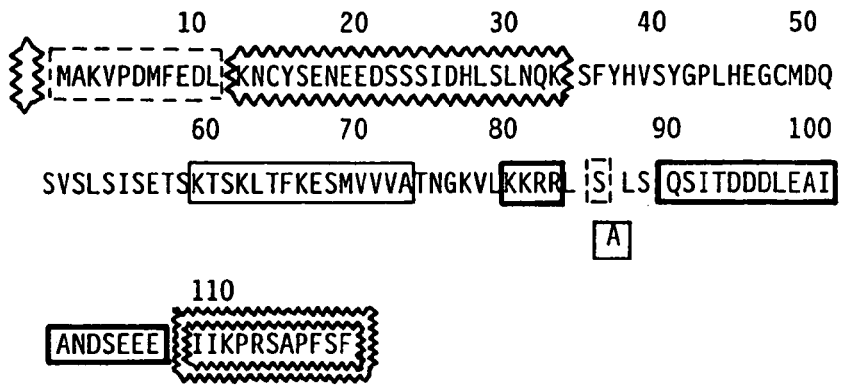
FIG. 1 is a schematic showing the amino acid sequence of native human IL-1α propiece (1–118) (SEQ ID NO:2), the positions of domains of interest, and the position of serine 87. The following residues of the amino acid sequence are noted in the figure: anionic residues 1–11 (which are not necessary for apoptosis induction), residues 1–34 (helix #1), residues of 34–74 (helix #2), residues 60–74 (region necessary for nuclear localization which can be substituted with a heterologous nuclear localization sequence), residues 81–84 (residues KKRR (SEQ ID NO:29), which are necessary but not sufficient for nuclear localization, and can be substituted by SV40 NLS), residue 87 (known phosphorylation site that when mutated does not substantially affect apoptotic activity), residues 90–108 (acidic domain essential for apoptosis induction), and residues 108–118 (not necessary for apoptosis)

Before the present method and compositions for induction of apoptosis in cancer cells are described, it is to be understood that this invention is not limited to the particular methodology, protocols, cell lines, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a malignant cell" includes a plurality of such cells and reference to "the polypeptide" includes reference to one or more polypeptides and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

Definitions

"Native N-terminal IL-1α propiece" refers to a polypeptide that is synthesized as an N-terminal portion of an IL-1α precursor polypeptide, and is subsequently released from the precursor polypeptide by proteolytic cleavage. "Native N-terminal IL-1α-propiece" is meant to encompass polypeptides derived from human, murine, bovine, and other eukaryotic sources, where the polypeptide is present at the N-terminus of an IL-1α precursor polypeptide. Exemplary IL-1α precursor polypeptides that encompass native N-terminal IL-1α propiece polypeptides of interest in the present invention are provided in the Sequence Listing, e.g., see SEQ ID NOS:7–20; 31–47; and 58–59). Preferably, native N-terminal IL-1α propiece is a native human IL-1α propiece, more preferably the polypeptide of SEQ ID NO:2 (encoded by SEQ ID NO:1 or an equivalent thereof). Native N-terminal IL-1α propiece polypeptides are normally characterized by a molecular weight of about 16 kDa and selective induction of apoptosis in a cancer cell, particularly a malignant cancer cell, as described herein. Native human N-terminal IL-1α propiece generally contains amino acids 1–118. "IL-1α propiece polypeptide" or "IL-1α propiece" is meant to encompass both a naturally occurring N-terminal product resulting from cleavage of a eukaryotic IL-1α precursor polypeptide (e.g., a mammalian IL-1α propiece polypeptide, e.g., a human IL-1α propiece polypeptide (IL-1α propiece (1–118) polypeptide)) as well as biologically active variants of an N-terminal IL-1α propiece polypeptide, unless specifically noted otherwise. Polypeptides of the invention comprising an IL-1α propiece sequence or IL-1α propiece-like sequence) may be of any origin (e.g., vertebrate or non-vertebrate, including from *Drosophila*), preferably mammalian, more preferably human origin. Exemplary IL-1α propiece polypeptides of interest also include, but are not necessarily limited to, IL-1α precursor polypeptides of non-human primate, canine, feline, rodent (e.g., rabbit, guinea pig, rat, mouse, etc.), equine, ruminants (e.g., ovine (e.g., sheep), goat, bovine, etc.), metathrial (e.g., opossum), swine (e.g., pig), and invertebrate (e.g., *Drosophila*, sea urchin, etc.) origin. The Sequence Listing provides the amino acid and/or nucleotide sequences of several exemplary IL-1α precursor polypeptides from which IL-1α propiece polypeptides and variants thereof can be derived and which are suitable for use in the present invention.

"IL-1α propiece (1–118) polypeptide" and "IL-1α (1–118)" refers to a polypeptide composed of amino acid residues 1–118 of an IL-1α precursor polypeptide. "IL-1α (1–118) polypeptide" or "IL-1α(1–118)" is also meant to encompass biologically active IL-1α propiece (1–118) variants unless noted otherwise (e.g., by the phrase "native IL-1α propiece (1–118)" or "IL-1α propiece (1–118) (SEQ ID NO:2)").

By "IL-1α propiece variant" or "IL-1α propiece biologically active variant" (which terms are generally used interchangeably unless specifically noted otherwise) is meant a polypeptide that is modified (e.g., having amino acid(s) insertion(s), deletion(s), substitution(s), and/or inversion(s) (e.g., fusion polypeptides (e.g., with immunoglobulin chains or portions thereof), chimeric polypeptides, fragments, conservative and non-conservative amino acid substitutions, and the like), post-translational modification (e.g., myristoylation, phosphorylation, glycosylation, and the like), and/ or chemical or biochemical modifications (e.g., PEGylation, conjugation to a detectable label or non-IL-1α propiece polypeptide (e.g., as in a fusion protein), and the like) relative to native N-terminal IL-1α propiece. Variants also encompass polypeptides that are dimerized, e.g., by chemical cross-linking or introduction of a dimerization domain, and/or are modified to contain a hormone binding domain (HBD) or other activity-regulatable sequence. Exemplary dimerization domain of interest in the IL-α propiece polypeptide variants of the invention include a synthetic (e.g., heterologous) leucine zipper domain, e.g., based on the leucine zipper domain of c-myc (Conseiller (1998) *J. Clin. Invest.* 101:120–7). For a review of leucine zipper domain structure and function, see, e.g., Alber (1992) *Curr Opin Genet Dev.* 2:205–210; Vinson, et al. (1989) *Science* 246 (4932):911–91; and Struhl (1989) *Trends Biochem Sci.*14 (4):137–140. Exemplary hormone binding domains include estrogen binding domains and variants thereof (e.g., an HBD that is mutated so that it is no longer responsive to its natural ligand, but is responsive to binding of a chemical analog of its natural ligand.

The nomenclature used herein for polypeptides and their encoding nucleic acids first indicates the polypeptide from which the variant is derived (e.g., an IL-1α N-terminal propiece polypeptide is indicated by IL-1α) followed by the amino acid residues of the polypeptide from which the variant is derived in parentheses (e.g., IL-1α(11–118) indicates that the polypeptide is derived from amino acid residues 11–118 of IL-1α N-terminal propiece polypeptide). Where the variant encompasses an amino acid change relative to native IL-1α propiece polypeptide, the change indicated by the one-letter code for the amino acid residue of native IL-1α propiece (1–118), the residue number, and the amino acid change (e.g., IL-1α propiece (1–118)(S87A) indicates a substitution of alanine for serine at residue 87 of IL-1α propiece (1–118)). Fusion proteins and other chimeras are indicated by abbreviated names for each amino acid sequence separated by dashes (e.g., IL-α propiece (1–118)-EGFP indicates a fusion protein between IL-1α propiece (1–118) and enhanced green fluorescent protein). The amino acid residue numbering used herein is that provided in FIGS. 1 and 2 (SEQ ID NO:2).

The term "biologically active IL-1α propiece variant" (e.g., as used in the context of "biologically active fragment of IL-1α propiece polypeptide," etc.) refers to a polypeptide having an amino acid sequence or modified amino acid sequence of IL-1α propiece polypeptide that, when delivered to a cancerous mammalian cell (particularly a malignant cancerous mammalian cell) induces apoptosis or otherwise inhibits cell growth.

The term "heterologous" as used herein to mean derived from different origins (e.g., from two different proteins of the same or different species or genus). For example, a polypeptide comprising an apoptosis-inducing domain a heterologous nuclear localization signal domain is meant to include polypeptides comprising an apoptosis-inducing domain from a first protein and a nuclear localization signal domain from a second protein, where the first and second proteins are different from each other.

"Apoptosis" is a process of programmed cell death that is defined by a number of characteristic phenomena, summarized in Cohen (1993) *Immunol. Today* 14:126–30. For example, in apoptotic cells, the cytoplasm condenses, and the endoplasmic reticulum dilates to form vesicles which fuse with the cell membrane, producing characteristic cellular morphology. The earliest changes in apoptosis appear in the mitochondria and are characterized by collapse in electrochemical gradients. Other early changes include an increase in the concentration of phosphatidyl serine on the outer leaflet of the plasma membrane in many cells. More advanced stages of apoptosis include changes in the nuclei including nuclear condensation, the formation of dense crescent-shaped aggregates of chromatin, nucleolus fragmentation, and formation of vesicles at or on the nuclear membrane. A classic signature of apoptosis is the cleavage of nuclear DNA into nucleosomal subunits. During apoptosis endonucleases present in the cell cut the DNA in the linker regions between nucleosomes to release DNA fragments in integer multiples of 180–190 base pairs, giving rise to the appearance of a ladder on gel electrophoresis (see, e.g., Gavrieli et al. (1992) *J. Cell Biol.* 119:493). There are also a variety of other assays available for apoptosis such as terminal deoxynucleotidyl transferase-mediated biotinylated dUTP (TUNEL) assays (see White et al. (1984) *J. Virol.* 52:410). Growth inhibition may be assessed using a number of commonly used assays, such as the methylcellulose assay (Lunardi-Iskandar et al. (1985) *Clin. Exp. Immunol.* 60:285–293).

"Selective induction of apoptosis" as used herein generally means induction of apoptosis in a first population of cells (e.g., of a first cell type or of a first origin) at a level or degree that is elevated relative to induction of apoptosis in a second population of cells (e.g., of a second cell type or of a second origin). For example, selective induction of apoptosis in a population of cancer cells indicates that, within cell populations, apoptosis is induced to a great degree in cancer cells relative to normal (e.g., non-cancerous) cells, to result in killing of a greater number of cancer cells than normal cells.

"Normal cell" is meant to describe a cell that is not immortalized, transformed, cancerous or malignant.

"Immortalized cell" means a cell that is characterized by its capacity for continuous culture and/or cells whose potential to proliferate is not limited to that approximately 50 cell divisions characteristic of normal cells as defined above, e.g., cells whose potential for cell division exceeds the Hayflick limit. Cells can be immortalized as a result of manipulation in in vitro culture (e.g., viral transfection, selection by continuous culture, etc.) or as a result of events that occurred in vivo in the host of origin. As used herein, "culture-immortalized cells" are those immortalized cells produced by manipulation in in vitro culture, while "tumor-derived immortalized cells" are those cells that were immortalized as a result of an in vivo event in the host of origin.

"Malignant cell" is meant to describe a transformed cell, generally an immortalized mammalian cell, that is characterized by loss of both growth control (e.g., rate of cell division) and positional control (e.g., infiltration of the cell to other sites in the host). The malignancy of a cell can be tested by injection of the cell into a host animal; development of tumors or cancers that are anaplastic, invasive, and/or metastatic is indicative of the malignant nature of the injected cell. In general, "malignant cell" as used herein is meant to refer to cells associated with (in vivo) or derived directly from (in vitro) a bona fide metastatic tumor in a mammal (especially a metastatic human tumor), e.g., as distinct from a cell immortalized in culture in vitro (i.e., culture-immortalized cell) or cells derived from such in vitro immortalized cells.

A "human" tumor is a tumor comprising cells that have human chromosomes. Such tumors include those in a human patient, and tumors resulting from the introduction of a human malignant cell line into a non-human host animal if cells from such tumors have human chromosomes.

"Apoptosis" refers to a process of programmed cell death, which is defined by a number of characteristic phenomena, such as nuclear changes (e.g., nuclear condensation, formation of dense crescent-shaped aggregates of chromatin, nucleolus fragmentation, formation of vesicles at or on the nuclear membrane, etc.), condensation of the cytoplasm, and dilation of the endoplasmic reticulum to form vesicles that fuse with the cell membrane, producing characteristic cellular morphology (see, e.g., Cohen, *Immunol. Today* 14:126–30 (1993).

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; (c) relieving the disease, i.e., causing regression of the disease; and (d) any subjective or objective improvement in the condition, including symptoms of a condition, of a mammal afflicted with a disease or condition (e.g., having cancer or a tumor, particularly a malignant cancer or tumor). For example, treatment encompasses improved vigor or vitality or decreased pain as subjective symptoms of improvement or response to therapy. Alternatively, the clinician may observe a decrease in tumor size or tumor burden based on physical exam, laboratory parameters, tumor markers, or radiographic findings.

The term "effective amount" means a dosage of a given substance that is sufficient to produce a desired result. The desired result can be subjective or objective improvement in the recipient of the dosage, a decrease in tumor size, a decrease in the rate of growth of cancer cells, or a decrease in metastasis.

The terms "nucleic acid" and "polynucleotide" refer to deoxyribonucleotides (e.g., DNA and cDNA) or ribonucleotides (e.g., mRNA) and polymers thereof in either single- or as double-stranded form. Unless specifically limited, the term encompasses nucleic acids containing analogues of natural nucleotides that have similar binding properties as the reference nucleic acid and are metabolized in a manner similar to naturally occurring nucleotides. Unless otherwise indicated, reference to a particular nucleic acid sequence is meant to encompass conservatively modified variants thereof (e.g., degenerate codon substitutions) and complementary sequences in addition to the specific sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al. (1985) *J. Biol. Chem.* 260:2605–2608; and Rossolini et al. (1994) *Mol. Cell. Probes* 8:91–98). The term nucleic acid is used interchangeably with gene, cDNA, and mRNA encoded by a gene. Unless otherwise indicated, a particular nucleic acid sequence includes the perfect complementary sequence thereof.

The phrase "a nucleic acid sequence encoding" or "a polynucleotide encoding" refers to a nucleic acid that contains sequence information for a structural RNA such as rRNA, a tRNA, or a primary amino acid sequence of a specific polypeptide, or a binding site for a trans-acting regulatory agent. This phrase specifically encompasses degenerate variants of the native sequence (i.e., different codons which encode a single amino acid) or sequences that may be introduced to conform with codon preference in a specific host cell.

"Substantial identity", when referring to the polynucleotides of this invention, means polynucleotides having at least 80%, typically at least 90% and preferably at least 95% sequence identity to a selected nucleotide sequence (e.g., SEQ ID NO:1). Sequence identity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) *J Mol Biol* 215:403–10. For the purposes of the present application, percent identity for the polynucleotides of the invention is determined using the BLASTN program with the default settings (including default gap weights) as described at http://www.ncbi.nlm.nih.gov/cgi-bin/BLAST/nph-new-blast?Jform=0 with the DUST filter selected. The DUST filter is described at http://www.ncbi.nlm.nih.gov/BLAST/filtered.html.

Nucleic acids having sequence similarity are detected by hybridization under low stringency conditions, for example, at 50° C. and 6×SSC (0.9 M saline/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/0.15 mM sodium citrate). By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, *Drosophila, Caenhorabditis*, etc.

Substantial identity, when referring to the polypeptides of the invention are polypeptides having at least 80%, typically at least 90% and preferably at least 95% identity to the amino acid sequence of SEQ ID NO: 2, or that are encoded by polynucleotides which will hybridize under stringent conditions to a polynucleotide having the nucleotide sequence of SEQ ID NO:1. Percent identity for the polypeptides of the invention is determined using the BLASTP program with the default settings (including default gap weights) as described at http://www.ncbi.nlm.nih.gov/cgi-bin/BLAST/nph-newblast? Jform=0 with the DUST filter selected. The DUST filter is described at http://www.ncbi.nlm.nih.gov/BLAST/filtered.html.

When percentage of sequence identity is used in reference to polypeptides it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4:11–17 (1988) e.g., as implemented in the program PC/GENE (Intelligenetics, Mountain View, Calif., USA).

A "conservative substitution" refers to a change in the amino acid composition of a polypeptide that does not substantially alter a selected biological activity of the polypeptide. Thus, "conservatively modified variations" of a particular amino acid sequence refers to substitutions of those amino acids that are not critical for a biological activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). See also, Creighton, *Proteins* W. H. Freeman and Company (1984). In addition, individual substitutions, deletions or additions which alter, add or delete a single amino acid or a small percentage of amino acids in an encoded sequence can also be "conservatively modified variations"

"Biological sample" as used herein is a sample of tissue or fluid from an organism that includes, but is not limited to, sputum, amniotic fluid, blood, blood cells (e.g., white cells), or tissue. Biological samples may also include sections of tissues such as frozen sections taken for histological purposes. Examples of biological samples include a cell sample from nervous, muscular, glandular or epithelial tissue or from the immune system (e.g., T cells). A biological sample is typically obtained from a eukaryotic organism, preferably a multicellular eukaryotes such as insect, protozoa, birds, fish, reptiles, and preferably a mammal such as rat, mice, cow, dog, guinea pig, or rabbit, and most preferably a primate such as macaques, chimpanzees, or humans.

The term "antibody" refers to a polypeptide substantially encoded by an immunoglobulin gene, or fragments thereof that specifically bind and recognize an analyte (antigen). "Antibody" encompasses immunoglobulin molecules of the classes IgG, IgM, IgA, IgD, IgE, and subclasses thereof (e.g., IgG1), and includes both monoclonal and polyclonal antibodies. The term "antibody" also encompasses any antigen binding antibody form (e.g., Fab, Fab', $F(ab)_2$, $F(ab)'_2$, single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies) and the like). Various antibody fragments can be produced by digestion of an intact antibody or by de novo synthesis (e.g., chemical synthesis or using recombinant DNA methodology).

The phrase "specifically binds to an antibody" or "specifically immunoreactive with", when referring to a polypeptide, refers to a binding reaction which is determinative of the presence of the protein in the presence of a heterogeneous population of polypeptides and other biologics. Thus, under designated immunoassay conditions, the specified antibodies bind to a particular polypeptide and do not significantly bind to other polypeptides present in the sample.

Overview

The present invention is based on the discovery that delivery of a IL-1α propiece polypeptide facilitates selective induction of apoptosis in cancerous cells, particularly malignant cancerous cells. Delivery of the apoptosis-inducing polypeptides of the invention can be accomplished in a variety of ways including, but not necessarily limited to, DNA-based polypeptide delivery (e.g., by introduction of an IL-1α propiece polypeptide-encoding polynucleotide and expression within the host cell), direct intracellular polypeptide introduction (e.g., by fusion of a polypeptide-comprising liposome with a target cell), and polypeptide delivery to the surface of that target cell (i.e., extracellular delivery). Furthermore, the inventors have discovered that while IL-1α propiece polypeptides facilitate induction of apoptosis in cancer cells (especially in malignant cancerous cells), the IL-1α propiece polypeptides generally do not substantially induce apoptosis in normal cells, making IL-1α propiece polypeptides of interest in chemotherapy. Induction of apoptosis in cancer cells decreases tumor growth and/or tumor mass, and facilitates tumor regression.

Apoptosis-Inducing Polypeptides of the Invention

Apoptosis-inducing polypeptides of the invention encompass N-terminal IL-1α propiece and variants thereof having biological activity in apoptosis induction in cancer cells, preferably in malignant cancer cells. Preferably, the apoptosis-inducing polypeptides of the invention facilitate apoptosis of malignant cells, but do not significantly or substantially facilitate apoptosis in normal cells. A degree of apoptosis induction in normal cells is tolerable, but preferably the apoptosis-inducing polypeptides of the invention facilitate apoptosis in malignant cancer cells more efficiently than in normal cells. For example, the apoptosis-inducing polypeptides of the invention may induce apoptosis of malignant cells in a shorted post-delivery time period than in normal cells, may facilitate apoptosis in malignant cells at lower polypeptide levels (e.g., with a smaller amount, lower concentration, lower expression level, etc.) than in normal cells, etc.

Apoptosis-inducing polypeptides of particular interest include, but are not necessarily limited to, native IL-1α propiece polypeptide, e.g., IL-1α propiece (1–118) defined by SEQ ID NO:2 and equivalents thereof. Also of particular interest are IL-1α propiece polypeptide variants, especially variants of SEQ ID NO:2, that retain apoptosis-inducing activity in malignant cells. Also of interest are IL-1α propiece polypeptides derived from human and non-human origins, e.g., human, non-human primate, canine, feline, rodent, equine, ruminant, marsupial (e.g., opossum, e.g., *Metatheria*) swine, and invertebrate origin (e.g., *Drosophila*). The Sequence Listing provides the amino acid and/or nucleotide sequences of several exemplary IL-1α propiece polypeptides from which IL-1α propiece polypeptides and variants thereof can be derived and which are suitable for use in the present invention (human (SEQ ID NO:7), bovine (SEQ ID NOS:8, 39 and 40), canine (SEQ ID NOS:9, 43 and 44), goat (SEQ ID NOS:10, 41 and 42), guinea pig (SEQ ID NO:11), *Cercocebus torquatus atys* (SEQ ID NO:12), equine (SEQ ID NO:13), feline (SEQ ID NO:14), *Macaca* (SEQ ID NOS:15, 35 and 36, 45 and 46), *Cercocebus* (SEQ ID NOS:47 and 48); mouse (SEQ ID NOS:16, 34), sheep (SEQ ID NO:17), rabbit (SEQ ID NO:18), rat (SEQ ID NOS:19, 33), pig (SEQ ID NOS:20, 37 and 38), hamster (SEQ ID NOS:31 and 32); and *Drosophila* (SEQ ID NOS:55 and 56)).

Native Human IL-1α Propiece Polypeptide

The amino acid sequence of human IL-1α propiece (1–118), and features of the polypeptide, are presented in FIG. 1 (SEQ ID NO:2). Native human IL-1α propiece (1–118) is composed of 118 amino acids and has now been characterized as containing: an anionic region (residues 1–11); three α-helices (α-helix #1: residues 1–34; α-helix #2: residues 34–70; and α-helix #3: residues 75–118); a basic sequence associated with nuclear localization (residues 81–84); a phosphorylation site at serine residue 87 (which site is not required for apoptotic activity), and an acidic domain which is required for the induction of apoptosis (from about residue 90 to about residue 108 or 118). In addition the basic region from about residue 60 to about residue 75 may be necessary for nuclear localization.

IL-1α Propiece Polypeptide Variants

IL-1α propiece polypeptide variants of the invention encompass polypeptides modified relative to a native N-terminal IL-1α propiece (e.g., having amino acid(s) insertion(s), deletion(s), substitution(s), and/or inversion(s) (e.g., fusion polypeptides, chimeric polypeptides, fragments, conservative and non-conservative amino acid substitutions, and the It like), post-translational modification (e.g., myristoylation, phosphorylation, glycosylation, and the like), and/or chemical or biochemical modifications (e.g., PEGylation, conjugation to a detectable label or non-IL-1α propiece polypeptide (e.g., as in a fusion protein), and the like). IL-1α propiece polypeptide variants of the invention are biologically active, e.g., when delivered to a malignant mammalian cell, induce apoptosis or otherwise inhibit cell growth.

Apoptotic activity involves at least two separable biological activities: 1) nuclear localization; and 2) induction of cell death. These activities of a biologically active IL-1α propiece polypeptide variant can be provided by naturally-occurring or synthetic amino acid sequences. For example, nuclear localization activity can be provided by a synthetic nuclear localization sequence (e.g., the nuclear localization sequence PKKKRKV (SEQ ID NO:30) from SV40) joined to a fragment of IL-1α(1–118) that has activity in inducing apoptosis.

IL-1α propiece polypeptide variants of particular interest include fragments of native IL-1α propiece (1–118) having apoptotic activity. In general, and without being held to theory, IL-1α propiece (1–118) variants comprise an amino acid sequence from about amino acid residue 50 or 55 to about amino acid residue 110 of SEQ ID NO:2 and equivalents thereof (e.g., the serine at residue 87 may be an amino acid other than serine). Specific exemplary IL-1α propiece polypeptide variants of the invention include, but are not limited to, IL-1α(11–118), IL-1α(34–118), and IL-1α (55–118), IL-1α propiece (1–118)(S87A), IL-1α propiece (1–118)-EGFP, IL-1α propiece(1–118)-Fc, analogs identified from human and non-human origins (e.g., mouse, rat, bovine, canine, feline, *Drosophila*, etc.), and equivalents thereof.

Production of IL-1α Propiece Polypeptide-Encoding Nucleic Acids

Nucleic acids encoding a native N-terminal IL-1α propiece may be obtained by any of a variety of methods known in the art (e.g., isolation from natural sources, obtained from ATCC or GenBank libraries, chemical synthesis, etc.) (see, e.g., Sambrook et al., (1989) *Molecular Cloning: A Laboratory Manual* (2$^{nd}$ Ed.), Vol. 1–3, Cold Spring Harbor Laboratory, Cold Spring Harbor, N.Y.). For example, DNA encoding a native N-terminal IL-1α propiece can be identified in either cDNA or genomic libraries by its ability to hybridize with nucleic acid probes designed to complement a portion of the nucleotide sequence of SEQ ID NO:1, and these polynucleotides isolated by standard methods familiar to those of skill in the art. Suitable probes can be prepared by methods well known in the art (e.g., chemical synthesis followed by purification by gel electrophoresis or anion-exchange HPLC (Pearson et al., (1983) *J. Chrom.*, 255: 137–149)). In general, sense and anti-sense probes will be of approximately 18 nucleotides to the full length of the gene, more typically approximately 30 nucleotides in length. Low stringency conditions, e.g., 50° C. and 6×SSC (0.9 M saline/0.09 M sodium citrate) are used to identify and isolate polynucleotides having nucleotide sequences similar to that of the probe. High stringency conditions, e.g., 50° C. or higher and 0.1×SSC (15 mM saline/1.5 mM sodium citrate) are used to identify and polynucleotides having nucleotides essentially identical to that of the probe. The isolated polynucleotides may be introduced into an appropriate vector for extrachromosomal maintenance or for integration into a host genome.

The polynucleotides of the invention may be obtained as double or single stranded fragments by conventional means, e.g., chemical synthesis, restriction enzyme digestion, PCR amplification, and the like. For the most part, small DNA fragments, such as those useful as primers for PCR, hybridization screening probes, etc., will be of at least 15 nt, usually at least 18 nt or 25 nt, and may be at least about 50 nt. PCR amplification requires a pair of primers, typically a pair which will generated an amplification product of at least 50 nucleotides, preferably at least 100 nucleotides in length. Suitable primers hybridize to the target polynucleotide under stringent conditions. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Software designed for selecting suitable sequences for primers are commercially available. Larger DNA fragments, e.g., usually greater than about 100 nt are useful for production of the encoded polypeptide.

Polynucleotides of particular interest are polynucleotides encoding native IL-1α propiece (1–118) and IL-1α propiece (1–118) variants. The polynucleotide and amino acid sequences of native human IL-1α precursor, which sequences include native human IL-1α propiece (1–118), are provided in GenBank at accession number X02851, and are described in Furutani et al. (1985) *Nucleic Acids Res.* 13:5869. The nucleotide sequence of native human IL-1α propiece (1–118) is provided herein as SEQ ID NO:1.

Production of IL-1α Propiece Polypeptide Variants

Polynucleotides encoding variants of a native N-terminal IL-1α propiece can be prepared by methods known in the art. For example, techniques for site specific in vitro mutagenesis are found in Gustin et al. (1993), *Biotechniques* 14:22; Barany (1985), *Gene* 37:111–23; Colicelli et al. (1985), *Mol. Gen. Genet.* 199:537–9; and Prentki et al., (1984), *Gene* 29:303–13; Sambrook, et al., supra, pp 15.3–108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech.* 6:67–70; Zhu (1989), *Anal Biochem* 177: 120–4; Taylor et al., (1985) *Nucl. Acids Res.* 13:8749–8764; and Kunkel (1985) *Proc. Natl. Acad. Sci. USA* 82:482–492. Methods of using computer modeling for the design of variants of a selected polypeptide are also well known in the art.

The resulting variants may, for example, contain mutations in a native N-terminal IL-1α propiece sequence. The sequence changes may be substitutions, insertions, deletions, or inversions, or a combination thereof. For example, nucleotide changes may be associated with a degenerate variant of the parent nucleic acid molecule (i.e., the mutation does not change the amino acid sequence encoded by the mutated codon) or non-degenerate (i.e., the mutation changes the amino acid sequence encoded by the mutated codon). Deletions may further include larger changes, such as deletions of a domain associated with a feature or characteristic of the native polypeptide (e.g., deletion of helix #1 of native IL-1α propiece (1–118)).

Other modified IL-1α propiece polypeptides contemplated by the IL-α propiece polypeptides of the invention include fusion proteins. Such fusion proteins minimally comprise an apoptosis-inducing domain of an IL-α propiece polypeptide (e.g., native IL-α propiece polypeptide or variant IL-α propiece polypeptide retaining apoptosis-inducing activity), and may be operably linked to any heterologous polypeptide of interest. Modifications of interest include epitope tagging, e.g. with the FLAG system, HA, etc., as well as production of fusion proteins, e.g., using green fluorescent proteins (GFP, EGFP, etc.), GST (Glutathione S-Transferase), and the like. In one embodiment, an apoptosis-inducing domain of an IL-α propiece polypeptide of the invention is operably connected to all of a portion of an antibody chain (e.g., antibody heavy chain, antibody light chain, generally an antibody heavy chain) or fragment there of (e.g., Fc region of an antibody heavy chain, which region may encompass the hinge region). In this embodiment, the antibody chain or portion thereof can be derived from any suitable source (e.g. human, non-human (e.g., mouse, rat, goat, guinea pig, and the like), etc.), and can encompass an region of interest (e.g., an antigen-binding portion of an immunoglobulin chain polypeptide and/or a complement-binding portion of an immunoglobulin chain polypeptide (e.g., an Fc region)).

Both degenerate and non-degenerate mutations may be advantageous in producing or using the polypeptides of the present invention. For example, these mutations may permit higher levels of production, easier purification, or provide additional restriction endonuclease recognition sites. All such modified DNAs (and the encoded polypeptide molecules) are included within the scope of the present invention.

Screening for Biological Activity of Candidate IL-1α Propiece Polypeptide Variants IL-1α propiece polypeptide variants having biological activity in inducing apoptosis of a desired target cell (e.g., a malignant cancerous cell) can be identified by screening variant polypeptide candidates using a cell-based in vivo assay and/or using an animal model to assess the ability of the candidate variants to induce apoptosis in a targeted tumor as determined by, e.g., inhibition of tumor growth. Such screening assays may involve delivery of a variant-encoding polynucleotide to a target cell for expression within the target cell, direct intracellular It delivery of the variant polypeptide (e.g., by microinjection), and/or extracellular delivery of the candidate variant polypeptide to a target cell.

Apoptosis can be measured by a variety of techniques, reviewed in Cohen (1993) *Immunol. Today* 14: 126–30. For example, apoptosis can be measured by determination of cell phenotype. Phenotype refers to how the cell looks, typically microscopically, but gross or macroscopic appearance can be observed. Cell phenotype changes are dependent upon cellular growth rate. For instance, the microscopic morphology of cells that are rapidly dividing and growing is different than that of cells undergoing cell death by apoptosis. Determination of cell phenotype is well within the ability of one with ordinary skill in the art.

Apoptosis can also be evaluated using a number of biochemical assays, such as "laddering" of the cellular DNA. When testing compounds for the ability to induce apoptosis, cell death (not cytostasis) is an endpoint of compound application to the cell. A classic signature of apoptosis is the cleavage of nuclear DNA into nucleosomal subunits. When subjected to agarose gel electrophoresis, this phenomenon results in the appearance of a DNA ladder as nucleosomal units are sequentially cleaved from the DNA. The appearance of the DNA ladder is thus indicative of cell death (see, e.g., Gavrieli et al. (1992) *J. Cell Biol.* 119:493).

In a preferred embodiment, candidate variant polypeptides are assayed for activity in a cell-based assay by expression of candidate variant polypeptide-encoding DNA in a target cell or by extracellular delivery of a candidate polypeptide to a target cell. Apoptosis can be evaluated by the formation of DNA ladders after agarose gel electrophoresis of isolated chromosomal DNA, by the TUNEL method (which involves 3' end-labeling of cleaved nuclear DNA) (Cohen et al. (1984) *J. Immunol.* 132:38–42; White et al. (1984) *J. Virol.* 52:410), and/or morphological criteria (Cohen et al., supra). The TUNEL method can also be used to biologically evaluate implanted tumors for apoptosis. Growth inhibition may be assessed using a number of commonly used assays, such as the methylcellulose assay (Lunardi-Iskandar et al., *Clin. Exp. Immunol.* 60:285–293 (1985)). Growth inhibition may be assessed as a measurement of apoptosis using a number of commonly used assays, such as the methylcellulose assay (Lunardi-Iskandar et al. (1985) *Clin. Exp. Immunol.* 60:285–293).

Rapid screening of IL-1α(1–118) polypeptide variant candidates can be accomplished by the use of a reporter (e.g., EGFP) fused to the IL-1α propiece polypeptide candidate variant. For example, the IL-1α propiece (1–118) variant candidate can be fused to EGFP to provide an IL-1α propiece (1–118)-EGFP fusion polypeptide, the fusion polypeptide delivered to the target cells, and apoptosis evaluated by distribution of IL-1α(1–118)-EGFP-associated fluorescence. Distribution of reporter polypeptides such as IL-1α(1–118)-EGFP in apoptotic cells is identical to the distribution of DAPI or Hoechst 33342 dyes, which are conventionally used to detect the nuclear DNA changes associated with apoptosis (Cohen et al., supra). Moreover, the presence of the reporter polypeptide does not substantially affect the ability of the polypeptide to induce apoptosis. Thus, the presence of IL-1α propiece (1–118)-EGFP-associated fluorescence in fragmented nuclear bodies or apoptotic bodies is indicative of induction of apoptosis in the target cell.

Activity in apoptosis induction can also be assess by delivering the IL-1α propiece polypeptide variant candidate polypeptide to target cancer cells, and then implanting the treated cancer cells into a non-human animal model. Inhibition of the ability of the treated cells to facilitate tumor production, growth, or metastasis relative to untreated cells is indicative of the apoptotic-activity of the candidate variant polypeptide. Similarly, apoptotic activity of candidate variant polypeptides can be assessed by delivery of the candidate variant directly to a tumor in an in vivo animal model.

Constructs and Vectors Useful for IL-1α Propiece Polypeptide Expression

Once a nucleic acid encoding a polypeptide of the invention is isolated and cloned, the nucleic acid may be expressed in any of a variety of recombinantly engineered cells. Expression of natural or synthetic nucleic acids is typically achieved by operably linking a nucleic acid of interest to a promoter (which is either constitutive or inducible), incorporating the construct into an expression vector, and introducing the vector into a suitable host cell.

Typical expression vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors may be suitable for replication and integration in prokaryotes, eukaryotes, or preferably both. In general, the nucleic acids (e.g., promoters and vectors) useful in the composition and methods of the invention can be isolated from natural sources, obtained from such sources as ATCC or GenBank libraries, or prepared by synthetic methods. Synthetic nucleic acids can be prepared by a variety of solution or solid phase methods.

Any suitable promoter can be used in expression constructs for production of IL-1α propiece polypeptides. For example, the promoter may be a non-specific strong promoter (e.g., CMV promoter, human tyrosinase promoter (nt 26-2293 of GenBank accession no. U03039) or a tissue-specific promoter, e.g., a promoter that facilitates enhanced transcriptional activity in the target cell but substantially no transcription or relatively lower transcription in non-target cells). Preferably, the expression construct is prepared so that the promoter-IL-1α propiece polypeptide-encoding polynucleotide is positioned within a sequence containing convenient restriction sites, thus providing an expression cassette that can be easily moved between various expression constructs.

The promoter in the expression construct can be modified to increase its specificity and transcription levels (e.g., potency) in a target cell or target cell type. For example, the tyrosinase promoter can be modified to increase its specificity and potency in melanoma cells, e.g., by including 209 base pairs 5' to the transcription start site along with two additional melanoma-specific promoter fragments placed 5' to the 209 bp fragment (Siders et al. (1996) *Cancer Res.* 56(24):5638–46).

A number of vector systems can be used to express the polypeptides of the invention. These include plasmids, cosmids, and a number of viral vectors, including retroviral vectors, vaccinia vectors, lentiviral vectors, herpes virus vectors (e.g. HSV), Sindbis/semliki forest viruses, adenoviral vectors, and adeno-associated viral (AAV) vectors. Each vector system has advantages and disadvantages, which relate to host cell range, intracellular location, level and duration of transgene expression and ease of scale-up/purification.

In a preferred embodiment, an expression cassette for expressing IL-1α propiece polypeptides comprises (from 5' to 3'): 1) a strong promoter or tissue-specific promoter; 2) optionally, a splice signal, as might be found in the first intron of the human growth hormone gene (nucleotides 565–831 of GenBank M13438); 3) an IL-1α propiece polypeptide coding sequence; and 4) an SV40 or other polyadenylation signal. For in vivo expression, this entire cassette is preferably cloned into an adenovirus E1 type shuttle vector, such as pAC, which contains map units 0–1.5 and map units 9–17 of Adenovirus type 5. This construct can be used to make replication-defective adenoviruses by standard techniques.

Suitable constructs for IL-1α propiece polypeptide expression can be selected according to the ability of such construct to facilitate a desired level of polypeptide production in a selected target cell. For example, the same expression construct may provide for varying expression levels in different cancer cell types; likewise, different expression constructs may provide for varying expression levels in the same cancer cell type. Thus, it is desirable to select an expression construct that provides an optimal level of IL-1α propiece polypeptide expression in the selected target cancer cell type. Methods and compositions for preparation of various constructs and modification of such construct to optimize expression, are well known in the art.

IL-1α propiece polypeptide expression can be detected and quantified by any of a number of means well known to those of skill in the art involving detection of transcription or translation products of the IL-1α propiece polypeptide-encoding polynucleotide. For example, expression can be detected by analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitation reactions, immunodiffusion (single or double), immunoelectrophoresis, radioimmunoassays (RIAs), enzyme-linked immunosorbent assays (ELISAs), immunofluorescent assays, and the like. The detection of nucleic acids proceeds by well known methods such as Southern analysis, northern analysis, gel electrophoresis, PCR, radiolabeling, scintillation counting, and affinity chromatography (see, e.g., Sambrook, et al.; supra).

Constructs Suitable for Delivery to and Expression in Target Cells In Vivo

Where the polynucleotide is to be prepared for delivery to and expression in a target cell (e.g., a malignant cell) in a mammalian host, the polynucleotide may be prepared as either a viral or non-viral delivery and expression system. In general, the optimal delivery systems are characterized by: 1) a suitable host range (e.g., ability to selectively deliver the polynucleotide to a target cell (e.g., a malignant cell) or, where the polypeptide to be expressed does not substantially elicit apoptosis in normal cells, a broad host range may be permissible or desirable); 2) stable expression or high levels of transient expression; and 3) non-toxic to normal cells (e.g., to diminish undesirable side-effects). Where the delivery system is virally-based, the delivery system is optimally further characterized by: 1) high titer/µg DNA; 2) substantially no replication in host cells; 3) ideally substantially no viral gene expression; 4) stable transmission to daughter cells (e.g., where apoptosis is effected in cells following one or more rounds of cell division); 5) high rescue yield; and 6) substantially no or relatively little replication-competent virus.

The constructs and delivery system used will vary according to a variety of factors, such as the intended application, the target cell, etc.

Non-Viral Delivery Systems

Non-viral delivery systems include naked nucleic acid (e.g., as per U.S. Pat. Nos. 5,693,622 and 5,580,859), transfection-facilitating proteins (e.g., DNA-protein formulations), liposomal formulations (e.g., U.S. Pat. Nos. 4,394,438; 5,459,127), charged lipids, calcium phosphate precipitating agents, DNA-targeting ligand formulations (e.g., to facilitate receptor-mediated endocytosis), polycationic substances such as poly-L-lysine or DEAC-dextran(Felgner et al., (1987) Proc. Natl. Acad. Sci. U.S.A. 84:7413–7417), and the like. Methods and compositions for production of such non-viral delivery systems are well known in the art.

Viral Expression and Delivery Systems

Viral vectors suitable for use in the present invention include any viral vector suitable for delivery of a IL-1α propiece polypeptide-encoding polynucleotide to a cancer target cell and expression in the target cell at a level sufficient to induce apoptosis in the target cancer cell. Viral vectors of particular interest include, but are not necessarily limited to, those vectors based on retroviruses (including pseudotyped retroviruses, and Lentiviruses, such as HIV-based vectors, which may not require cell division), Sindbis virus, adeno-associated virus (AAV), adenovirus, poxvirus, semliki-forest virus (SFV), and herpesvirus (e.g., CMV, HSV, etc.). Exemplary viral vectors suitable for use in the in vivo delivery methods of the invention are described below.

Retroviral Vectors

Retroviral vectors may also be used in certain applications. The design of retroviral vectors is well known to one of skill in the art. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are commonly used to construct retroviral vectors. Preparation of retroviral vectors and their uses are described in many publications including EP-A 0 178 220, U.S. Pat. No. 4,405,712; Gilboa (1986) Biotechniques 4:504–512; Mann et al. (1983) Cell 33:153–159 Cone et al. (1984) Proc. Natl. Acad. Sci. USA 81:6349–6353; Eglitis et al. (1988) Biotechniques 6:608–614; Miller et al. (1989) Biotechniques 7:981–990; and WO 92/07943.

The retroviral vector particles are prepared by recombinantly inserting a nucleic acid encoding a gene product of interest into a retrovirus vector and packaging the vector with retroviral capsid proteins by use of a packaging cell line. The resultant retroviral vector particle is generally incapable of replication in the host cell and is capable of integrating into the host cell genome as a proviral sequence containing the nucleic acid of interest. As a result, the host cell produces the gene product encoded by the nucleic acid of interest.

Packaging cell lines are generally used to prepare the retroviral vector particles. A packaging cell line is a genetically constructed mammalian tissue culture cell line that produces the necessary viral structural proteins required for packaging, but which is incapable of producing infectious virions. Retroviral vectors, on the other hand, lack the structural genes but have the nucleic acid sequences necessary for packaging. To prepare a packaging cell line, an infectious clone of a desired retrovirus, in which the packaging site has been deleted, is constructed. Cells comprising this construct will express all structural proteins but the introduced DNA will be incapable of being packaged. Alternatively, packaging cell lines can be produced by transducing a cell line with one or more expression plasmids encoding the appropriate core and envelope proteins. In these cells, the gag, pol, and env genes can be derived from the same or different retroviruses.

A number of packaging cell lines suitable for the present invention are available in the prior art. Examples of these cell lines include Crip, GPE86, PA317 and PG13 (see, e.g., Miller et al. (1991) J. Virol. 65:2220–2224). Examples of other packaging cell lines are described in Cone et al., (1984) Proc. Natl. Acad. Sci. USA 81:6349–6353; Danos et al. (1988) Proc. Natl. Acad. Sci. USA 85:6460–6464; Eglitis et al. (1988) Biotechniques 6:608–614; Miller et al. (1989) Biotechniques 7:981–990. Amphotropic or xenotropic envelope proteins, such as those produced by PA317 and GPX packaging cell lines may also be used to package the retroviral vectors. Also of interest is the use of packaging cell lines that produce pseudotyped viral particles having vesicular stomatitis viral coat protein (VSV G), which may be obtained either by transient transfection of a packaging cell line (e.g., a cell expressing a retroviral gag and pol) or through use of a packaging cell line that stably expresses VSV G.

Sindbis/Semliki Forest Viruses

Sindbis/semliki forest viruses (Berglund et al. (1993) *Biotechnol* 11:916–920) are positive-strand RNA viruses that replicate in the cytoplasm, are stably maintained, and can yield very high levels of antisense RNA. Sindbis vectors are thus a third type of vector useful for maximal utility. See, e.g., Altman-Hamamdzic et al. (1997) *Gene Therap* 4:815–22.

Adeno-Associated Virus (AAV) Vectors

Because of their demonstrated ease of use, broad host range, stable transmission to daughter cells, high titer/microgram DNA, and stable expression, (Lebkowski et al. (1988) *Mol. Cell. Biol.* 8:3988–3996), AAV vectors are a preferred viral vector for delivery of IL-1α propiece polypeptide-encoding polynucleotides to target cells (see, e.g., Goeddel (ed.) (1990) *Methods in Enzymology, Vol. 185*, Academic Press, Inc., San Diego, Calif.; Krieger, (1990) *Gene Transfer and Expression—A Laboratory Manual*, Stockton Press, New York, N.Y.; and references cited therein). AAV requires helper viruses such as adenovirus or herpes virus to achieve productive infection.

In the absence of helper virus functions, AAV integrates (site-specifically) into a host cell's genome. The integrated AAV genome has no pathogenic effect. The integration step allows the AAV genome to remain genetically intact until the host is exposed to the appropriate environmental conditions (e.g., a lytic helper virus), whereupon it re-enters the lytic life-cycle. For discussion of AAV, AAV vectors, and uses thereof, see, e.g., Samulski (1993) *Curr. Opin. Genet. Dev.* 3:74–80 (references cited therein for an overview of the AAV life cycle); West et al. (1987) *Virology* 160:38–47; U.S. Pat. No. 4,797,368; WO 93/24641; Kotin (1994) *Hum. Gene Therap.* 5:793–801; Muzyczka (1994) *J. Clin. Invest.* 94:1351; and Samulski, supra.

AAV displays a very broad range of hosts including chicken, rodent, monkey and human cells (Muzycka, N., *Curr. Top. Microbiol. Immunol.* 158, 97–129 (1992); Tratschin et al., (1985) *Mol. Cell. Biol.* 5:3251–3260; Lebkowski et al. (1988) *Mol. Cell. Biol.* 8:3988–3996). They efficiently transduce a wide variety of dividing and non-dividing cell types in vitro (Flotte et al. (1992) *Am. J. Respir. Cell. Mol. Biol.* 7:349–356); Podsakoff et al. (1994) *J. Virol.* 68 5655–5666), Alexander et al (1994) *J. Virol.* 68:8282–8287). AAV vectors have been demonstrated to successfully transduce hematopoietic progenitor cells of rodent or human origin (Nahreini et al. (1991) *Blood* 78:2079). It is believed that AAV may infect virtually any mammalian cell type.

Production of AAV vectors for delivery of IL-1α propiece polynucleotides can be accomplished according to methods well known in the art. Once a cell or cells have been selected and shown to contain an IL-1α propiece polynucleotide of interest, the entire AAV-IL-1α propiece polypeptide expression cassette can be easily "rescued" from the host cell genome and amplified by introduction of the AAV viral proteins and wild type adenovirus (Hermonat et al. (1984) *Proc. Natl. Acad. Sci. USA* 81:6466–6470; Tratschin et al. (1985) *Mol. Cell. Biol.* 5:3251–3260; Samulski et al. (1982) *Proc. Natl. Acad. Sci. USA* 79:2077–2081; Tratschin et al. (1985) *Mol. Cell. Biol.* 5:3251–3260).

The copy number of genes introduced by the AAV vector is about 2 orders of magnitude higher or more than that of retrovirally-transduced human tumor-infiltrating lymphocyte (TIL) cell cultures. In vivo expression of AAV-delivered genes is relatively long, and may last up to 6 months or more (Conrad et al. (1996) *Gene Therapy* 3:658–668). Persistence of an AAV-delivered gene has been observed in humans for at least 70 days (10th Annual North American Cystic Fibrosis Conference, Orlando, Fla., Oct. 25–27, 1996).

The promoters used to control the gene expression from AAV include: (a) viral promoters such as SV40, CMV, retroviral LTRs, herpes virus TK promoter, parvovirus B-19 promoter (Muzycka (1992) *Curr. Top. Microbiol. Immunol.* 158:97–129), AAV p5 and p40 promoters (Tratschin et al. (1993) *Am. J. Respir. Cell. Mol. Biol.* 7, 349–356); (b) human gene promoters such as the gamma-globin promoter (Walsh et al. (1992) *Proc. Nat. Acad. Sci., USA* 89:7257–7261) *or the β-actin promoter; and (c) RNA pol III promoters such as cellular tRNA promoters or the promoter from the adenovirus VA1 gene.*

An IL-1α propiece polypeptide expression construct is co-transfected, along with Adenovirus 5 d1309NA (cut with XbaI and ClaI) into HEK 293 cells. Recombinant adenovirus plaques are isolated and expanded by standard techniques. In brief, an adenovirus fraction is collect on a CsCl gradient, purified and dialyzed against physiologic saline with 10 mM Tris pH 8 and 1 mM $MgCl_2$. A concentrated adenovirus preparation (e.g., containing about $10^{12}$ or more viruses in about 100 μl of a carrier solution such as PBS) is administered, for example by injection into and/or around a defined tumor site (e.g., into and around melanoma lesions).

Purification of IL-1α Propiece Polypeptides

IL-1α propiece polypeptides (which polypeptides include native IL-1α propiece (1–118) as well as IL-1α propiece polypeptide variants) may be purified to substantial purity by standard techniques, including selective precipitation with such substances as ammonium sulfate, column chromatography, immunopurification methods, and others (see, e.g., Scopes, *Protein Purification: Principles and Practice*, (1982) Springer-Verlag: New York). For example, IL-1α propiece polypeptides produced by recombinant DNA technology may be purified by a combination of cell lysis (e.g., sonication) and affinity chromatography or immunoprecipitation with a specific antibody to IL-1α propiece polypeptide (e.g., to a native N-terminal IL-1α-pro-piece or a biologically active portion thereof). Where a purified naturally-occurring N-terminal IL-1α propiece is desired, the polypeptide can be purified from any source that produces levels of the polypeptide adequate for purification of a desired amount (e.g., from HL-60 cells).

For fusion products, techniques appropriate to the particular fusion protein may be used to isolate the fusion product and, where desired, release the polypeptide of interest from the non-IL-1α propiece polypeptide amino acid sequences (e.g., digestion of the fusion protein with an appropriate proteolytic enzyme, with further purification by standard protein chemistry techniques, and the like). A purified protein preferably exhibits a single band on an electrophoretic gel. For example, purified human IL-1α propiece (1–118) appears as a single band on reducing SDS-PAGE (0.1% SDS, 0.4% stacking gel, 15% acrylamide resolving gel; molecular mass was determined with reference to the migration of standard protein of known molecular mass and which do not display anomalous migration.

Antibody Production Using IL-α Propiece Polypeptides of the Invention

A number of immunogens may be used to produce antibodies specifically reactive with IL-α propiece polypeptides of the invention. Recombinant protein is the preferred immunogen for production of monoclonal or polyclonal antibodies. Naturally occurring protein may also be used either in pure or impure form. Synthetic peptides based on an amino acid sequence associated with an epitope of a IL-α propiece polypeptide described herein may also used as an immunogen.

Methods of production of polyclonal and monoclonal antibodies are known to those of skill in the art. In brief, an immunogen, preferably a purified IL-α propiece polypeptide, is mixed with an adjuvant and injected into an animal of choice (e.g., a mouse, rat, rabbit, pig, goat, cow, horse, chicken, etc.) at intervals of 1–4 weeks. The immunogen may be conjugated to a carrier protein can be used an immunogen. The animal's immune response to the immunogen preparation is monitored by taking test bleeds and determining the titer of reactivity to the IL-α propiece polypeptide. When appropriately high titers of antibody to the immunogen are obtained, blood is collected from the animal and antisera are prepared. Further fractionation of the antisera to enrich for antibodies reactive to the protein can be done if desired.

Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for cross-reactivity against non-IL-α propiece polypeptide, e.g., using a competitive binding immunoassay.

Monoclonal antibodies may be obtained by various techniques familiar to those skilled in the art. Briefly, spleen cells from an animal immunized with a desired antigen are immortalized, commonly by fusion with a myeloma cell, or by transformation with Epstein Barr Virus, oncogenes, or retroviruses, or by other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells (see, e.g., Huse, et al. (1989) *Science* 246:1275–1281).

Anti-IL-α propiece polypeptide antibodies can be used in a variety of ways, including, but not necessarily limited to, isolation and/or purification of eukaryotic IL-α propiece polypeptides that share antigenic epitopes with, for example, human IL-α propiece (1–118) polypeptide, detection of IL-α propiece polypeptide in during therapy, etc.

Detection of IL-1α Propiece-Encoding Nucleic Acids

IL-α propiece polypeptide expression in a candidate cell can be assessed either qualitatively or quantitatively by any of a variety of means well known in the art. For example, detection of nucleic acid (e.g., mRNA, cDNA) can accomplished by northern analysis, Southern analysis (e.g., mRNA isolation, followed by PCR for cDNA production, followed by Southern analysis), sandwich assays, gel electrophoresis, PCR, radiolabeling, scintillation counting, and affinity chromatography. See, e.g., Sambrook, et al.; *Nucleic Acid Hybridization, A Practical Approach*, Ed. Hames, B. D., et al., IRL Press, (1985); Gall and Pardue, *Proc. Natl. Acad. Sci.*, U.S.A., 63:378–383 (1969); and John et al., *Nature,* 223:582–587 (1969). The selection of a hybridization format is not critical.

Assays involving hybridization can be carried out using nucleic acid probes based on the nucleic acid sequences encoding an IL-1α propiece polypeptide (e.g., SEQ ID NOS:1 and 2) The probes can be full length or less than the full length of the nucleic acid sequence encoding the IL-1α propiece polypeptide. Shorter probes are empirically tested for specificity. ISP. Preferably nucleic acid probes are 20 bases or longer in length. Detection of a hybridization can be accomplished by virtue of a detectable label, according to methods well known in the art. The sensitivity of the hybridization assays may be enhanced through use of a nucleic acid amplification systems, such as PCR.

An alternative means for determining the level of expression of an IL-1α propiece polypeptide is in situ hybridization. In situ hybridization assays are well known and are generally described in Angerer, et al., *Methods Enzymol.,* 152:649–660 (1987).

Detection of IL-α Propiece Polypeptides

IL-1α propiece polypeptide may be detected or quantified by a variety of methods. Preferred methods involve the use of specific antibodies. For example, IL-α propiece polypeptide can be isolated from the candidate cell, and the amount or relative amount of IL-α propiece polypeptide determined by ELISA. Alternatively, the amount of IL-α propiece polypeptide in the sample can be determined by competitive binding assay, or other immunoassay well known in the art. For a description of different formats for binding assays, including competitive binding assays and direct binding assays, see *Basic and Clinical Immunology* 7th Edition (D. Stites and A. Terr ed.) (1991); *Enzyme Immunoassay*, E. T. Maggio, ed., CRC Press, Boca Raton, Fla. (1980); and "Practice and Theory of Enzyme Immunoassays," P. Tijssen, *Laboratory Techniques in Biochemistry and Molecular Biology*, Elsevier Science Publishers B. V. Amsterdam (1985), each of which is incorporated herein by reference.

Identification of Target Cells Susceptible to IL-1α Propiece Polypeptide-Facilitated Apoptosis By Delivery OF IL-α PROPIECE POLYPEPTIDE TO A CANDIDATE CELL Identification of target cells susceptible to IL-1α propiece polypeptide-mediated apoptosis, as well as identification of subjects having a cancer amenable to IL-1α propiece polypeptide-based therapy, can also be accomplished by using a cell-based assay involving 1$ administration of an IL-α propiece polypeptide to a candidate target cells. Candidate target cells can be proxy candidate target cells, which cells are representative of an actual in vivo candidate target cell. Proxy candidate target cells can be commercially available cells, such as those available through the National Cancer Institute (NCI) or the American Type Culture Collection. Susceptibility of the proxy candidate target cell is indicative of susceptibility of a candidate target cell having characteristics similar to the proxy candidate target cell. For example, induction of apoptosis in a commercially-available human melanoma cell (e.g., A2058 human melanoma ATCC CRL 11147), is indicative of the susceptibility of a similar melanoma in a human subject.

Alternatively, candidate target cells can be directly derived from a biopsy of a tumor in a subject who is a candidate for IL-1α propiece polypeptide-based therapy. Methods for culturing cells from a biopsy sample are well known in the art.

The candidate target cells can be tested for susceptibility to IL-1α propiece polypeptide-induced apoptosis by introduction and expression of IL-1α propiece polypeptide-encoding polynucleotides, direct intracellular introduction of an IL-1α propiece polypeptide, and/or extracellular delivery of an IL-1α propiece polypeptide, each of which can be accomplished using methods well known in the art. Preferably, the target cells are screened for susceptibility to apoptosis associated with delivery of extracellular IL-1α propiece-polypeptide and/or expression of IL-1α propiece polypeptide-encoding polynucleotides.

For example, candidate target cells can be screened for susceptibility to apoptosis following exposure to a viral vector comprising an IL-1α propiece polypeptide-encoding nucleic acid. Candidate target cells are grown in culture or plated at 60–80% confluency, or are grown or prepared in suspension at a cell density of from about $10^3$ to about $10^5$ cells/ml, more preferably about $2 \times 10^4$ cells/ml. The viral vector is then added to the cells at a suitable multiplicity of infection (MOI), e.g., about 10 infectious particles per cell.

Apoptosis can be evaluated as described above for the candidate IL-1α propiece polypeptide variant assay. In short, apoptosis can be evaluated by the TUNEL method (which involves 3' end-labeling of cleaved nuclear DNA) (Cohen et al. (1984) *J. Immunol.* 132:38–42) and/or morphological criteria (Cohen et al., supra). Where the screen uses a fusion polypeptide comprising an IL-1α(1–118) polypeptide and a reporter polypeptide (e.g., EGFP), apoptosis can be evaluated by detection of nuclear localization of the reporter polypeptide in fragmented nuclear bodies or apoptotic bodies. For example, where an IL-1α propiece (1–118)-EGFP fusion polypeptide is used, distribution of IL-1α propiece (1–118)-EGFP-associated fluorescence in apoptotic cells was identical to the distribution of DAPI or Hoechst 33342 dyes, which are conventionally used to detect the nuclear DNA changes associated with apoptosis (Cohen et al., supra).

Alternatively or in addition, susceptibility of candidate target cells can be assessed by delivery of an IL-1α propiece polypeptide or polynucleotide to a candidate target cell, and subsequent implantation of the treated cell into an animal model. Inhibition of the ability of treated cells to facilitate tumor growth, production, or metastasis (e.g., relative to tumor production by untreated cells) is indicative of susceptibility of the candidate target cell to IL-1α propiece polypeptide-mediated apoptosis.

Induction of apoptosis in a candidate target cell in the cell-based assay or animal model-based assay described above can be indicative of the susceptibility of the target cell in a subject in vivo. Likewise, the candidate target cell screening assay can also aid in the identification of subjects having a cancer amenable to IL-1α propiece polypeptide-based therapy.

Cancers susceptible to IL-1α propiece polypeptide-based chemotherapy to date include, but are not limited to, skin cancer (e.g., melanoma), colon cancer (e.g., adenocarcinoma), cancers of the central nervous system (e.g., brain tumors, such as grade II and IV glioblastomas, glioblastoma multiforme, astrocytomas, etc.), leukemia (e.g., acute myelogenous leukemia, acute lymphocytic leukemia, acute myelo-monocytic leukemia, pro-myelocytic leukemia, etc.), prostate cancer (e.g., adenocarcinoma), kidney cancer (e.g., renal cell cancer (e.g., clear cell carcinoma, etc.)), lung cancer (e.g., squamous cell, small cell, large cell undifferentiated, adenocarcinoma, etc.), breast cancer (e.g., adenocarcinoma), and ovarian cancer (e.g., adenocarcinoma, etc.).

Induction of Apoptosis in Cancer Cells In Vivo

The polynucleotides and polypeptides of the invention can be used to facilitate induction of apoptosis in cancer cells in a subject having a cancer cell (e.g., a tumor, especially a malignant tumor) susceptible to IL-1α propiece polypeptide-facilitated apoptosis. The formulations of polynucleotides and polypeptides described above can be administered by any route suitable to accomplish expression of introduced IL-1α propiece polypeptide-encoding polynucleotides (e.g., DNA-based polypeptide delivery), direct intracellular polypeptide delivery, and/or extracellular polypeptide delivery.

Formulations suitable for administration of the polynucleotides and polypeptides of the invention include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials. Injection solutions and suspensions can be prepared from sterile powders, granules, and tablets of the kind previously described. The precise formulation used and/or the formulation preferred will vary with a variety of factors including, but not limited to, the mode of IL-1α propiece polypeptide delivery (e.g., DNA-based IL-1α propiece polypeptide delivery or IL-1α propiece polypeptide delivery), the route of administration, and other factors that will be readily apparent to the ordinarily skilled artisan.

Administration of polynucleotides and polypeptides of IL-1α propiece polypeptide The pharmaceutical compositions of the invention comprising IL-1α propiece polynucleotides and/or polypeptides are preferably administered topically or parenterally, i.e., intraarticularly, intravenously, intraperitoneally, subcutaneously, or intramuscularly. More preferably, the pharmaceutical compositions are administered intravenously or intraperitoneally by a bolus injection (see, e.g., U.S. Pat. No. 5,286,634; Straubringer et al., (1983) *Meth Enzymol* 101:512–527; Mannion et al. (1988) *Biotechniques* 6:682–690; Nicolau et al. (1989) *Crit. Rev. Ther. Drug Carrier Syst.* 6:239–271, and Behr (1993) *Acc. Chem. Res.* 26:274–278.

Still other methods of administering therapeutics are described in, for example, U.S. Pat. Nos. 3,993,754; 4,145,410; 4,235,871; 4,224,179; 4,522,803; and 4,588,578.

In preferred embodiments, the pharmaceutical preparations may be contacted with the target tissue by direct application of the preparation to the tissue. The application may accomplished by topical administration or by "open" or "closed" procedures. By "topical", it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the preparations may be administered through endoscopic devices. Preferably, where a closed procedure is used, the formulation is injected directly into the tumor site.

The pharmaceutical compositions of the invention can also be administered in an aerosol inhaled into the lungs (see, Brigham, et al. (1989) *Am. J. Sci.*, 298(4):278–281) or by direct injection at the site of disease (Culver, *Human Gene Therapy*, MaryAnn Liebert, Inc., Publishers, New York. pp. 70–71 (1994)).

Effective doses of the pharmaceutical compositions of the present invention will vary depending upon many different factors, including the form of the composition administered (e.g., polypeptide or polynucleotide, viral vector or non-viral vector, etc.), the means of administration, target site, physiological state of the patient, and other medicants administered. Thus, treatment dosages will need to be titrated to optimize safety and efficacy; such can be readily determined and are routine to the ordinarily skilled artisan. In determining the effective amount of polypeptide or polynucleotide to be administered, the physician evaluates, for example, the particular composition used, the disease state being diagnosed; the age, weight, and condition of the patient, formulation toxicities, disease progression, production of anti-vector antibodies, and the like. The dose will also be determined by the existence, nature, and extent of any adverse side-effects that accompany the administration of a particular formulation. Doses ranging from about 10 ng to 1 g, 100 ng to 100 mg, 1 µg to 10 mg, or 30–300 µg polypeptide or polynucleotide per patient are typical. Doses generally range between about 0.01 and about 50 mg polypeptide or polynucleotide per kilogram of body weight; preferably between about 0.1 and about 5 mg/kg polypeptide or polynucleotide of body weight or, where a viral vector is used, about $10^8$–$10^{10}$ or $10^{12}$ particles per injection. In general, where a polynucleotide is delivered, the dose equivalent of naked nucleic acid is from about 1 µg to 100 µg for a typical 70 kilogram patient, and doses of vectors which include a retroviral particle are calculated to yield an equivalent amount of inhibitor nucleic acid.

The precise route of administration, formulation, delivery system, and dosage will vary according to the IL-1α propiece polypeptide-based therapy selected, e.g., DNA-based IL-1α propiece polypeptide delivery, direct intracellular IL-1α propiece polypeptide delivery, or extracellular IL-1α propiece polypeptide delivery. For example, in the case of virus-based delivery the clinician may choose to administer a quantity of viral particles sufficient to provide an MOI of about or greater than 10 infectious particles per cell estimated to be associated with a target tumor. Where IL-α propiece polypeptide is delivered using a liposome of vesicle, the clinician may choose to administer a quantity of the formulation sufficient to provide a concentration equal to or greater than about 1–3 µg/ml in the region of the tumor.

DNA-Based Delivery of IL-1α Propiece Polypeptide

Delivery of IL-1α propiece polypeptide to a target cell can be accomplished by introducing IL-1α propiece polypeptide-encoding polynucleotides into a target cell in vivo, using methods known to those of ordinary skill in the art as discussed above (see, e.g., Zhu, et al. (1993) *Science* 261:209–211 (intravenous delivery of DNA-containing DOTMA-DOPE complexes), Hyde et al. (1993) *Nature* 362:250–256 (delivery of cystic fibrosis transmembrane conductance regulator (CFTR) gene to the lung using liposomes); Brigham et al. (1989) *Am. J. Med. Sci.* 298:278–281 (in vivo lung transfection)). In vivo gene transfer may be practiced in a variety of hosts. Preferred hosts include mammalian species, such as humans, non-human primates, dogs, cats, cattle, horses, sheep, and the like. DNA-based IL-1α propiece polypeptide delivery is advantageous in that, unlike soluble chemotherapeutic agents, the amount of IL-1α propiece polypeptide delivered to a target cell can be controlled through regulation of expression of the IL-1α propiece polypeptide-encoding polynucleotide.

Direct Intracellular Delivery of IL-1α Propiece Polypeptide

IL-1α propiece polypeptides of the invention can be delivered to a target cell by direct intracellular delivery, e.g., by introduction of a IL-1α propiece polypeptide into the target cell cytoplasm. Methods for accomplishing direct intracellular deliver include contacting a target cell with a liposomal formulation of an IL-1α propiece polypeptide (see, e.g., U.S. Pat. Nos. 4,394,438; 5,459,127), by microinjection (e.g., stereotactic injection, as into a brain tumor (see e.g., Zlokovic et al. (1997) *Neurosurgery* 40:805–12)), and other methods well known in the art.

Delivery of IL-1α Propiece Polypeptide by Extracellular Contact

IL-1α propiece polypeptides of the invention can also be delivered to target cells by contacting the IL-1α propiece polypeptides with the surface of a target cell, i.e., by delivering the IL-1α propiece polypeptide extracellularly. Methods for extracellular delivery suitable for IL-1α propiece polypeptide delivery include delivery methods suitable for administration of polypeptides to a subject, e.g., parenteral injection and topical administration. Of particular interest is the administration of an IL-1α propiece polypeptide into and/or around the site of a tumor comprising target cells susceptible to IL-1α propiece polypeptide-induced apoptosis.

IL-α propiece polypeptides of the invention may be incorporated into liposomes. Liposomes suitable for use in the invention may be of conventional phospholipid:cholesterol composition, or may contain incorporated proteins serving as affinity ligands for the tumor target. Affinity ligands can include, but are not necessarily limited to, polypeptide ligands (e.g., peptide hormones (e.g., EGFP), and fragments thereof retaining receptor binding activity, etc.), antibodies (or fragments thereof) having binding specificity for surface determinants of a targeted cell (e.g., a tumor antigen), etc. The liposome-propiece material may be delivered in any of a variety of ways, e.g., by infiltration into the tumor by local injection or by introduction into a branch of an artery supplying blood to the tumor.

Alternatively, affinity ligands for delivery to a selected target cell may be coupled directly to the IL-α propiece polypeptide, e.g., through a covalent linkage or through a high affinity association such as that obtained when biotin and avidin are coupled to separate polypeptides which then associate by virtue of the avidin-biotin association.

Assessment of IL-1α Propiece Polypeptide-Based Chemotherapy

Following delivery of an IL-1α propiece polypeptide to a subject having cancer, the subject's progress and the efficacy of IL-1α propiece polypeptide-based chemotherapy can be assessed by parameters and methods that will be readily apparent to the ordinarily skilled artisan. For example, IL-1α propiece polypeptide-based chemotherapy can be assessed by observation of the subject of signs of tumor regression using, for example and where appropriate, imaging techniques that are capable of visualizing cancerous tissues (e.g., MRI), biopsies, methods for assessing metabolites produced by the cancer tissue or affected tissue in question, the subjective well-being of the patient, etc.

For example, the pharmaceutical compositions of the invention can be provided in the form of a viral vector and administered by infusion. Prior to infusion, blood samples are obtained and saved for analysis. Approximately $10^8$ and $10^{12}$ viral particles carrying an IL-1α propiece polypeptide-encoding polynucleotide are infused intra-arterially over 60–200 minutes. Vital signs and oxygen saturation by pulse oximetry are closely monitored. Blood samples are obtained 5 minutes and 1 hour following infusion and saved for subsequent analysis. At the physician's discretion, reinfusion can be repeated every month (since IL-1α propiece polypeptide is non-immunogenic) for a total of 4 to 6 treatments in a one year period. After the first treatment, infusions can be performed on a outpatient basis at the discretion of the clinician. If the reinfusion is given as an outpatient, the participant is monitored for at least 4, and preferably 8 hours following the therapy.

If a patient undergoing infusion develops fevers, chills, or muscle aches, he/she receives the appropriate dose of aspirin, ibuprofen or acetaminophen. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Vector infusion is slowed or discontinued depending upon the severity of the reaction.

Detection of Apoptosis by Detection of Cell Growth Inhibition

Efficacy of IL-1α propiece polypeptide-based chemotherapy can also be assessed by detection of apoptosis-associated cell growth inhibition. "Inhibiting cell growth" or "inhibiting tumor growth" generally means that the rate of increase in mass, size, number and/or the metabolism of treated cells and/or tumors is slower relative to untreated cells and/or tumors. The growth of a cancerous cell or tumor is said to be "inhibited" by IL-1α propiece polypeptide-based treatment if, when assayed by means such as radioisotope incorporation into the cells, the treated cells increase in number at a rate that is less than the proliferation rate of untreated control cells, and preferably less than about 50% of the untreated cell proliferation rate. More preferably, the proliferation rate is inhibited by at least 80%. If growth is assayed by a means such as plating in methylcellulose, cell growth is "inhibited" if treated cells give rise to a number of colonies less than a number of colonies that result from plating approximately the same number of untreated cells. Preferably, the number of colonies that arise from treated cells is less than about 70% of the number from untreated cells. More preferably, the number of colonies is decreased by at least 50%.

"Inhibition of cell growth" also encompasses zero growth and death of tumor cells and/or tumor eradication. When measured in vivo, "inhibition of tumor growth" means that a treated tumor is smaller (e.g., smaller in diameter and/or mass) or, when tumor growth is associated with metastasis, gives rise to fewer tumors growths as compared to untreated controls.

Inhibition can be evaluated by any accepted method of measuring whether growth or size of the tumor and/or increase in the number of cancerous or tumor cells has been slowed, stopped, or reversed. This includes direct observation and indirect evaluation such as subjective symptoms or objective signs. The clinician may notice a decrease in tumor size or tumor burden (number of tumors) based on physical exam, laboratory parameters, tumor markers, or radiographic findings. Alternatively, if the mammal is human, the patient may note improved vigor or vitality or decreased pain as subjective symptoms of improvement or response to therapy. Some laboratory signs that the clinician may observe for response to therapy include normalization of tests such as white blood cell count, red blood cell count, platelet count, erythrocyte sedimentation rate, and various enzyme levels such as transaminases and hydrogenases. Additionally, the clinician may observe a decrease in a detectable tumor marker such as prostatic specific antigen (PSA) or chorio embryonic antigen (CEA). Alternatively, other tests can be used to evaluate objective improvement such as sonograms, 1: computerized axial tomography scans, nuclear magnetic resonance scans and positron emission testing.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

Production of DNA Encoding Native IL-1α(1–118)

IL-1α cDNA was obtained by first treating human HL-60 cells with 0.1 μM phorbol myristate acetate for 24 hrs to induce IL-1 production. Total mRNA was prepared using standard techniques, and IL-1α cDNAs obtained from poly-A mRNA by reverse transcription using oligo-dT and MLV reverse transcriptase according to standard protocols and a commercially available kit (Superscript Reverse Transcriptase, BRL/Life Sciences, Gaithersberg, Md.). The nucleic acid sequence (SEQ ID NO:1) encoding human IL-1α pro-piece (1–118) (IL-1α propiece (1–118) (SEQ ID NO:2)) was specifically isolated through 38 cycles of PCR using Taq polymerase under standard conditions as described by the manufacturer, and using a Perkin Elmer 9600 PCR machine. The annealing temperature was 56° C. The 5' primer used in PCR, 5cagtaCTCGAGCGGCCGC-CACCatggccaaagttccagacatg (SEQ ID NO:3), contains (from 5' to 3') a XhoI and a NotI site, a consensus Kozak sequence (GCCACC), a start codon (ATG), and the first 19 nucleotides of human IL-1α cDNA that follow the start codon. The Kozak sequences incorporated into the 5' primer served to place the primer immediately 5' of the ATG translation initiation codon. The 3' primer used in PCR, 5gactaAGATCTCTAGATTAgaagctaaaaggtgctgac (SEQ ID NO:4), contains (from 5' to 3') an XbaI site, the inverse complement of an introduced stop codon (TTA), and the inverse complement of the cDNA of the IL-1α pro-piece. The restriction sites incorporated into the primers allowed for ligation of the resulting amplified PCR product into convenient expression constructs.

The PCR reaction products were precipitated and resolved on a 1.5% low melting temperature agarose gel. The amplified human IL-1α pro-piece-containing PCR product was excised from the gel, digested with XhoI and XbaI and cloned into commercially available expression vectors, such as pcDNA1-AMP (Invitrogen).

Example 2

Production of IL-1α Propiece (1–118)-EGFP Fusion Protein

In order to facilitate detection of IL-1α propiece (1–118) expression and induction of apoptosis, a fusion protein between IL-1α propiece (1–118) and a fluorescent reporter molecule, green fluorescent protein (GFP), was produced. Specifically, a variant of the *Aequoria Victoria* GFP variant, enhanced green fluorescent protein (EGFP), was used in fusion protein production (CLONTECH Laboratories, Inc., 1020 East Meadow Circle, Palo Alto, Calif. 94303). The IL-1α propiece (1–118) cDNA sequence was fused in-frame by insertion of the IL-1αa propiece (1–118)-encoding cDNA into the SalI-BamHI site of plasmid pEGFP-N1 (GenBank Accession # U55762). The resulting cDNA insert is presented in the Sequence Listing as SEQ ID NO:5, where nucleotides 1–354 encode IL-1α propiece (1–118), nucleotides 355–375 encode a linker polypeptide, and nucleotides 376–1092 encode EGFP. The translated fusion protein is presented in the Sequence Listing as SEQ ID NO:6. The IL-1α propiece (1–118) portion is present as amino acid residues 1–118, the linker polypeptide is positioned at amino acid residues 119–125, and the EGFP portion is present as amino acid residues 126–364.

To demonstrate that the fusion protein consisting of IL-1α (1–118) fused to the coding sequence of EGFP possessed apoptosis-inducing properties substantially similar to the IL-1α parent molecule, 293 cells were transfected with plasmid vectors expressing either IL-1α or the IL-1α-EGFP fusion protein. Approximately $5 \times 10^6$ 293 cells in 100 mm dishes were transfected with 10 µg of plasmid DNA using the calcium-phosphate method. The plasmids used were pCDNA-IL-1α (CMV enhancer/promoter, IL-1α coding sequence) or pEGFP-N1-IL-1α (CMV enhancer/promoter, IL-1α-EGFP coding sequence). Apoptosis was evaluated 24 hrs after transfection.

In the IL-1 transfected cells, TUNEL and DAPI staining revealed approximately 90% apoptosis. The IL-1α-EGFP vector transfected cells were evaluated by fluorescence microscopy with observation of typical nuclear aggregation of the EGFP marker as an indication of apoptosis. Expression of the IL-1α(1–118)-EGFP also produced apoptosis in approximately 90% apoptosis. Therefore, presence of the reporter polypeptide does not substantially affect the ability of the polypeptide to induce apoptosis. The distribution of EGFP signal in cells expressing IL-1α(1–118)-EGFP was identical to the distribution of DAPI or Hoechst 33342 dyes, which are conventionally used to detect the nuclear DNA changes associated with apoptosis (Cohen et al., supra). The presence of IL-1α propiece (1–118)-EGFP-associated fluorescence in fragmented nuclear bodies or apoptotic bodies is indicative of induction of apoptosis in the target cell.

Example 3

Production of IL-1α Propiece (1–118) Variants

Variants of the IL-1α propiece (1–118)-EGFP fusion were produced by site-specific mutagenesis according to methods well known in the art. The IL-1α propiece (1–118)-EGFP construct described in Example 2 above served as the parent molecule. Where the IL-1α propiece (1–118) variant comprises the first N-terminal amino acids of IL-1α propiece (1–118) (SEQ ID NO:2), the normal methionine initiation codon of IL-1α propiece (1–118) was used. Where the IL-1α propiece (1–118) variant were N-terminally truncated relative to IL-1α propiece (1–118) (SEQ ID NO:2) (i.e., the variant polypeptide began with at an amino acid residue other than residue 1 of SEQ ID NO:2), an ATG initiation methionine codon was inserted so as to reconstruct a coding sequence. The last codon of the IL-1α variants were followed by either a termination codon or, in the case of fusion proteins with EGFP, the last codon was placed in the correct reading frame so as to produce a complete fusion protein.

Figure 2:
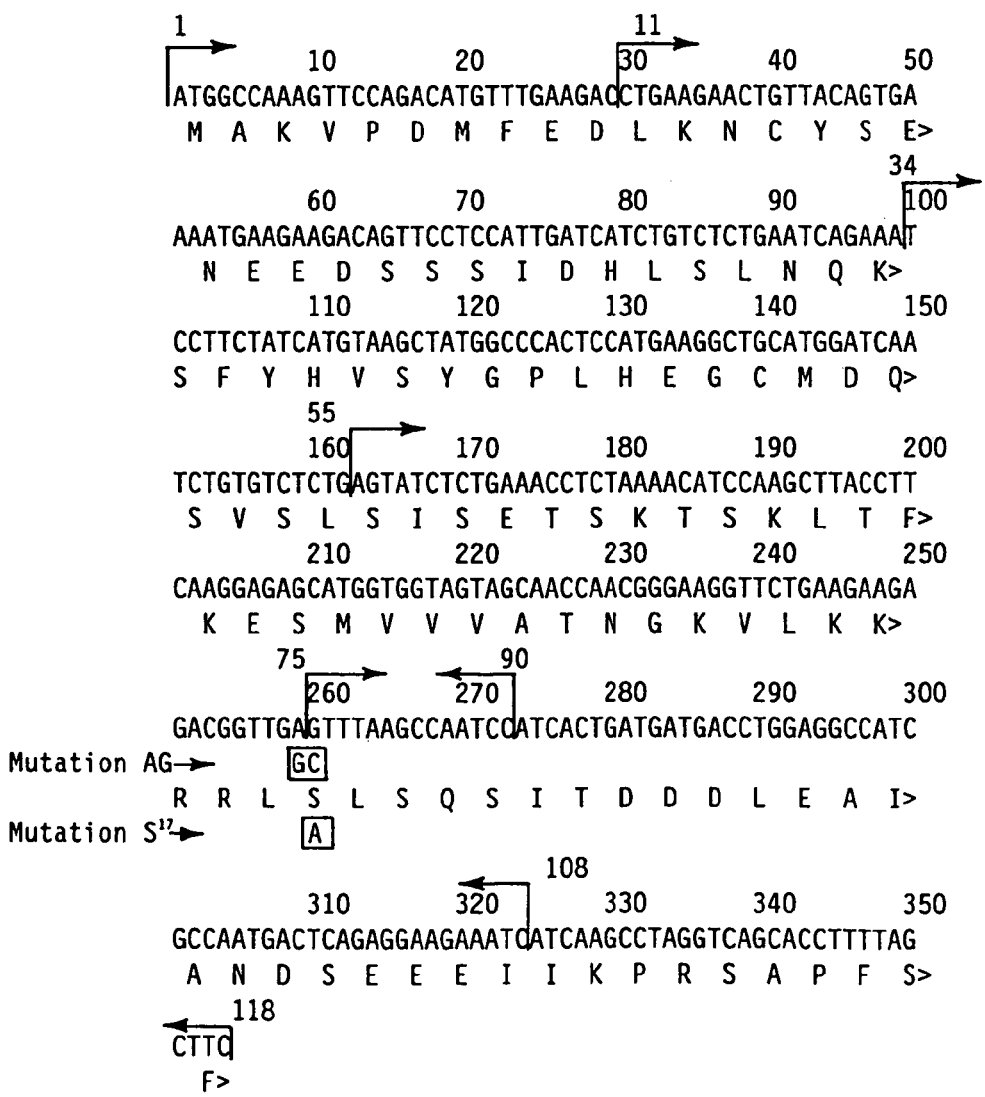
FIG. 2 is a schematic showing the nucleotide and amino acid sequences of native human IL-1α propiece (1–118) and the portions relevant in production of exemplary IL-1α propiece (1–118) variants

A summary of the IL-1α propiece (1–118) variants produced is provided in Table 1. The IL-1α (1–118) variants indicated by an asterisk were produced both as EGFP fusions proteins and as independent polypeptides (i.e., without the EGFP polypeptide). FIG. 2 is a schematic showing the positions of the IL-1α propiece (1–118) variants relative to native IL-1α propiece (1–118).

TABLE 1

IL-1α(1–118) Variants

| Name | Description |
|---|---|
| IL-1α(1–118)-EGFP | IL-1α(1–118) fused to EGFP |
| IL-1α(11–118) | IL-1α 11–118; anionic amino acids in helix 1 removed |
| IL-1α(1–90) | IL-1α(1–90); anionic residues in helix 3 removed |
| IL-1α(11–90) | IL-1α(11–90) |
| IL-1α(75–118) | IL-1α(75–118); contains only helix 3 |
| IL-1α(34–118) | IL-1α(34–118); helix 1 removed in its entirety |
| IL-1α(1–118)S87A | IL-1α(1–118), Ser 87 to Ala point mutation, removed phosphorylation site |
| IL-1α(55–118) | IL-1α(55–118), first helix and half of second helix removed. |
| IL-1α(66–118) | IL-1α(66–118); 3 basic residues between 55 and 74 removed |
| IL-1α(1–108) | IL-1α(1–108); acidic residues around 95 and 107 restored |
| IL-1α(1–118)-ZIP-EGFP | Leucine zipper domain (L-ZIP) inserted between IL-1α(1–118) and EGFP in fusion protein construct via BamHI and AgeI sites |
| NLS-IL-1α(86–118) | SV40 nuclear localization signal sequence (NLS) added to IL-1α(86–118) |
| NLS-IL-1α(75–118) | SV40 NLS added to IL-1α(75–118) |
| IL-1α(55–108) | IL-1α(55–108), first helix and half of second helix removed, last 10 AA removed |
| IL-1α(75–108) | SV40 NLS added to IL-1α(75–108) |
| IL-1α propiece (1–108)-ZIP-EGFP | L-ZIP inserted between IL-1α(1–108) and EGFP in fusion protein construct via BamHI and AgeI sites |
| IL-1α(55–108)-ZIP-EGFP | L-ZIP inserted between IL-1α(55–108) and EGFP in fusion protein construct via BamHI and AgeI sites |
| NLS-IL-1α(75–118)-ZIP | LZIP inserted between NLS IL-1α(75–118) and EGFP via Bam HI and AgeI sites |
| NLS-IL-1α(75–108)-ZIP | LZIP inserted between NLS IL-1α(75–108) and EGFP via Bam HI and AgeI sites |
| pEGFP-N1-IL1α(1–118)-musER | Tamoxifen-sensitive mouse estrogen receptor (G525 -> R) hormone binding domain (musER) to C-terminus of IL-1α(1–118)-EGFP fusion. Mutation in musER renders hormone binding domain insensitive to estrogens but sensitive to binding of the estrogen analog 4-OH tamoxifen. |

The amino acid sequences of NLS-IL-1α(75–118) (SEQ ID NO:21), NLS-IL-1α(75–108) (SEQ ID NO:22), NLS-IL-1α(75–108)-ZIP (SEQ ID NO:23), NLS-IL-1α(75–118)-ZIP (SEQ ID NO: 24), IL-1α(1–118)-ZIP (SEQ ID NO:25), IL-1α(1–108)-ZIP (SEQ ID NO:26), and IL-1α(55–108)-ZIP (SEQ ID NO:27) are provided in the Sequence Listing.

Example 4

Vectors for Expression of IL-1α Propiece (1–118) and Variants Thereof

Plasmid vectors. All plasmid vectors used in transfection studies were composed of standard plasmid backbones, a CMV enhancer promoter operably linked to a coding sequence For IL-1α propiece (1–118) or a variant thereof, followed by a polyadenylation signal derived from the SV40 virus. In some cases an intron and splice sequence were placed between the CMV enhancer/promoter and the coding sequence. The coding sequence included a Kozak sequence (ccacc) positioned immediately 5' to the ATG initiation codon. Plasmid vectors were introduced into cells by a variety of methods appropriate to a given cell types including calcium-phosphate transfection, electroporation, or cationic liposome-mediated transfection (e.g., Lipofection). Exemplary commercial vectors used herein include pCDNA (Invitrogen) and pEGFP-N1 (Clontech).

Retroviral vectors. Retroviral vectors used were as described in Finer et al. (1994) *Blood* 83(1):43–50. These vectors used a modified Moloney murine sarcoma virus promoter. Instead of the murine coat proteins, the viruses were pseudotyped with the coat protein of vesicular stomatitis virus (VSV G) as described in Ory et al. (1996) *Proc. Natl. Acad. Sci. USA* 93(21):11400–6. Retroviral preparation were applied to proliferating cells in culture medium to allow infection. Cells were evaluated about 24 to 96 hrs later. Polybrene (8 μg/ml) was added to some infections to enhance efficiency of retroviral infection.

Sindbis viral vectors. Sindbis viral vectors expressing either the control EGFP construct or IL-1α propiece (1–118)-EGFP were prepared using standard methods and a kit from Invitrogen. The general method for Sindbis viral vector production is described in Altman-Hamamdzic (1997) *Gene Therap.* 4(8):815–22. Vector titers of approximately $10^7$–$10^8$ viral particles/ml were obtained.

Example 5

Induction of Apoptosis by Expression of IL-1α Propiece (1–118) Variants

The ability of the IL-1α propiece (1–118) variants described above to undergo nuclear localization and to induce apoptosis was tested by transient expression in 293 human kidney cells as described in Example 2 above. 293 cells were used since this cell line was convenient and had proved susceptible to IL-1α propiece (1–118)-induced apoptosis. Thus, the ability of an IL-1α propiece (1–118)-EGFP variant to induce apoptosis in 293 cells served as an initial screen for those variants that will likely also induce apoptosis in cancer cells. Nuclear localization and induction of apoptosis were observed by fluorescence microscopy and scored by direct cell counting under fluorescence microscopy. The results are summarized in Table 2. Results denoted by dashes (—) indicates that there was no detectable nuclear localization or induction of apoptosis. Results were scored on a semi-quantitative scale, with IL-1α propiece polypeptide set at 4+.

TABLE 2

Nuclear localization and apoptosis induction by IL-1α propiece (1–118) variants

| Name | Nuclear Localization | Apoptosis Induction |
|---|---|---|
| IL-1α propiece (1–118)-EGFP | 4+ | 4+ |
| IL-1α(11–118) | 4+ | 4+ |
| IL-1α(1–90) | 1+ | — |
| IL-1α(11–90) | — | — |
| IL-1α(75–118) | 1+ | — |
| IL-1α(34–118) | 4+ | 4++ |
| IL-1α propiece (1–118)S87A | 4+ | 3–4+ |
| IL-1α propiece (55–108)-ZIP-EGFP | 4+ | 4+ |
| NLS-IL-1α(75–108)-ZIP | 4+ | 4+** |
| IL-1α(55–118) | 4+ | 3–4+ |
| IL-1α(1–108) | 4+ | 4+ |
| IL-1α propiece (1–118)-ZIP-EGFP | 4+ | 4+ |
| NLS-IL-1α(86–118) | 4+ | — |
| NLS-IL-1α(75–118) | 4+ | 4+** |
| NLS IL-1α(75–108) | 4+ | 4+** |
| pEGFP-N1-IL1α(1–118)-musER | 4+ | 4+* |
| IL-1α(55–108) | 4+ | 4+ |
| NLS-IL-1α(75–118)-ZIP | 4+ | 4+** |

*Observation of apoptosis was dependent upon addition of 10 nM 4-OH tamoxifen (an estrogen analog that binds the musER portion of the fusion protein).
**Apoptosis is delayed until 72 hours.

These data show that much of the N-terminal portion of IL-1α propiece (1–118) is not necessary to effect apoptosis, since the variants containing only amino acid residues 1–108, 11–118, 34–118, 55–118, 55–108, 75–118, and 75–108 effectively induced apoptosis. The anionic portion of the terminal helix of residues 90–108 or 90–118 are apparently required for apoptosis-inducing activity since the IL-1α(1–90) variant did not effect detectable apoptosis as measured in the apoptosis assay. The data also show that an intact terminal helix of residues 75–118 is required but not sufficient, and that portions of helix 2 are required.

Moreover, the nuclear localization signal sequence (NLS) KKRR at 82 is not an independent NLS in this context. The serine residue at position 87 following KKRR is not necessary for killing. This result was particularly surprising since Ser87 is a putative phosphorylation site and was thought important for biological activity. Amino acid residues 55–74 are apparently required for nuclear localization and for killing, since IL-1α(75–118) was not detected in the nucleus and did not kill cells while IL-1α(55–118) exhibited both nuclear localization and effected killing.

Finally, inclusion of a heterologous NLS was effective in delivering IL-1α propiece polypeptides to the nucleus and allowing the polypeptide to effect apoptosis. This effect was particularly interesting when the heterologous NLS was fused to the IL-1α(75–118) polypeptide. When used alone, the IL-1α(75–118) polypeptide was not transported to the nucleus in very high amounts, and no apoptotic effect was observed. Addition of the heterologous NLS facilitated transport of the IL-1α(75–118) polypeptide to the nucleus, where the IL-1α(75–118) polypeptide efficiently effected apoptosis. This observation suggests that the NLS and apoptotic-inducing activity of the IL-1α propiece polypeptide are separable, and that heterologous NLS can substitute for the NLS present in IL-1α propiece polypeptide.

In summary, these data show that the minimum region of the IL-1α propiece (1–118) required to accomplish both nuclear localization and killing is a region spanning or contained within amino acid residues 55–108, while the amino acid residues spanning 75–108 are necessary for apoptosis induction. Equivalents of either or both of these amino acid sequences that retain activity in either nuclear localization, apoptosis-induction, or both can be readily produced.

To further confirm that activity of the apoptosis-inducing polypeptides, constructs encoding the variants IL-1α (11–118), IL-1α(34–118), IL-1α(55–118), and IL-1α propiece (1–118)S87α were prepared without the reporter EGFP fusion polypeptide, and the ability of these variants to induce apoptosis in 293 cells tested. Each of these polypeptides induced apoptosis at levels similar to those observed when the polypeptides were part of the EGFP fusion protein.

Example 6

Induction of Apoptosis in Malignant Melanoma Cells by Transient, Plasmid-Based Expression of IL-1α(1–118)

The susceptibility of malignant melanoma cells to apoptosis induced by IL-1αX propiece (1–118) was tested in several melanoma cell types: human melanoma WM 266-4 (ATCC CRL-1676); human malignant melanoma A-375 (ATCC CRL-1619); human malignant, melanoma A2058 (ATCC CRL-11147); human malignant melanoma SK-MEL-31 (ATCC HTB-73); human malignant melanoma RPMI-7591 ATCC HTB-66 (metastasis to lymph node). Two primary melanoma isolates, MZWR (from a metastasis from a right axillary melanoma from a 35 years old Caucasian male) and MZVA (a metastatic melanoma from right arm of a 69 year old Caucasian female) were also tested. In addition, human chronic myelogenous leukemia K-562 cells (ATCC CCL-243), and 293 human kidney cells (ATCC CRL-1573) (transformed primary embryonal cell) were tested. Normal human primary dermal fibroblasts and Rat-1 fibroblasts served as controls. All melanoma cell lines were metastatic on the basis of their isolation from metastases or metastatic nodules.

A transient expression strategy was used in order to evaluate induction of IL-1α propiece (1–118)-mediated apoptosis without artifacts associated with prolonged selection. The expression vector encoding the IL-α(1–118)-EGFP fusion protein described in Example 2 above was used in order to facilitate identification of those cells expressing the IL-1α(1–118). Cells were transiently transfected by the method optimal for the cell being tested (either CaPO$_4$ or Lipofectin). Expression of IL-1α(1–118) and induction of apoptosis were examined using a fluorescence microscope at 24 hrs and 48 hrs post-transfection. A minimum of approximately 100 cells, which displayed characteristic EGFP fluorescence, were evaluated by fluorescence microscopy. Apoptosis was scored as nuclear fragmentation, marked apoptotic bodies, and cytoplasmic boiling. The characteristics of nuclear fragmentation were particularly visible when IL-1α(1–118)-EGFP condensed in apoptotic bodies.

TABLE 3

Induction of apoptosis by transient, plasmid-based expression in melanoma cells

| CELL LINE | % Apoptotic at 24 hrs post transfection | % Apoptotic at 48 hrs post transfection |
|---|---|---|
| Normal Human primary Dermal Fibroblasts | 9% | |
| RPMI7951 Human Melanoma (ATCC HTB66) | 61% | 100% |
| WM266-4 Human Melanoma (ATCC CRL1676) | 56% | |
| A2058 Human Melanoma (ATCC CCL 11147) | 86% | 100% |
| A375 Human Melanoma (ATCC CRL 1619) | 67% | 100% |
| SK-MEL31 Human Melanoma (ATCC HTB 73) | 75% | |
| Primary Isolate Human Melanoma (MZVA) | 75% | |
| Primary Isolate Human Melanoma (MZWR) | 75% | |
| 293 Human Kidney Cells (ATTC CRL 1573) (transformed) | 71% | 90% |
| Rat-1 Fibroblasts (immortalized) | 14% | 17% |

While normal human primary dermal fibroblasts did not exhibit elevated levels of apoptosis, all the melanoma cell lines tested were susceptible to apoptosis following IL-1α (1–118) expression. Rat-1 fibroblasts (an immortalized non-malignant cell line) were only minimally susceptible to IL-1α (1–118) apoptosis. In contrast, 293 human kidney cells (which are capable of forming tumors when introduced into mice and are thus malignant by this criteria), were highly susceptible to apoptosis induced by IL-1α(1–118).

These data show that the IL-1α propiece (1–118) polypeptide induces apoptosis in human melanoma cells, but does not substantially induce apoptosis in normal human cells.

Example 7

Inhibition of Melanoma Tumor Growth by Expression of IL-1α Propiece (1–118)

A375 melanoma cells were grown to 80% confluency in RPMI-1640 medium containing 5% fetal bovine serum. The cells were treated with retroviruses carrying either an EGFP-encoding polynucleotide (control) or native human IL-1α propiece (1–118) polypeptide-encoding polynucleotide fused in one continuous open reading frame to the coding sequence of EGFP. The retroviruses were as described in Example 4 and were pseudotyped with VSV G.

Approximately $5 \times 10^8$ viruses were applied to approximately $1 \times 10^7$ dividing A375 cells in a 150 cm$^2$ tissue culture flask in a final volume of 18 ml. At 24 hrs post-infection, the cells were trypsinized to remove them from the culture flask, centrifuged, and suspended in phosphate buffered saline (PBS) at approximately $10^6$ cells/ml. A volume of 0.1 ml of the cell suspension was injected subcutaneously into the flanks of female, 7 week-old, immunodeficient mice (nude mice). Tumor formation in the flanks was measured with calipers and tumor volume calculated by the formula:

Volume=(longest dimension×shortest dimension$^2$)/2.

Figure 3:
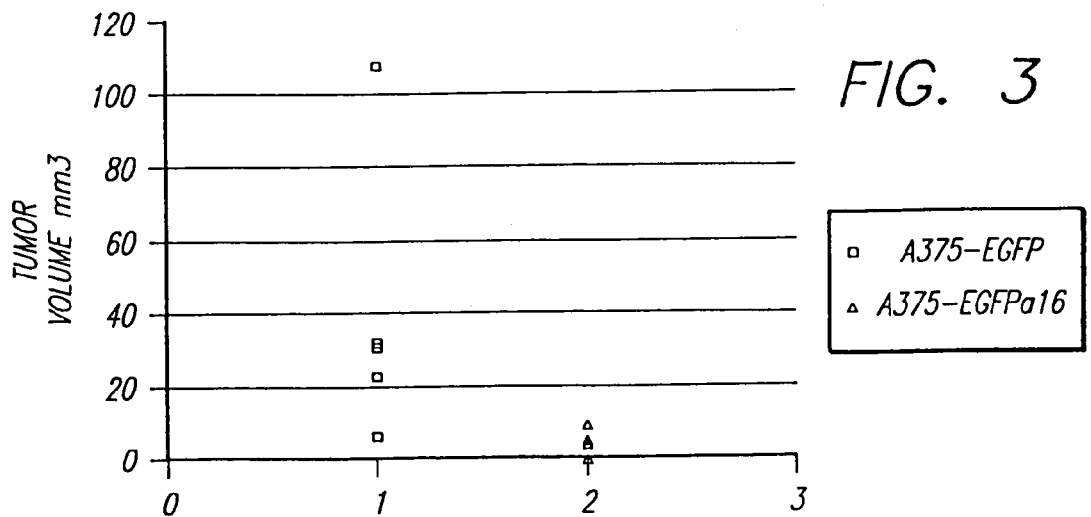
FIG. 3 is a graph showing the volume of tumors formed at day 13 after implantation of IL-1α propiece (1–118)-treated and EGFP-treated melanoma cells in nude mice.
Figure 4:
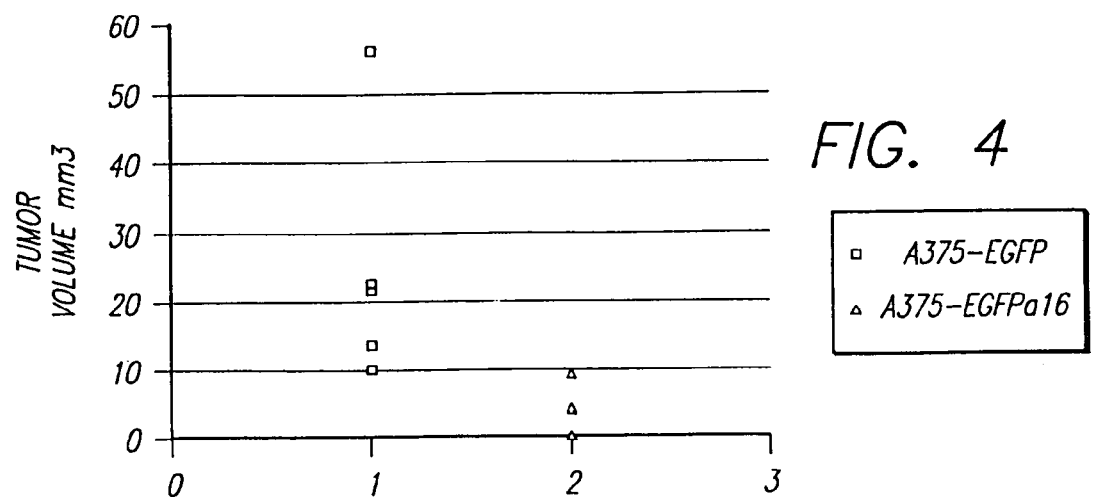
FIG. 4 is a graph showing the volume of tumors formed at day 16 after implantation of IL-1α propiece (1–118)-treated and EGFP-treated melanoma cells in nude mice.
Figure 5:
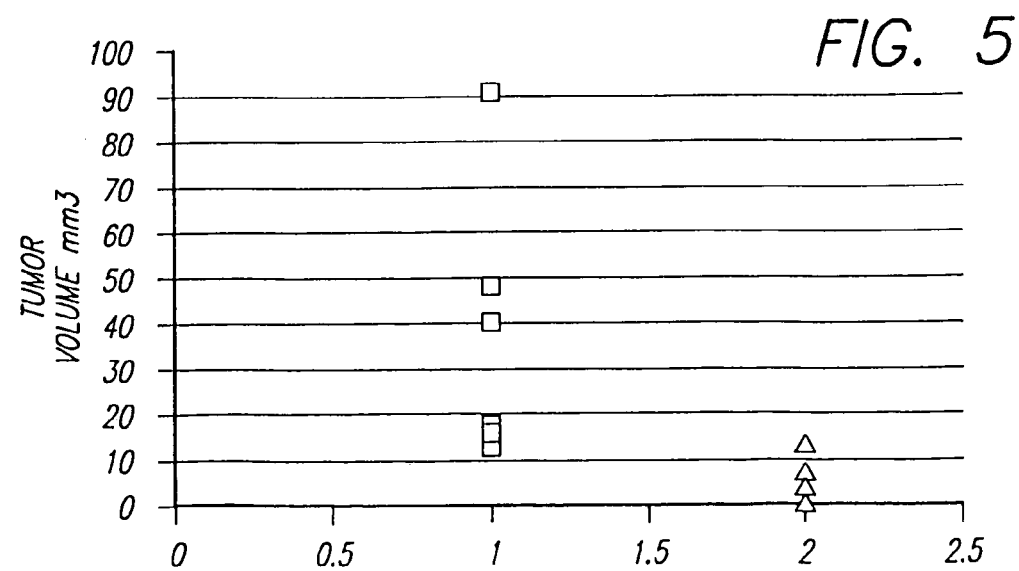
FIG. 5 is a graph showing the volume of tumors formed at day 19 after implantation of IL-1α propiece (1–118)-treated and EGFP-treated melanoma cells in nude mice.

Measurements of mean tumor volume in each of 8 mice per construct were taken at days 13, 16, and 19 post-injection. The results are presented in FIGS. 3–5 (tumor volume at days 13, 16, and 19, respectively) and are summarized in Table 4 below.

TABLE 4

Tumor volume associated with melanoma cells expressing IL-1α propiece (1–118)-EGFP or EGFP

| Construct | Day 13 volume | Day 16 volume | Day 19 volume |
|---|---|---|---|
| EGFP (control) | 22 mm$^3$ | 20 mm$^3$ | 32 mm$^3$ |
| IL-1α propiece (1–118)-EGFP | 2.3 mm$^3$ | 3.7 mm$^3$ | 4.1 mm$^3$ |

The tumor volume in mice treated with IL-1α propiece (1–118) was significantly smaller than in control mice. In 3 of the 8 mice that received IL-1α propiece (1–118), there was zero or negligible tumor growth. These data show that pre-treatment of A375 melanoma cells with retroviral vectors for expression of IL-1α propiece (1–118) prevents and/or severely diminishes tumor growth in the nude mouse model. These data suggest that IL-1α propiece (1–118) can be used to facilitate inhibition of tumor growth in vivo.

Example 8

Induction of Apoptosis in Cells of the Standard National Cancer Institute (NCI) Panel Cells from the NCI panel of tumor cells were tested for their susceptibility to IL-1α propiece (1–118) by delivery of the IL-1α propiece (1–118)-EGFP fusion protein. Cells were treated with the expression vectors indicated below so as to express either a control sequence (EGFP), IL-1α propiece (1–118)-EGFP, or IL-1α propiece (1–118) (without EGFP). The choice of vectors was based solely on the vector most efficient for a given cell type. After the period indicated, cells were evaluated for morphological signs of apoptosis, including aggregation of IL-1α propiece (1–118)-EGFP into nuclear apoptotic bodies. Cells were counted under a fluorescence microscope and scored as to the presence or absence of apoptotic signs. In some cases, cells were scored by flourescent TUNEL assay and counted in a flow cytometer. Apoptosis is expressed as a percent of cells displaying typical advanced changes of apoptosis. In each cell line tested, expression of EGFP alone or transfection alone (viral vector only) was not associated with any detectable apoptosis.

a) Colon cancer cells

IL-1α propiece (1–118) was expressed in the following cells, which are derived from malignant human colon cancers (adenocarcinomas), by infection with the retrovirus vector described above. Apoptosis was evaluated at 96 hrs post-infection.

TABLE 5

Apoptosis in colon cancer.

| Cell | No. Apoptotic | Total Cells | % |
|---|---|---|---|
| KM12 | 91 | 125 | 73 |
| SW-620 | 22 | 121 | 18 |
| HCT-5 | 77 | 108 | 71 |
| HCT-116 | 112 | 156 | 72 |
| HT-29 | 74 | 109 | 68 |
| COLO205 | 68 | 100 | 68 |
| HCC 2998 | 65 | 91 | 71 |

These data suggest that most colon cancers are susceptible to IL-1α propiece (1–118)-based chemotherapy.

b) Cells of central nervous system tumors

IL-1α propiece (1–118) was expressed in the following cells, which are derived from malignant human central nervous system tumors, by infection with the retrovirus vector described above. Apoptosis was evaluated at 96 hrs post-infection. The specific cancer types of each cell are as follows: SF-268, astrocytoma; SF-539, glioblastoma; SNB-19, gliblastoma; SNB-75, astrocytoma; and U251, glioblastoma.

TABLE 6

Apoptosis in cancers of the central nervous system.

| Cell | No. Apoptotic | Total Cells | % |
|---|---|---|---|
| SF-268 | 38 | 110 | 35 |
| SF-539 | 108 | 131 | 82 |
| SNB-19 | 128 | 137 | 93 |
| SNB-75 | 71 | 115 | 62 |
| U251 | 84 | 108 | 78 |

These data suggest that most tumors of the central nervous system are susceptible to IL-1α propiece (1–118)-based chemotherapy.

c) Leukemia cells

IL-1α propiece (1–118) was expressed in the following cells, which are derived from malignant human leukemias. Expression was accomplished using the retroviral vector and protocol described above. Apoptosis was evaluated at 96 hrs post-infection. The specific leukemia subtypes of the cells are as follows: CCRF-CEM, acute lymphocytic leukemia (ALL); K562, acute myelogenous leukemia (AML); MOLT-4, ALL; SR, immunoblastoma large cell; and RPMI 8226, myeloblastoma.

TABLE 7

Apoptosis in leukemias.

| Cell | No. Apoptotic | Total Cells | % |
|---|---|---|---|
| CCRF-CEM | 81 | 100 | 81 |
| K562 | 36 | 100 | 36 |
| MOLT-4 | 69 | 100 | 69 |
| SR | 85 | 100 | 85 |
| RPMI 8226 | 63 | 100 | 63 |

These data suggest that most leukemias are susceptible to IL-1α propiece (1–118)-based chemotherapy.

d) Prostate cancer cells

IL-1α propiece (1–118) was expressed in the prostate cancer cell PC-3, which is derived from a malignant human prostate tumor. Expression was accomplished using the retrovirus vector and protocol described above. Apoptosis was evaluated at 96 hrs post-infection.

TABLE 8

Apoptosis in prostate cancer.

| Cell | No. Apoptotic | Total Cells | % |
|---|---|---|---|
| PC-3 | 38 | 102 | 37 |

This experiment suggests that prostate cancers may be susceptible to IL-1α propiece (1–118)-based chemotherapy.

e) Kidney cancer cells

IL-1α propiece (1–118) was expressed in the following cells, which are derived from malignant human kidney tumors (renal tumors). Expression was accomplished using the retrovirus vector and protocol described above. Apoptosis was evaluated at 96 hrs post-infection.

TABLE 9

Apoptosis in kidney cancers (renal).

| Cell | No. Apoptotic | Total Cells | % |
| --- | --- | --- | --- |
| 768-0 | 18 | 48 | 38 |
| TK10 | 42 | 103 | 41 |
| UO-31 | 50 | 93 | 54 |
| ACHN | 28 | 52 | 54 |

These data suggest that most kidney cancers are susceptible to IL-1α propiece (1–118)-based chemotherapy.

f) Skin cancer cells (melanoma)

IL-1α propiece (1–118) was expressed in the following human melanoma cells. Expression was accomplished using the retrovirus vector and protocol described above. Apoptosis was evaluated at 96 hrs post-infection.

TABLE 10

Apoptosis in melanomas.

| Cell | No. Apoptotic | Total Cells | % |
| --- | --- | --- | --- |
| SKMEL-28 | 93 | 100 | 93 |
| SKMEL-5 | 73 | 107 | 68 |
| MALME-3 | 72 | 102 | 71 |
| M14 | 45 | 81 | 56 |
| SKMEL-28 | 65 | 101 | 64 |

These data suggest that melanomas are susceptible to IL-1α propiece (1–118)-based chemotherapy.

g) Lung cancer cells

IL-1α propiece (1–118) was expressed in the following cells, which are derived from malignant human lung cancers. Expression was accomplished using the retrovirus vector and protocol described above.

TABLE 11

Apoptosis in lung cancer.

| Cell | No. Apoptotic | Total Cells | % |
| --- | --- | --- | --- |
| HOP-92 | 88 | 102 | 86 |
| HOP-62 | 92 | 105 | 88 |
| NCI-H23 | 96 | 108 | 89 |
| NCI-H226 | 59 | 100 | 59 |
| NCI-H322 | 119 | 147 | 81 |
| NCI-H460 | 103 | 125 | 82 |
| NCI-H522 | 81 | 107 | 76 |
| A549 | 50 | 108 | 46 |
| EKVX | 69 | 100 | 69 |

These data suggest that lung cancers are susceptible to IL-1α propiece (1–118)-based chemotherapy.

h) Breast cancer cells

IL-1α propiece (1–118) was expressed in the following cells, which are derived from malignant human breast cancer. Expression was accomplished using the retrovirus vector and protocol described above.

TABLE 12

Apoptosis in cancers of the mammary gland.

| Cell | No. Apoptotic | Total Cells | % |
| --- | --- | --- | --- |
| MCF-7 | 91 | 110 | 83 |
| MCF-7/ADR- | 20 | 42 | 48 |
| MDAMB23 | 98 | 122 | 80 |
| BT-549 | 57 | 87 | 66 |
| T-47D | 82 | 121 | 68 |
| MDAMB43 | 88 | 120 | 73 |
| MDA-N | 80 | 103 | 78 |

These data suggest that breast cancers are susceptible to IL-1α propiece (1–118)-based chemotherapy.

I) Ovary cancer cells

IL-1α propiece (1–118) was expressed in the following cells, which are derived from malignant human ovarian cancers. Expression was accomplished using either the retroviral expression vector and protocol described above, or the Sindbis viral expression vector and protocol described above. Apoptosis was evaluated at 96 hrs post-infection with retrovirus or at 24 hrs post-infection with Sindbis viral vectors.

TABLE 13

Apoptosis in ovarian cancers using Sindbis viral vector-mediated expression (including floating cells).

| Cell | No. Apoptotic | Total Cells | % |
| --- | --- | --- | --- |
| OVCAR-8 | 63 | 100 | 63 |
| IGROV-1 | 238 | 325 | 87 |
| OVCAR3 | 186 | 247 | 88 |
| OVCAR-4 | 89 | 97 | 96 |
| OVCAR-5 | 159 | 213 | 87 |
| SK-OV-3 | 216 | 280 | 89 |

This particular cell line floats off the plate when it undergoes apoptosis; the percentages reported are the percent of total cells apoptotic. These data show that ovarian cancers are susceptible to IL-1αa propiece (1–118)-based chemotherapy. Further, vectors other than retroviral vectors can be used to accomplish IL-1α (1–118) delivery.

SUMMARY

Delivery of IL-1α propiece (1–118) to cancers of the colon, central nervous system, lung, mammary bland, skin (e.g., melanoma), ovary, prostate, and kidney (e.g., renal cancer), as well as leukemia, are susceptible to IL-1α propiece (1–118)-based chemotherapy.

Example 9

Induction of Apoptosis by Extracellular Delivery of IL-1α Propiece (1–118)

The ability of IL-1α propiece (1–118) to induce apoptosis by extracellular delivery to cells was tested in vitro. Purified IL-1αpropiece (1–118) polypeptide (without EGFP) was expressed in E. coli using an inducible Trp vector system. IL-1α propiece (1–118) was isolated as inclusion bodies, dissolved in urea, and gradually renatured by reduction of urea concentration. Purified IL-1α(1–118) was applied to lymphoma cells, ovarian cancer cells, and Rat-1 immortalized fibroblasts grown in culture medium with reduced serum at a concentration of 1.5 µg/ml (100 nM). Apoptosis was evaluated after 48 hrs. The results are summarized in Table 14.

TABLE 14

Induction of apoptosis by extracellular delivery of IL-1α propiece (1–118)

| Cell Name (cell type) | % apoptotic cells as measured by TUNEL |
|---|---|
| P388D1 (lymphoma) | 55% |
| Raw 264.7 (lymphoma) | >90% |
| M1 (lymphoma) | 30% |
| CHO (ovarian cancer) | 45% |
| Rat-1 (immortalized fibroblast) | <2–5% |

These data show that tumor cells are particularly susceptible to apoptosis induced by extracellular delivery of IL-1α propiece (1–118) polypeptide.

Example 10

Purification of IL-1α Propiece (1–118)

Recombinant IL-1α propiece (1–118) polypeptide was purified by expression of the polypeptide in bacteria. cDNA encoding the N-terminal IL-1α propiece was subcloned into the NcoI/PstI site of the bacterial expression vector, pTRC99A. This plasmid was used to transform E. coli, followed by induction with IPTG. The recombinant protein was recovered in the insoluble inclusion bodies by first pelleting the bacteria in chilled de-ionized water at 3000 g for 20 minutes at 4° C. After addition of protease inhibitors (PMSF, EDTA, pepstatin, Leupeptin), the cells were subjected to three cycles of freeze/thawing in the presence of 1% Triton X 100. The material was centrifuged at 10,000 g for 20 minutes at 4° C. and the resulting pellets (inclusion bodies) incubated for 10 min at 37° C. with 1 mM EDTA, 0.2% NP-40, 2 mM MgCl$_2$, 1 mM CaCl$_2$, 0.2 mg/ml lysozyme and 10 µg/ml DNAse. Following centrifugation at 5000 g for 20 min at 4° C., the purified inclusion bodies were dissolved in 6 M urea, 50 mM Tris/HCl, pH 8.0 with protease inhibitors. Analysis of the recombinant propiece protein was performed with reducing 15% SDS-PAGE gels and Coomassie Blue staining.

Purification of the recombinant protein to homogeneity was performed by two sequential gel chromatography sizing steps with G75 in the same 6 M urea, Tris/HCl, pH 8.0 buffer. Purified recombinant propiece protein was refolded by step-wise dialysis in 50 mM Tris/HCl, pH 8 buffer containing decreasing concentrations of urea. This recombinant propiece preparation has been used to prepare goat polyclonal affinity-purified anti-IL-1α propiece IgG.

Example 11

Production of IL-1α Propiece (1–118)-Fc Fusion Protein

An IL-1α propiece fusion protein was produced from IL-1α propiece (1–118) and an Fc region of human IgG$_1$ (including the hinge) to provide a chimeric polypeptide comprising the Fc region appended to the carboxy-terminus of the IL-1α polypeptide (referred to as the IL-1α propiece-Fc fusion protein). Specifically, an IL-1 cDNA corresponding to nt 1–354 (aa 1–118) (SEQ ID NO:49) was linked, by an overlap PCR amplification with the sequence of the human IgG1 Fc region (from Genbank Z17370) (SEQ ID NO:50). The combined cDNA was re-amplified with PCR primers to add a 5' SalI site and a Kozak sequence preceding the start codon, and a BamHI site at the 3' end. The sequence was cloned into pEGFP-N1. The resulting coding sequence for the IL-1α(1–118)-Fc fusion protein is provided as SEQ ID NO:51) with an amino acid sequence of SEQ ID NO:52. This cassette was then fused to an EGFP coding sequence (SEQ ID NO:53) with an amino acid sequence of SEQ ID NO:54.

The IL-1α(1–118)-Fc-EGFP fusion plasmid was transfected into 293 cells. As a control, a similar plasmid expressing only IL-1α(1–118)-EGFP was also transfected into 293 cells. Apoptosis was scored after 24 hours. The apoptotic effects of the IL-1α-Fc-EGFP were indistinguishable from those of IL-1α-EGFP, both producing apoptosis of approximately 90% of transfected cells at 24 hours.

Example 12

Identification of an Apoptosis-Inducing Polypeptide of Drosophila

The IL-1α amino acid sequence 1–118 and 55–108 (SEQ ID NO:2) were used as query sequences in the NCBI tblastn algorithm restricted to the Drosophila genomic database (as deposited in Genbank between December 1999 and April 2000). One significant positive match was found to the sequence of Genbank Accession No. AC006933. The match was to the predicted translation of nt 35031 to 35163 of AC006933 (DEFINITION Drosophila melanogaster, chromosome 3L, region 73B7-73D6, BAC cloneBACR48E21) (SEQ ID NO:55). The theoretical translation of this region is provided as SEQ ID NO:56, which sequence corresponds closely with aa 47–108 of the human IL-1α propiece (see alignment provided in FIG. 6). This sequence of SEQ ID NO:56 also corresponds closely to the limits of exon 4 of human IL-1α, suggesting that this exon, entirely containing all of the apoptotic activity if the IL-1α propiece, may have had an independent evolutionary function.

To test the activity of the Drosophila melanogaster polypeptide in induction of apoptosis, a cDNA coding cassette for the above sequence was made as an artificial gene constructed from overlapping nucleotides using standard PCR methodologies. The final coding sequence, including a Kozak sequence and an introduced ATG start codon is provided as SEQ ID NO:57. An EcoRI site was introduced on the 5' end and a BamHI site introduced on the 3' end so as to produce the correct reading frame to introduce this fragment into pEGFP-N1-coding for fusion protein with EGFP. The coding sequence of this fusion is provided in SEQ ID NO:58, with is amino acid sequence of SEQ ID NO:59.

The resultant expression vector (pEGFP-N-1-DroExon4) was transfected into 293 cells. Nuclear localization was observed with 24 hours. Signs of apoptosis, such as nuclear fragmentation, formation of apoptotic bodies and cellular blebbing was evident at 48 hours increasing at 72 hours. The rate of apoptosis was approximately 20–25% of transfected cells contrasting with 90% of cells transfected with the IL-1α(1–118) vector.

What is claimed is:

1. An isolated apoptosis-inducing polypeptide comprising:
   a) an apoptosis-inducing domain comprising amino acid residues 75–108 of SEQ ID NO:2; and
   b) a functional nuclear localization sequence that is heterologous to the native human IL-1α propiece polypeptide of SEQ ID NO:2, wherein the apoptosis-inducing polypeptide does not comprise the full length IL-1α propiece polypeptide of SEQ ID NO:2 and wherein the nuclear localization sequence and apoptosis-inducing domain are operably joined.

2. The isolated apoptosis-inducing polypeptide of claim 1, wherein the apoptosis-inducing polypeptide is further characterized by activity in selective induction of apoptosis in a cancer cell without causing significant apoptosis in a non-cancerous cell.

3. An isolated apoptosis-inducing polypeptide comprising an amino acid sequence selected from the group consisting of:
   a) amino acid residues 1–108 of SEQ ID NO:2;
   b) amino acid residues 11–118 of SEQ ID NO:2;
   c) amino acid residues 34–118 of SEQ ID NO:2;
   d) amino acid residues 55–118 of SEQ ID NO:2;
   e) amino acid residues 55–108 of SEQ ID NO:2;
   f) amino acid residues 75–108 of SEQ ID NO:2 operably joined to a nuclear localization sequence, wherein the nuclear localization sequence is obtained from a polypeptide other than a polypeptide of SEQ ID NO:2;
   g) amino acid residues 75–118 of SEQ ID NO:2 operably joined to a nuclear localization sequence, wherein the nuclear localization sequence is obtained from a polypeptide other than a polypeptide of SEQ ID NO:2;
   h) amino acid residues 1–118 of SEQ ID NO:2 operably joined to a leucine zipper domain;
   i) amino acid residues 1–108 of SEQ ID NO:2 operably joined to a leucine zipper domain; and
   j) amino acid residues 55–108 of SEQ ID NO:2 operably joined to a leucine zipper domain;
   with the proviso that the apoptosis-inducing polypeptide does not comprise the full-length IL-1α propiece polypeptide of SEQ ID NO:2 and wherein said apoptosis-inducing polypeptide further comprises a functional nuclear localization sequence heterologous to the native human IL-1α propiece polypeptide of SEQ ID NO:2.

4. The isolated apoptosis-inducing polypeptide of claim 3, wherein the polypeptide is characterized by activity in selective induction of apoptosis in a cancer cell without causing significant apoptosis in a non-cancerous cell.

5. An isolated apoptosis-inducing polypeptide comprising an amino acid sequence selected from the group consisting of:
   a) amino acid residues 1–108 of SEQ ID NO:2;
   b) amino acid residues 11–118 of SEQ ID NO:2;
   c) amino acid residues 34–118 of SEQ ID NO:2;
   d) amino acid residues 55–118 of SEQ ID NO:2;
   e) amino acid residues 55–108 of SEQ ID NO:2;
   f) amino acid residues 75–108 of SEQ ID NO:2 operably joined to a nuclear localization sequence;
   g) amino acid residues 75–118 of SEQ ID NO:2 operably joined to a nuclear localization sequence;
   h) amino acid residues 1–118 of SEQ ID NO:2 operably joined to a leucine zipper
   i) amino acid residues 1–108 of SEQ ID NO:2 operably joined to a leucine zipper domain; and
   j) amino acid residues 55–108 of SEQ ID NO:2 operably joined to a leucine zipper domain,
   wherein serine at position 87 of SEQ ID NO:2 is substituted with an amino acid other than serine.

6. The isolated apoptosis-inducing polypeptide of claim 5, wherein the polypeptide is characterized by activity in selective induction of apoptosis in a cancer cell without causing significant apoptosis in a non-cancerous cell.

7. A pharmaceutical composition comprising the polypeptide of claim 1 in an amount effective to selectively induce apoptosis and a biocompatible carrier.

8. A pharmaceutical composition comprising the polypeptide of claim 3 in an amount effective to selectively induce apoptosis and a biocompatible carrier.

9. A pharmaceutical composition comprising the polypeptide of claim 5 in an amount effective to selectively induce apoptosis and a biocompatible carrier.

* * * * *

UNITED STATES PATENT AND TRADEMARK OFFICE
CERTIFICATE OF CORRECTION

PATENT NO. : 7,176,179 B1
APPLICATION NO. : 09/569698
DATED : February 13, 2007
INVENTOR(S) : Allan S. Pollock et al.

It is certified that error appears in the above-identified patent and that said Letters Patent is hereby corrected as shown below:

Col. 125, Line 18, after "zipper" insert --domain;-- as shown below.

5. An isolated apoptosis-inducing polypeptide comprising an amino acid sequence selected from the group consisting of:

a) amino acid residues 1-108 of SEQ ID NO:2;
b) amino acid residues 11-118 of SEQ ID NO:2;
c) amino acid residues 34-118 of SEQ ID NO:2;
d) amino acid residues 55-118 of SEQ ID NO:2;
e) amino acid residues 55-108 of SEQ ID NO:2;
f) amino acid residues 75-108 of SEQ ID NO:2 operably joined to a nuclear localization sequence;
g) amino acid residues 75-118 of SEQ ID NO:2 operably joined to a nuclear localization sequence;
h) amino acid residues 1-118 of SEQ ID NO:2 operably joined to a leucine zipper <u>domain</u>;
i) amino acid residues 1-108 of SEQ ID NO:2 operably joined to a leucine zipper domain; and
j) amino acid residues 55-108 of SEQ ID NO:2 operably joined to a leucine zipper domain;
wherein serine at position 87 of SEQ ID NO:2 is substituted with an amino acid other than serine.

Signed and Sealed this

Third Day of July, 2007

JON W. DUDAS
*Director of the United States Patent and Trademark Office*

SEQUENCE LISTING

<160> NUMBER OF SEQ ID NOS: 59

<210> SEQ ID NO 1
<211> LENGTH: 354
<212> TYPE: DNA
<213> ORGANISM: Homo sapiens
<220> FEATURE:
<221> NAME/KEY: CDS
<222> LOCATION: (1)...(354)

<400> SEQUENCE: 1

```
atg gcc aaa gtt cca gac atg ttt gaa gac ctg aag aac tgt tac agt      48
Met Ala Lys Val Pro Asp Met Phe Glu Asp Leu Lys Asn Cys Tyr Ser
 1               5                  10                  15 gaa aat gaa gaa gac agt tcc tcc att gat cat ctg tct ctg aat cag      96
Glu Asn Glu Glu Asp Ser Ser Ser Ile Asp His Leu Ser Leu Asn Gln
             20                  25                  30 aaa tcc ttc tat cat gta agc tat ggc cca ctc cat gaa ggc tgc atg     144
Lys Ser Phe Tyr His Val Ser Tyr Gly Pro Leu His Glu Gly Cys Met
         35                  40                  45 gat caa tct gtg tct ctg agt atc tct gaa acc tct aaa aca tcc aag     192
Asp Gln Ser Val Ser Leu Ser Ile Ser Glu Thr Ser Lys Thr Ser Lys
     50                  55                  60 ctt acc ttc aag gag agc atg gtg gta gta gca acc aac ggg aag gtt     240
Leu Thr Phe Lys Glu Ser Met Val Val Val Ala Thr Asn Gly Lys Val
 65                  70                  75                  80 ctg aag aag aga cgg ttg agt tta agc caa tcc atc act gat gat gac     288
Leu Lys Lys Arg Arg Leu Ser Leu Ser Gln Ser Ile Thr Asp Asp Asp
                 85                  90                  95 ctg gag gcc atc gcc aat gac tca gag gaa gaa atc atc aag cct agg     336
Leu Glu Ala Ile Ala Asn Asp Ser Glu Glu Glu Ile Ile Lys Pro Arg
            100                 105                 110 tca gca cct ttt agc ttc                                             354
Ser Ala Pro Phe Ser Phe
            115
```

<210> SEQ ID NO 2
<211> LENGTH: 118
<212> TYPE: PRT
<213> ORGANISM: Homo sapiens

<400> SEQUENCE: 2

```
Met Ala Lys Val Pro Asp Met Phe Glu Asp Leu Lys Asn Cys Tyr Ser
 1               5                  10                  15

Glu Asn Glu Glu Asp Ser Ser Ser Ile Asp His Leu Ser Leu Asn Gln
             20                  25                  30

Lys Ser Phe Tyr His Val Ser Tyr Gly Pro Leu His Glu Gly Cys Met
         35                  40                  45

Asp Gln Ser Val Ser Leu Ser Ile Ser Glu Thr Ser Lys Thr Ser Lys
     50                  55                  60

Leu Thr Phe Lys Glu Ser Met Val Val Val Ala Thr Asn Gly Lys Val
 65                  70                  75                  80

Leu Lys Lys Arg Arg Leu Ser Leu Ser Gln Ser Ile Thr Asp Asp Asp
                 85                  90                  95

Leu Glu Ala Ile Ala Asn Asp Ser Glu Glu Glu Ile Ile Lys Pro Arg
            100                 105                 110

Ser Ala Pro Phe Ser Phe
            115
```

<210> SEQ ID NO 3
<211> LENGTH: 43
<212> TYPE: DNA
<213> ORGANISM: Artificial Sequence
<220> FEATURE:
<223> OTHER INFORMATION: Primer

<400> SEQUENCE: 3
cagtactcga gcggccgcca ccatggccaa agttccagac atg                          43

<210> SEQ ID NO 4
<211> LENGTH: 38
<212> TYPE: DNA
<213> ORGANISM: Artificial Sequence
<220> FEATURE:
<223> OTHER INFORMATION: Primer

<400> SEQUENCE: 4
gactaagatc tctagattag aagctaaaag gtgctgac                                38

<210> SEQ ID NO 5
<211> LENGTH: 1095
<212> TYPE: DNA
<213> ORGANISM: Artificial Sequence
<220> FEATURE:
<223> OTHER INFORMATION: Sequence encoding Il-1alpha propiece - EGFP
      fusion protein
<221> NAME/KEY: CDS
<222> LOCATION: (1)...(1092)

<400> SEQUENCE: 5

| | | | | | | | | | | | | | | | |
|---|---|---|---|---|---|---|---|---|---|---|---|---|---|---|---|
| atg | gcc | aaa | gtt | cca | gac | atg | ttt | gaa | gac | ctg | aag | aac | tgt | tac | agt | 48 |
| Met | Ala | Lys | Val | Pro | Asp | Met | Phe | Glu | Asp | Leu | Lys | Asn | Cys | Tyr | Ser | |
| 1 | | | | 5 | | | | | 10 | | | | | 15 | | |

| gaa | aat | gaa | gaa | gac | agt | tcc | tcc | att | gat | cat | ctg | tct | ctg | aat | cag | 96 |
|---|---|---|---|---|---|---|---|---|---|---|---|---|---|---|---|---|
| Glu | Asn | Glu | Glu | Asp | Ser | Ser | Ser | Ile | Asp | His | Leu | Ser | Leu | Asn | Gln | |
| | | 20 | | | | | 25 | | | | | 30 | | | | |

| aaa | tcc | ttc | tat | cat | gta | agc | tat | ggc | cca | ctc | cat | gaa | ggc | tgc | atg | 144 |
|---|---|---|---|---|---|---|---|---|---|---|---|---|---|---|---|---|
| Lys | Ser | Phe | Tyr | His | Val | Ser | Tyr | Gly | Pro | Leu | His | Glu | Gly | Cys | Met | |
| | 35 | | | | | 40 | | | | | 45 | | | | | |

| gat | caa | tct | gtg | tct | ctg | agt | atc | tct | gaa | acc | tct | aaa | aca | tcc | aag | 192 |
|---|---|---|---|---|---|---|---|---|---|---|---|---|---|---|---|---|
| Asp | Gln | Ser | Val | Ser | Leu | Ser | Ile | Ser | Glu | Thr | Ser | Lys | Thr | Ser | Lys | |
| 50 | | | | | 55 | | | | | 60 | | | | | | |

| ctt | acc | ttc | aag | gag | agc | atg | gtg | gta | gta | gca | acc | aac | ggg | aag | gtt | 240 |
|---|---|---|---|---|---|---|---|---|---|---|---|---|---|---|---|---|
| Leu | Thr | Phe | Lys | Glu | Ser | Met | Val | Val | Val | Ala | Thr | Asn | Gly | Lys | Val | |
| 65 | | | | | 70 | | | | | 75 | | | | | 80 | |

| ctg | aag | aag | aga | cgg | ttg | agt | tta | agc | caa | tcc | atc | act | gat | gat | gac | 288 |
|---|---|---|---|---|---|---|---|---|---|---|---|---|---|---|---|---|
| Leu | Lys | Lys | Arg | Arg | Leu | Ser | Leu | Ser | Gln | Ser | Ile | Thr | Asp | Asp | Asp | |
| | | | | 85 | | | | | 90 | | | | | 95 | | |

| ctg | gag | gcc | atc | gcc | aat | gac | tca | gag | gaa | gaa | atc | atc | aag | cct | agg | 336 |
|---|---|---|---|---|---|---|---|---|---|---|---|---|---|---|---|---|
| Leu | Glu | Ala | Ile | Ala | Asn | Asp | Ser | Glu | Glu | Glu | Ile | Ile | Lys | Pro | Arg | |
| | | | 100 | | | | | 105 | | | | | 110 | | | |

| tca | gca | cct | ttt | agc | ttc | ttg | gat | cca | ccg | gtc | gcc | acc | atg | gtg | agc | 384 |
|---|---|---|---|---|---|---|---|---|---|---|---|---|---|---|---|---|
| Ser | Ala | Pro | Phe | Ser | Phe | Leu | Asp | Pro | Pro | Val | Ala | Thr | Met | Val | Ser | |
| | | 115 | | | | | 120 | | | | | 125 | | | | |

| aag | ggc | gag | gag | ctg | ttc | acc | ggg | gtg | gtg | ccc | atc | ctg | gtc | gag | ctg | 432 |
|---|---|---|---|---|---|---|---|---|---|---|---|---|---|---|---|---|
| Lys | Gly | Glu | Glu | Leu | Phe | Thr | Gly | Val | Val | Pro | Ile | Leu | Val | Glu | Leu | |
| | 130 | | | | | 135 | | | | | 140 | | | | | |

| gac | ggc | gac | gta | aac | ggc | cac | aag | ttc | agc | gtg | tcc | ggc | gag | ggc | gag | 480 |
|---|---|---|---|---|---|---|---|---|---|---|---|---|---|---|---|---|
| Asp | Gly | Asp | Val | Asn | Gly | His | Lys | Phe | Ser | Val | Ser | Gly | Glu | Gly | Glu | |
| 145 | | | | | 150 | | | | | 155 | | | | | 160 | |

| ggc | gat | gcc | acc | tac | ggc | aag | ctg | acc | ctg | aag | ttc | atc | tgc | acc | acc | 528 |
|---|---|---|---|---|---|---|---|---|---|---|---|---|---|---|---|---|
| Gly | Asp | Ala | Thr | Tyr | Gly | Lys | Leu | Thr | Leu | Lys | Phe | Ile | Cys | Thr | Thr | |

-continued

```
                   165                 170                 175
ggc aag ctg ccc gtg ccc tgg ccc acc ctc gtg acc acc ctg acc tac      576
Gly Lys Leu Pro Val Pro Trp Pro Thr Leu Val Thr Thr Leu Thr Tyr
            180                 185                 190 ggc gtg cag tgc ttc agc cgc tac ccc gac cac atg aag cag cac gac      624
Gly Val Gln Cys Phe Ser Arg Tyr Pro Asp His Met Lys Gln His Asp
        195                 200                 205 ttc ttc aag tcc gcc atg ccc gaa ggc tac gtc cag gag cgc acc atc      672
Phe Phe Lys Ser Ala Met Pro Glu Gly Tyr Val Gln Glu Arg Thr Ile
    210                 215                 220 ttc ttc aag gac gac ggc aac tac aag acc cgc gcc gag gtg aag ttc      720
Phe Phe Lys Asp Asp Gly Asn Tyr Lys Thr Arg Ala Glu Val Lys Phe
225                 230                 235                 240 gag ggc gac acc ctg gtg aac cgc atc gag ctg aag ggc atc gac ttc      768
Glu Gly Asp Thr Leu Val Asn Arg Ile Glu Leu Lys Gly Ile Asp Phe
                245                 250                 255 aag gag gac ggc aac atc ctg ggg cac aag ctg gag tac aac tac aac      816
Lys Glu Asp Gly Asn Ile Leu Gly His Lys Leu Glu Tyr Asn Tyr Asn
            260                 265                 270 agc cac aac gtc tat atc atg gcc gac aag cag aag aac ggc atc aag      864
Ser His Asn Val Tyr Ile Met Ala Asp Lys Gln Lys Asn Gly Ile Lys
        275                 280                 285 gtg aac ttc aag atc cgc cac aac atc gag gac ggc agc gtg cag ctc      912
Val Asn Phe Lys Ile Arg His Asn Ile Glu Asp Gly Ser Val Gln Leu
    290                 295                 300 gcc gac cac tac cag cag aac acc ccc atc ggc gac ggc ccc gtg ctg      960
Ala Asp His Tyr Gln Gln Asn Thr Pro Ile Gly Asp Gly Pro Val Leu
305                 310                 315                 320 ctg ccc gac aac cac tac ctg agc acc cag tcc gcc ctg agc aaa gac     1008
Leu Pro Asp Asn His Tyr Leu Ser Thr Gln Ser Ala Leu Ser Lys Asp
                325                 330                 335 ccc aac gag aag cgc gat cac atg gtc ctg ctg gag ttc gtg acc gcc     1056
Pro Asn Glu Lys Arg Asp His Met Val Leu Leu Glu Phe Val Thr Ala
            340                 345                 350 gcc ggg atc act ctc ggc atg gac gag ctg tac aag taa                 1095
Ala Gly Ile Thr Leu Gly Met Asp Glu Leu Tyr Lys
        355                 360
```

<210> SEQ ID NO 6
<211> LENGTH: 364
<212> TYPE: PRT
<213> ORGANISM: Artificial Sequence
<220> FEATURE:
<223> OTHER INFORMATION: Fusion protein

<400> SEQUENCE: 6

```
Met Ala Lys Val Pro Asp Met Phe Glu Asp Leu Lys Asn Cys Tyr Ser
  1               5                  10                  15

Glu Asn Glu Glu Asp Ser Ser Ser Ile Asp His Leu Ser Leu Asn Gln
             20                  25                  30

Lys Ser Phe Tyr His Val Ser Tyr Gly Pro Leu His Glu Gly Cys Met
         35                  40                  45

Asp Gln Ser Val Ser Leu Ser Ile Ser Glu Thr Ser Lys Thr Ser Lys
     50                  55                  60

Leu Thr Phe Lys Glu Ser Met Val Val Ala Thr Asn Gly Lys Val
 65                  70                  75                  80

Leu Lys Lys Arg Arg Leu Ser Leu Ser Gln Ser Ile Thr Asp Asp Asp
                 85                  90                  95

Leu Glu Ala Ile Ala Asn Asp Ser Glu Glu Glu Ile Ile Lys Pro Arg
```

```
                100                 105                 110
Ser Ala Pro Phe Ser Phe Leu Asp Pro Val Ala Thr Met Val Ser
            115                 120                 125

Lys Gly Glu Glu Leu Phe Thr Gly Val Val Pro Ile Leu Val Glu Leu
        130                 135                 140

Asp Gly Asp Val Asn Gly His Lys Phe Ser Val Ser Gly Glu Gly Glu
145                 150                 155                 160

Gly Asp Ala Thr Tyr Gly Lys Leu Thr Leu Lys Phe Ile Cys Thr Thr
                165                 170                 175

Gly Lys Leu Pro Val Pro Trp Pro Thr Leu Val Thr Thr Leu Thr Tyr
            180                 185                 190

Gly Val Gln Cys Phe Ser Arg Tyr Pro Asp His Met Lys Gln His Asp
        195                 200                 205

Phe Phe Lys Ser Ala Met Pro Glu Gly Tyr Val Gln Glu Arg Thr Ile
    210                 215                 220

Phe Phe Lys Asp Asp Gly Asn Tyr Lys Thr Arg Ala Glu Val Lys Phe
225                 230                 235                 240

Glu Gly Asp Thr Leu Val Asn Arg Ile Glu Leu Lys Gly Ile Asp Phe
                245                 250                 255

Lys Glu Asp Gly Asn Ile Leu Gly His Lys Leu Glu Tyr Asn Tyr Asn
            260                 265                 270

Ser His Asn Val Tyr Ile Met Ala Asp Lys Gln Lys Asn Gly Ile Lys
        275                 280                 285

Val Asn Phe Lys Ile Arg His Asn Ile Glu Asp Gly Ser Val Gln Leu
    290                 295                 300

Ala Asp His Tyr Gln Gln Asn Thr Pro Ile Gly Asp Gly Pro Val Leu
305                 310                 315                 320

Leu Pro Asp Asn His Tyr Leu Ser Thr Gln Ser Ala Leu Ser Lys Asp
                325                 330                 335

Pro Asn Glu Lys Arg Asp His Met Val Leu Leu Glu Phe Val Thr Ala
            340                 345                 350

Ala Gly Ile Thr Leu Gly Met Asp Glu Leu Tyr Lys
        355                 360

<210> SEQ ID NO 7
<211> LENGTH: 271
<212> TYPE: PRT
<213> ORGANISM: Homo sapiens

<400> SEQUENCE: 7

Met Ala Lys Val Pro Asp Met Phe Glu Asp Leu Lys Asn Cys Tyr Ser
1               5                   10                  15

Glu Asn Glu Glu Asp Ser Ser Ile Asp His Leu Ser Leu Asn Gln
            20                  25                  30

Lys Ser Phe Tyr His Val Ser Tyr Gly Pro Leu His Glu Gly Cys Met
        35                  40                  45

Asp Gln Ser Val Ser Leu Ser Ile Ser Glu Thr Ser Lys Thr Ser Lys
    50                  55                  60

Leu Thr Phe Lys Glu Ser Met Val Val Ala Thr Asn Gly Lys Val
65                  70                  75                  80

Leu Lys Lys Arg Arg Leu Ser Leu Ser Gln Ser Ile Thr Asp Asp Asp
                85                  90                  95

Leu Glu Ala Ile Ala Asn Asp Ser Glu Glu Ile Ile Lys Pro Arg
            100                 105                 110
```

```
Ser Ala Pro Phe Ser Phe Leu Ser Asn Val Lys Tyr Asn Phe Met Arg
        115                 120                 125

Ile Ile Lys Tyr Glu Phe Ile Leu Asn Asp Ala Leu Asn Gln Ser Ile
130             135                 140

Ile Arg Ala Asn Asp Gln Tyr Leu Thr Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
            180                 185                 190

Val Thr Ala Gln Asp Glu Asp Gln Pro Val Leu Leu Lys Glu Met Pro
        195                 200                 205

Glu Ile Pro Lys Thr Ile Thr Gly Ser Glu Thr Asn Leu Leu Phe Phe
    210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                245                 250                 255

Gly Pro Pro Ser Ile Thr Asp Phe Gln Ile Leu Glu Asn Gln Ala
            260                 265                 270

<210> SEQ ID NO 8
<211> LENGTH: 268
<212> TYPE: PRT
<213> ORGANISM: Bovine spp.

<400> SEQUENCE: 8

Met Ala Lys Val Pro Asp Leu Phe Glu Asp Leu Lys Asn Cys Tyr Ser
1               5                   10                  15

Glu Asn Glu Asp Tyr Ser Ser Glu Ile Asp His Leu Ser Leu Asn Gln
            20                  25                  30

Lys Ser Phe Tyr Asp Ala Ser Tyr Glu Pro Leu Arg Glu Asp Gln Met
        35                  40                  45

Asn Lys Phe Met Ser Leu Asp Thr Ser Glu Thr Ser Lys Thr Ser Lys
    50                  55                  60

Leu Ser Phe Lys Glu Asn Val Val Met Val Ala Ala Ser Gly Lys Ile
65                  70                  75                  80

Leu Lys Lys Arg Arg Leu Ser Leu Asn Gln Phe Ile Thr Asp Asp Asp
                85                  90                  95

Leu Glu Ala Ile Ala Asn Asn Thr Glu Glu Ile Ile Lys Pro Arg
            100                 105                 110

Ser Ala His Tyr Ser Phe Gln Ser Asn Val Lys Tyr Asn Phe Met Arg
        115                 120                 125

Val Ile His Gln Glu Cys Ile Leu Asn Asp Ala Leu Asn Gln Ser Ile
130                 135                 140

Ile Arg Asp Met Ser Gly Pro Tyr Leu Thr Ala Thr Leu Asn Asn
145                 150                 155                 160

Leu Glu Glu Ala Val Lys Phe Asp Met Val Ala Tyr Val Ser Glu Glu
                165                 170                 175

Asp Ser Gln Leu Pro Val Thr Leu Arg Ile Ser Lys Thr Gln Leu Phe
            180                 185                 190

Val Ser Ala Gln Asn Glu Asp Glu Pro Val Leu Leu Lys Glu Met Pro
        195                 200                 205

Glu Thr Pro Lys Ile Ile Lys Asp Glu Thr Asn Leu Leu Phe Phe Trp
    210                 215                 220
```

```
Glu Lys His Gly Ser Met Asp Tyr Phe Lys Ser Val Ala His Pro Lys
225                 230                 235                 240

Leu Phe Ile Ala Thr Lys Gln Glu Lys Leu Val His Met Ala Ser Gly
                245                 250                 255

Pro Pro Ser Ile Thr Asp Phe Gln Ile Leu Glu Lys
                260                 265
```

<210> SEQ ID NO 9
<211> LENGTH: 265
<212> TYPE: PRT
<213> ORGANISM: Canus spp. (dog)

<400> SEQUENCE: 9

```
Met Ala Lys Val Pro Asp Leu Phe Glu Asp Leu Lys Asn Cys Tyr Ser
1               5                   10                  15

Glu Asn Glu Glu Tyr Ser Ser Glu Ile Asp His Leu Ser Leu Asn Gln
                20                  25                  30

Lys Ser Phe Tyr Asp Met Ser Cys Asp Pro Leu His Glu Asp Cys Met
            35                  40                  45

Ser Leu Ser Thr Ser Glu Ile Ser Lys Thr Ser Gln Leu Thr Phe Lys
    50                  55                  60

Glu Asn Val Val Val Ala Ala Asn Gly Lys Ile Leu Lys Lys Arg
65                  70                  75                  80

Arg Leu Ser Leu Ser Gln Phe Ile Thr Asp Asp Leu Glu Gly Ile
                85                  90                  95

Ala Asn Asp Thr Glu Val Ile Met Lys Pro Arg Ser Val Ala Tyr
                100                 105                 110

Asn Phe His Asn Asn Glu Lys Tyr Asn Tyr Ile Arg Ile Ile Lys Ser
            115                 120                 125

Gln Phe Ile Leu Asn Asp Asn Leu Asn Gln Ser Ile Val Arg Gln Thr
        130                 135                 140

Gly Gly Asn Tyr Leu Met Thr Ala Ala Leu Gln Asn Leu Asp Asp Ala
145                 150                 155                 160

Val Lys Phe Asp Met Gly Ala Tyr Thr Ser Glu Asp Ser Lys Leu Pro
                165                 170                 175

Val Thr Leu Arg Ile Ser Lys Thr Arg Leu Phe Val Ser Ala Gln Asn
                180                 185                 190

Glu Asp Glu Pro Val Leu Leu Lys Glu Met Pro Glu Thr Pro Lys Thr
            195                 200                 205

Ile Arg Asp Glu Thr Asn Leu Leu Phe Phe Trp Glu Arg His Gly Ser
        210                 215                 220

Lys His Tyr Phe Lys Ser Val Ala Gln Pro Lys Leu Phe Ile Ala Thr
225                 230                 235                 240

Gln Glu Arg Lys Leu Val His Met Ala Arg Gly Gln Pro Ser Ile Thr
                245                 250                 255

Asp Phe Arg Leu Leu Glu Thr Gln Pro
                260                 265
```

<210> SEQ ID NO 10
<211> LENGTH: 268
<212> TYPE: PRT
<213> ORGANISM: Capra spp. (goat)

<400> SEQUENCE: 10

```
Met Ala Lys Val Pro Asp Leu Phe Glu Asp Leu Lys Asn Cys Tyr Ser
1               5                   10                  15
```

-continued

```
Glu Asn Glu Asp Tyr Ser Ser Glu Ile Asp His Leu Ser Leu Asn Gln
            20                  25                  30

Lys Ser Phe Tyr Asp Ala Ser Tyr Gly Pro Leu Arg Glu Asp His Met
        35                  40                  45

Asn Lys Phe Met Ser Leu Asp Thr Ser Glu Thr Ser Lys Thr Ser Arg
    50                  55                  60

Leu Ser Phe Lys Glu Asn Val Val Met Val Thr Ala Asn Gly Lys Ile
65                  70                  75                  80

Leu Lys Lys Arg Arg Leu Ser Leu Asn Gln Phe Ile Thr Asp Asp
                85                  90                  95

Leu Glu Ala Ile Ala Asn Asp Thr Glu Glu Ile Ile Lys Pro Arg
                100                 105                 110

Ser Ala His Tyr Ser Phe Gln Ser Asn Val Lys Tyr Asn Phe Met Arg
            115                 120                 125

Val Ile His Gln Glu Cys Ile Leu Asn Asp Ala Leu Asn Gln Ser Ile
        130                 135                 140

Ile Arg Asp Met Ser Gly Pro Tyr Leu Met Ala Ala Thr Leu Asn Asn
145                 150                 155                 160

Leu Glu Glu Ala Val Lys Phe Asp Met Val Ala Tyr Val Ser Glu Glu
                165                 170                 175

Asp Ser Gln Leu Pro Val Thr Leu Arg Ile Ser Lys Thr Gln Leu Phe
            180                 185                 190

Val Ser Ala Gln Asn Glu Asp Glu Pro Val Leu Leu Lys Glu Met Pro
        195                 200                 205

Glu Thr Pro Lys Ile Ile Lys Asp Glu Thr Asn Leu Leu Phe Phe Trp
    210                 215                 220

Glu Lys His Gly Ser Met Asp Tyr Phe Lys Ser Val Ala His Pro Lys
225                 230                 235                 240

Leu Phe Ile Ala Thr Lys Gln Glu Lys Leu Val His Met Ala Ser Gly
                245                 250                 255

Pro Pro Ser Ile Thr Asp Phe Gln Ile Leu Glu Lys
            260                 265

<210> SEQ ID NO 11
<211> LENGTH: 204
<212> TYPE: PRT
<213> ORGANISM: Cavia spp. (guinea pig)

<400> SEQUENCE: 11

Phe Glu Asp Leu Lys Asn Cys Tyr Ser Glu Asn Glu Glu Tyr Ala Ser
1               5                   10                  15

Ala Ile Asp His Leu Ser Leu Asn Gln Lys Ser Phe Tyr Asp Thr Asn
            20                  25                  30

Tyr Asp Pro Leu His Glu Asn Arg Val Asp Glu Pro Val Ser Pro Asn
        35                  40                  45

Pro Tyr Glu Asn Ser Glu Glu Ser Asn Phe Thr Leu Glu Asp Ser Ser
    50                  55                  60

Asp Ser Ser Ala Val Val Leu Thr Ser Ala His Gly Glu Val Leu Lys
65                  70                  75                  80

Lys Arg Arg Leu Ser Leu Asn Gln Thr Met Ser Asn Glu Asp Leu Glu
                85                  90                  95

Ala Ile Ala Asn Asp Ser Glu Glu Ile Ile Glu Pro Trp Ser Val
                100                 105                 110

Pro Tyr Ser Phe Gln Ser Asn Leu Lys Phe Lys Tyr Gln Arg Ser Ile
```

```
                115                 120                 125
Lys Lys Gly Ala Val Ile Thr Asp Ala Met His Gln Ser Leu Ile Arg
        130                 135                 140

Glu Ser Asn Gly Gln His Leu Lys Ala Met His Val Val Asp Arg Lys
145                 150                 155                 160

His Glu Val Lys Phe Asp Ile Asp Gly Tyr Val Ser Thr Ala Thr Arg
                165                 170                 175

Ile Arg Pro Val Thr Leu Lys Ile Ser Lys Thr Gln Leu Tyr Val Cys
                180                 185                 190

Ala Gln Glu Glu Gly Gln Pro Val Leu Leu Lys Glu
        195                 200

<210> SEQ ID NO 12
<211> LENGTH: 271
<212> TYPE: PRT
<213> ORGANISM: Cercoceus troquatus atys

<400> SEQUENCE: 12

Met Ala Lys Val Pro Asp Met Phe Glu Asp Leu Lys Asn Cys Tyr Ser
1               5                   10                  15

Glu Asn Glu Glu Asp Ser Ser Ile Asp His Leu Phe Leu Asn Gln
            20                  25                  30

Lys Ser Phe Tyr Asp Val Ser Tyr Gly Pro Leu His Glu Ser Cys Met
        35                  40                  45

Asp Gln Ser Val Ser Leu Ser Ile Ser Glu Ile Ser Lys Thr Ser Lys
    50                  55                  60

Leu Ser Phe Lys Gln Ser Met Val Val Ser Thr Asn Gly Lys Val
65                  70                  75                  80

Leu Lys Lys Arg Arg Leu Ser Leu Ser Gln Ser Ile Ala Asp Asp Asn
                85                  90                  95

Leu Glu Ala Ile Ala Asn Asp Ser Glu Glu Ile Ile Lys Pro Arg
            100                 105                 110

Ser Ala Pro Phe Ser Phe Leu Ser Asn Met Thr Tyr His Ile Ile Arg
        115                 120                 125

Ile Ile Lys His Glu Ser Ile Leu Asn Asp Thr Leu Asn Gln Thr Ile
130                 135                 140

Ile Arg Ala Asn Asp Gln Tyr Leu Thr Ala Ala Ile His Asn Leu
145                 150                 155                 160

Asp Glu Ala Val Lys Phe Asp Met Gly Ala Tyr Thr Ser Ser Lys Asp
                165                 170                 175

Asp Thr Lys Val Pro Val Ile Leu Arg Ile Ser Lys Thr Gln Leu Tyr
            180                 185                 190

Val Ser Ala Gln Asp Glu Asp Gln Pro Val Leu Leu Lys Glu Met Pro
        195                 200                 205

Glu Ile Pro Lys Thr Thr Thr Gly Gly Glu Thr Asn Ser Leu Ser Ser
    210                 215                 220

Trp Glu Thr Arg Gly Thr Lys Asn Tyr Phe Ile Ser Val Ala His Pro
225                 230                 235                 240

Asn Leu Phe Ile Ala Thr Lys His Asp Asn Trp Val Cys Leu Ala Lys
                245                 250                 255

Gly Leu Pro Ser Ile Thr Asp Phe Gln Ile Leu Glu Asn Gln Ala
            260                 265                 270

<210> SEQ ID NO 13
<211> LENGTH: 270
```

```
<212> TYPE: PRT
<213> ORGANISM: Equus spp. (horse)

<400> SEQUENCE: 13

Met Ala Lys Val Pro Asp Leu Phe Glu Asp Leu Lys Asn Cys Tyr Ser
1               5                   10                  15

Glu Asn Glu Asp Tyr Ser Ser Glu Ile Asp His Leu Ser Leu Thr Gln
            20                  25                  30

Lys Ser Phe Tyr Asp Ala Ser Tyr Asp Pro Leu Pro Glu Asp Cys Met
        35                  40                  45

Asp Thr Phe Met Ser Leu Ser Thr Ser Glu Thr Ser Lys Thr Ser Lys
    50                  55                  60

Leu Asn Phe Lys Glu Ser Val Leu Val Ala Ala Asn Gly Lys Thr
65                  70                  75                  80

Leu Lys Lys Arg Arg Leu Ser Leu Asn Gln Phe Ile Thr Asn Asp Asp
                85                  90                  95

Leu Glu Ala Ile Ala Asn Asp Pro Glu Glu Gly Ile Ile Arg Pro Arg
                100                 105                 110

Ser Val His Tyr Asn Phe Gln Ser Asn Thr Lys Tyr Asn Phe Met Arg
            115                 120                 125

Ile Val Asn His Gln Cys Thr Leu Asn Asp Ala Leu Asn Gln Ser Val
    130                 135                 140

Ile Arg Asp Thr Ser Gly Gln Tyr Leu Ala Thr Ala Ala Leu Asn Asn
145                 150                 155                 160

Leu Asp Asp Ala Val Lys Phe Asp Met Gly Ala Tyr Thr Ser Glu Glu
                165                 170                 175

Asp Ser Gln Leu Pro Val Thr Leu Arg Ile Ser Lys Thr Arg Leu Phe
            180                 185                 190

Val Ser Ala Gln Asn Glu Asp Glu Pro Val Leu Leu Lys Glu Met Pro
        195                 200                 205

Asp Thr Pro Lys Thr Ile Lys Asp Glu Thr Asn Leu Leu Phe Phe Trp
    210                 215                 220

Glu Arg His Gly Ser Lys Asn Tyr Phe Lys Ser Val Ala His Pro Lys
225                 230                 235                 240

Leu Phe Ile Ala Thr Lys Gln Gly Lys Leu Val His Met Ala Arg Gly
                245                 250                 255

Gln Pro Ser Ile Thr Asp Phe Gln Ile Leu Asp Asn Gln Phe
            260                 265                 270

<210> SEQ ID NO 14
<211> LENGTH: 270
<212> TYPE: PRT
<213> ORGANISM: Feline spp.

<400> SEQUENCE: 14

Met Ala Lys Val Pro Asp Leu Phe Glu Asp Leu Lys Asn Cys Tyr Ser
1               5                   10                  15

Glu Asn Glu Glu Tyr Ser Ser Glu Ile Asp His Leu Thr Leu Asn Gln
            20                  25                  30

Lys Ser Phe Tyr Asp Ala Ser Tyr Asp Pro Leu His Glu Asp Cys Thr
        35                  40                  45

Asp Lys Phe Met Ser Pro Ser Thr Ser Glu Thr Ser Lys Thr Pro Gln
    50                  55                  60

Leu Thr Leu Lys Lys Ser Val Val Met Val Ala Ala Asn Gly Lys Ile
65                  70                  75                  80
```

-continued

```
Leu Lys Lys Arg Arg Leu Ser Leu Asn Gln Phe Leu Thr Ala Asp Asp
            85                  90                  95

Leu Glu Ala Ile Ala Asn Glu Val Glu Glu Ile Met Lys Pro Arg
        100                 105                 110

Ser Val Ala Pro Asn Phe Tyr Ser Glu Lys Tyr Asn Tyr Gln Lys
        115                 120                 125

Ile Ile Lys Ser Gln Phe Ile Leu Asn Asp Asn Leu Ser Gln Ser Val
130                 135                 140

Ile Arg Lys Ala Gly Gly Lys Tyr Leu Ala Ala Ala Leu Gln Asn
145                 150                 155                 160

Leu Asp Asp Ala Val Lys Phe Asp Met Gly Ala Tyr Thr Ser Lys Glu
            165                 170                 175

Asp Ser Lys Leu Pro Val Thr Leu Arg Ile Ser Lys Thr Arg Leu Phe
        180                 185                 190

Val Ser Ala Gln Asn Glu Asp Glu Pro Val Leu Leu Lys Glu Met Pro
        195                 200                 205

Glu Thr Pro Lys Thr Ile Arg Asp Glu Thr Asn Leu Leu Phe Phe Trp
        210                 215                 220

Glu Arg His Gly Ser Lys Asn Tyr Phe Lys Ser Val Ala His Pro Lys
225                 230                 235                 240

Leu Phe Ile Ala Thr Gln Glu Glu Gln Leu Val His Met Ala Arg Gly
            245                 250                 255

Leu Pro Ser Val Thr Asp Phe Gln Ile Leu Glu Thr Gln Ser
        260                 265                 270

<210> SEQ ID NO 15
<211> LENGTH: 271
<212> TYPE: PRT
<213> ORGANISM: Macaca spp.

<400> SEQUENCE: 15

Met Ala Lys Val Pro Asp Met Phe Glu Asp Leu Lys Asn Cys Tyr Ser
1               5                   10                  15

Glu Asn Glu Glu Val Ser Ser Ser Ile Asp His Leu Ser Leu Asn Gln
            20                  25                  30

Lys Ser Phe Tyr Asp Val Ser Tyr Gly Pro Leu His Glu Gly Cys Met
        35                  40                  45

Asp Gln Ser Val Ser Leu Ser Ile Ser Glu Ile Ser Lys Thr Ser Lys
    50                  55                  60

Leu Thr Phe Lys Gln Ser Met Val Val Ser Thr Asn Gly Lys Val
65                  70                  75                  80

Leu Lys Lys Arg Arg Leu Ser Leu Ser Gln Ser Ile Thr Asp Asn Asn
            85                  90                  95

Leu Glu Ala Ile Ala Asn Asp Ser Glu Glu Ile Ile Lys Pro Arg
        100                 105                 110

Ser Ala Pro Phe Ser Phe Leu Ser Asn Met Thr Tyr His Phe Ile Arg
        115                 120                 125

Ile Ile Lys His Glu Phe Ile Leu Asn Asp Thr Leu Asn Gln Thr Ile
130                 135                 140

Ile Arg Ala Asn Asp Gln Tyr Leu Thr Ala Ala Ile His Asn Leu
145                 150                 155                 160

Asp Glu Ala Val Lys Phe Asp Met Gly Ala Tyr Thr Ser Ser Lys Asp
            165                 170                 175

Asp Thr Lys Val Pro Val Ile Leu Arg Ile Ser Lys Thr Gln Leu Tyr
        180                 185                 190
```

```
Val Ser Ala Gln Asp Glu Asp Gln Pro Val Leu Leu Lys Glu Met Pro
        195                 200                 205

Glu Ile Pro Lys Thr Ile Thr Gly Ser Glu Thr Asn Phe Leu Phe Phe
        210                 215                 220

Trp Glu Thr His Gly Thr Lys Asn Tyr Phe Ile Ser Val Ala His Pro
225                 230                 235                 240

Asn Leu Phe Ile Ala Thr Lys His Asp Asn Trp Val Cys Leu Ala Lys
                245                 250                 255

Gly Leu Pro Ser Ile Thr Asp Phe Gln Ile Leu Glu Asn Gln Ala
                260                 265                 270

<210> SEQ ID NO 16
<211> LENGTH: 270
<212> TYPE: PRT
<213> ORGANISM: Murine spp.

<400> SEQUENCE: 16

Met Ala Lys Val Pro Asp Leu Phe Glu Asp Leu Lys Asn Cys Tyr Ser
1               5                   10                  15

Glu Asn Glu Asp Tyr Ser Ser Ala Ile Asp His Leu Ser Leu Asn Gln
            20                  25                  30

Lys Ser Phe Tyr Asp Ala Ser Tyr Gly Ser Leu His Glu Thr Cys Thr
        35                  40                  45

Asp Gln Phe Val Ser Leu Arg Thr Ser Glu Thr Ser Lys Met Ser Asn
    50                  55                  60

Phe Thr Phe Lys Glu Ser Arg Val Thr Val Ser Ala Thr Ser Ser Asn
65                  70                  75                  80

Gly Lys Ile Leu Lys Lys Arg Leu Ser Phe Ser Glu Thr Phe Thr
                85                  90                  95

Glu Asp Asp Leu Gln Ser Ile Thr His Asp Leu Glu Glu Thr Ile Gln
            100                 105                 110

Pro Arg Ser Ala Pro Tyr Thr Tyr Gln Ser Asp Leu Arg Tyr Lys Leu
        115                 120                 125

Met Lys Leu Val Arg Gln Lys Phe Val Met Asn Asp Ser Leu Asn Gln
    130                 135                 140

Thr Ile Tyr Gln Asp Val Asp Lys His Tyr Leu Ser Thr Thr Trp Leu
145                 150                 155                 160

Asn Asp Leu Gln Gln Glu Val Lys Phe Asp Met Tyr Ala Tyr Ser Ser
                165                 170                 175

Gly Gly Asp Asp Ser Lys Tyr Pro Val Thr Leu Lys Ile Ser Asp Ser
            180                 185                 190

Gln Leu Phe Val Ser Ala Gln Gly Glu Asp Gln Pro Val Leu Leu Lys
        195                 200                 205

Glu Leu Pro Glu Thr Pro Lys Leu Ile Thr Gly Ser Glu Thr Asp Leu
        210                 215                 220

Ile Phe Phe Trp Lys Ser Ile Asn Ser Lys Asn Tyr Phe Thr Ser Ala
225                 230                 235                 240

Ala Tyr Pro Glu Leu Phe Ile Ala Thr Lys Glu Gln Ser Arg Val His
                245                 250                 255

Leu Ala Arg Gly Leu Pro Ser Met Thr Asp Phe Gln Ile Ser
            260                 265                 270

<210> SEQ ID NO 17
<211> LENGTH: 268
<212> TYPE: PRT
```

<213> ORGANISM: Ovis spp. (sheep)

<400> SEQUENCE: 17

```
Met Ala Lys Val Pro Asp Leu Phe Glu Asp Leu Lys Asn Cys Tyr Ser
1               5                   10                  15

Glu Asn Glu Asp Tyr Ser Ser Glu Ile Asp His Leu Ser Leu Asn Gln
            20                  25                  30

Lys Ser Phe Tyr Asp Ala Ser Tyr Glu Pro Leu Arg Glu Asp His Met
        35                  40                  45

Asn Lys Phe Met Ser Leu Asp Thr Ser Glu Thr Ser Lys Thr Ser Arg
    50                  55                  60

Leu Ser Phe Lys Glu Asn Val Val Met Val Thr Ala Asn Gly Lys Ile
65                  70                  75                  80

Leu Lys Lys Arg Arg Leu Ser Leu Asn Gln Phe Ile Thr Asp Asp Asp
                85                  90                  95

Leu Glu Ala Ile Ala Asn Asp Thr Glu Glu Ile Ile Lys Pro Arg
            100                 105                 110

Ser Ala His Tyr Ser Phe Gln Ser Asn Val Lys Tyr Asn Phe Met Arg
        115                 120                 125

Val Ile His Gln Glu Cys Ile Leu Asn Asp Ala Leu Asn Gln Ser Ile
    130                 135                 140

Ile Arg Asp Met Ser Gly Pro Tyr Met Thr Ala Thr Leu Asn Asn
145                 150                 155                 160

Leu Glu Glu Ala Val Lys Phe Asp Met Val Ala Tyr Val Ser Glu Glu
                165                 170                 175

Asp Ser Gln Leu Pro Val Thr Leu Arg Ile Ser Lys Thr Gln Leu Phe
            180                 185                 190

Val Ser Ala Gln Asn Glu Asp Glu Pro Val Leu His Lys Glu Met Pro
        195                 200                 205

Glu Thr Pro Lys Ile Ile Lys Asp Glu Thr Asn Leu Leu Phe Phe Trp
    210                 215                 220

Glu Lys His Gly Ser Met Asp Tyr Phe Lys Ser Val Ala His Pro Lys
225                 230                 235                 240

Leu Phe Ile Ala Thr Lys Gln Glu Lys Leu Val His Met Ala Ser Gly
                245                 250                 255

Pro Pro Ser Ile Thr Asp Phe Leu Ile Leu Glu Lys
            260                 265
```

<210> SEQ ID NO 18
<211> LENGTH: 268
<212> TYPE: PRT
<213> ORGANISM: Oryctolagus spp. (rabbit)

<400> SEQUENCE: 18

```
Met Ala Lys Val Pro Asp Leu Phe Glu Asp Leu Lys Asn Cys Phe Ser
1               5                   10                  15

Glu Asn Glu Glu Tyr Ser Ser Ala Ile Asp His Leu Ser Leu Asn Gln
            20                  25                  30

Lys Ser Phe Tyr Asp Ala Ser Tyr Glu Pro Leu His Glu Asp Cys Met
        35                  40                  45

Asn Lys Val Val Ser Leu Ser Thr Ser Glu Thr Ser Val Ser Pro Asn
    50                  55                  60

Leu Thr Phe Gln Glu Asn Val Val Ala Val Thr Ala Ser Gly Lys Ile
65                  70                  75                  80

Leu Lys Lys Arg Arg Leu Ser Leu Asn Gln Pro Ile Thr Asp Val Asp
```

-continued

```
                85                  90                  95
Leu Glu Thr Asn Val Ser Asp Pro Glu Gly Ile Ile Lys Pro Arg
            100                 105                 110
Ser Val Pro Tyr Thr Phe Gln Arg Asn Met Arg Tyr Lys Tyr Leu Arg
            115                 120                 125
Ile Ile Lys Gln Glu Phe Thr Leu Asn Asp Ala Leu Asn Gln Ser Leu
    130                 135                 140
Val Arg Asp Thr Ser Asp Gln Tyr Leu Arg Ala Ala Pro Leu Gln Asn
145                 150                 155                 160
Leu Gly Asp Ala Val Lys Phe Asp Met Gly Val Tyr Met Thr Ser Lys
                165                 170                 175
Glu Asp Ser Ile Leu Pro Val Thr Leu Arg Ile Ser Gln Thr Pro Leu
            180                 185                 190
Phe Val Ser Ala Gln Asn Glu Asp Glu Pro Val Leu Leu Lys Glu Met
            195                 200                 205
Pro Glu Thr Pro Arg Ile Ile Thr Asp Ser Glu Ser Asp Ile Leu Phe
            210                 215                 220
Phe Trp Glu Thr Gln Gly Asn Lys Asn Tyr Phe Lys Ser Ala Ala Asn
225                 230                 235                 240
Pro Gln Leu Phe Ile Ala Thr Lys Pro Glu His Leu Val His Met Ala
                245                 250                 255
Arg Gly Leu Pro Ser Met Thr Asp Phe Gln Ile Ser
                260                 265

<210> SEQ ID NO 19
<211> LENGTH: 270
<212> TYPE: PRT
<213> ORGANISM: Rattus sp.

<400> SEQUENCE: 19

Met Ala Lys Val Pro Asp Leu Phe Glu Asp Leu Lys Asn Cys Tyr Ser
  1               5                  10                  15
Glu Asn Glu Glu Tyr Ser Ser Ala Ile Asp His Leu Ser Leu Asn Gln
            20                  25                  30
Lys Ser Phe Tyr Asp Ala Ser Tyr Gly Ser Leu His Glu Asn Cys Thr
        35                  40                  45
Asp Lys Phe Val Ser Leu Arg Thr Ser Glu Thr Ser Lys Met Ser Thr
    50                  55                  60
Phe Thr Phe Lys Glu Ser Arg Val Val Ser Ala Thr Ser Asn Lys
65                  70                  75                  80
Gly Lys Ile Leu Lys Lys Arg Leu Ser Phe Asn Gln Pro Phe Thr
                85                  90                  95
Glu Asp Asp Leu Glu Ala Ile Ala His Asp Leu Glu Glu Thr Ile Gln
            100                 105                 110
Pro Arg Ser Ala Pro His Ser Phe Gln Asn Asn Leu Arg Tyr Lys Leu
            115                 120                 125
Ile Arg Ile Val Lys Gln Glu Phe Ile Met Asn Asp Ser Leu Asn Gln
    130                 135                 140
Asn Ile Tyr Val Asp Met Asp Arg Ile His Leu Lys Ala Ala Ser Leu
145                 150                 155                 160
Asn Asp Leu Gln Leu Glu Val Lys Phe Asp Met Tyr Ala Tyr Ser Ser
                165                 170                 175
Gly Gly Asp Asp Ser Lys Tyr Pro Val Thr Leu Lys Val Ser Asn Thr
            180                 185                 190
```

```
Gln Leu Phe Val Ser Ala Gln Gly Glu Asp Lys Pro Val Leu Leu Lys
            195                 200                 205

Glu Ile Pro Glu Thr Pro Lys Leu Ile Thr Gly Ser Glu Thr Asp Leu
            210                 215                 220

Ile Phe Phe Trp Glu Lys Ile Asn Ser Lys Asn Tyr Phe Thr Ser Ala
225                 230                 235                 240

Ala Phe Pro Glu Leu Leu Ile Ala Thr Lys Glu Gln Ser Gln Val His
            245                 250                 255

Leu Ala Arg Gly Leu Pro Ser Met Ile Asp Phe Gln Ile Ser
            260                 265                 270

<210> SEQ ID NO 20
<211> LENGTH: 270
<212> TYPE: PRT
<213> ORGANISM: Sus spp.

<400> SEQUENCE: 20

Met Ala Lys Val Pro Asp Leu Phe Glu Asp Leu Lys Asn Cys Tyr Ser
  1               5                  10                  15

Glu Asn Glu Glu Tyr Ser Ser Asp Ile Asp His Leu Ser Leu Asn Gln
             20                  25                  30

Lys Ser Phe Tyr Asp Ala Ser Tyr Glu Pro Leu Pro Gly Asp Gly Met
         35                  40                  45

Asp Lys Phe Met Pro Leu Ser Thr Ser Lys Thr Ser Lys Thr Ser Arg
 50                  55                  60

Leu Asn Phe Lys Asp Ser Val Val Met Ala Ala Asn Gly Lys Ile
65                   70                  75                  80

Leu Lys Lys Arg Arg Leu Ser Leu Ile Gln Phe Ile Thr Asp Asp
             85                  90                  95

Leu Glu Ala Ile Ala Asn Asp Thr Glu Glu Ile Ile Lys Pro Arg
            100                 105                 110

Ser Ala Thr Tyr Ser Phe Gln Ser Asn Met Lys Tyr Asn Phe Met Arg
            115                 120                 125

Val Ile Asn His Gln Cys Ile Leu Asn Asp Ala Arg Asn Gln Ser Ile
130                 135                 140

Ile Arg Asp Pro Ser Gly Gln Tyr Leu Met Ala Ala Val Leu Asn Asn
145                 150                 155                 160

Leu Asp Glu Ala Val Lys Phe Asp Met Ala Ala Tyr Thr Ser Asn Asp
            165                 170                 175

Asp Ser Gln Leu Pro Val Thr Leu Arg Ile Ser Glu Thr Arg Leu Phe
            180                 185                 190

Val Ser Ala Gln Asn Glu Asp Glu Pro Val Leu Leu Lys Glu Leu Pro
            195                 200                 205

Glu Thr Pro Lys Thr Ile Lys Asp Glu Thr Ser Leu Leu Phe Phe Trp
            210                 215                 220

Glu Lys His Gly Asn Met Asp Tyr Phe Lys Ser Ala Ala His Pro Lys
225                 230                 235                 240

Leu Leu Ile Ala Thr Arg Gln Glu Lys Leu Val His Met Ala Arg Gly
            245                 250                 255

Leu Pro Ser Val Thr Asp Phe Gln Ile Leu Glu Asn Gln Ser
            260                 265                 270

<210> SEQ ID NO 21
<211> LENGTH: 59
<212> TYPE: PRT
<213> ORGANISM: Homo sapiens
```

```
<400> SEQUENCE: 21

Met Ser Ser Val Val Gly Ala Pro Lys Lys Arg Lys Val Asp Ala
  1               5                  10                  15

Thr Asn Gly Lys Val Leu Lys Lys Arg Arg Leu Ser Leu Ser Gln Ser
                20                  25                  30

Ile Thr Asp Asp Asp Leu Glu Ala Ile Ala Asn Asp Ser Glu Glu Glu
            35                  40                  45

Ile Ile Lys Pro Arg Ser Ala Pro Phe Ser Phe
        50                  55

<210> SEQ ID NO 22
<211> LENGTH: 49
<212> TYPE: PRT
<213> ORGANISM: Homo sapiens

<400> SEQUENCE: 22

Met Ser Ser Val Val Gly Ala Pro Lys Lys Arg Lys Val Asp Ala
  1               5                  10                  15

Thr Asn Gly Lys Val Leu Lys Lys Arg Arg Leu Ser Leu Ser Gln Ser
                20                  25                  30

Ile Thr Asp Asp Asp Leu Glu Ala Ile Ala Asn Asp Ser Glu Glu Glu
            35                  40                  45

Ile

<210> SEQ ID NO 23
<211> LENGTH: 80
<212> TYPE: PRT
<213> ORGANISM: Artificial Sequence
<220> FEATURE:
<223> OTHER INFORMATION: Fusion protein

<400> SEQUENCE: 23

Met Ser Ser Val Val Gly Ala Pro Lys Lys Arg Lys Val Asp Ala
  1               5                  10                  15

Thr Asn Gly Lys Val Leu Lys Lys Arg Arg Leu Ser Leu Ser Gln Ser
                20                  25                  30

Ile Thr Asp Asp Asp Leu Glu Ala Ile Ala Asn Asp Ser Glu Glu Glu
            35                  40                  45

Ile Leu Asp Leu Lys Ala Leu Lys Glu Lys Leu Lys Ala Leu Glu Glu
        50                  55                  60

Lys Leu Lys Ala Leu Glu Glu Lys Leu Lys Ala Leu Val Gly Glu Arg
 65                  70                  75                  80

<210> SEQ ID NO 24
<211> LENGTH: 90
<212> TYPE: PRT
<213> ORGANISM: Artificial Sequence
<220> FEATURE:
<223> OTHER INFORMATION: Fusion protein

<400> SEQUENCE: 24

Met Ser Ser Val Val Gly Ala Pro Lys Lys Arg Lys Val Asp Ala
  1               5                  10                  15

Thr Asn Gly Lys Val Leu Lys Lys Arg Arg Leu Ser Leu Ser Gln Ser
                20                  25                  30

Ile Thr Asp Asp Asp Leu Glu Ala Ile Ala Asn Asp Ser Glu Glu Glu
            35                  40                  45

Ile Ile Lys Pro Arg Ser Ala Pro Phe Ser Phe Leu Asp Leu Lys Ala
```

```
                50                  55                  60
Leu Lys Glu Lys Leu Lys Ala Leu Glu Glu Lys Leu Lys Ala Leu Glu
 65                  70                  75                  80

Glu Lys Leu Lys Ala Leu Val Gly Glu Arg
                 85                  90

<210> SEQ ID NO 25
<211> LENGTH: 149
<212> TYPE: PRT
<213> ORGANISM: Artificial Sequence
<220> FEATURE:
<223> OTHER INFORMATION: Fusion protein

<400> SEQUENCE: 25

Met Ala Lys Val Pro Asp Met Phe Glu Asp Leu Lys Asn Cys Tyr Ser
 1               5                  10                  15

Glu Asn Glu Glu Asp Ser Ser Ser Ile Asp His Leu Ser Leu Asn Gln
                20                  25                  30

Lys Ser Phe Tyr His Val Ser Tyr Gly Pro Leu His Glu Gly Cys Met
             35                  40                  45

Asp Gln Ser Val Ser Leu Ser Ile Ser Glu Thr Ser Lys Thr Ser Lys
         50                  55                  60

Leu Thr Phe Lys Glu Ser Met Val Val Ala Thr Asn Gly Lys Val
 65                  70                  75                  80

Leu Lys Lys Arg Arg Leu Ser Leu Ser Gln Ser Ile Thr Asp Asp Asp
                 85                  90                  95

Leu Glu Ala Ile Ala Asn Asp Ser Glu Glu Ile Ile Lys Pro Arg
                100                 105                 110

Ser Ala Pro Phe Ser Phe Leu Asp Leu Lys Ala Leu Lys Glu Lys Leu
             115                 120                 125

Lys Ala Leu Glu Glu Lys Leu Lys Ala Leu Glu Glu Lys Leu Lys Ala
         130                 135                 140

Leu Val Gly Glu Arg
145

<210> SEQ ID NO 26
<211> LENGTH: 139
<212> TYPE: PRT
<213> ORGANISM: Artificial Sequence
<220> FEATURE:
<223> OTHER INFORMATION: Fusion protein

<400> SEQUENCE: 26

Met Ala Lys Val Pro Asp Met Phe Glu Asp Leu Lys Asn Cys Tyr Ser
 1               5                  10                  15

Glu Asn Glu Glu Asp Ser Ser Ser Ile Asp His Leu Ser Leu Asn Gln
                20                  25                  30

Lys Ser Phe Tyr His Val Ser Tyr Gly Pro Leu His Glu Gly Cys Met
             35                  40                  45

Asp Gln Ser Val Ser Leu Ser Ile Ser Glu Thr Ser Lys Thr Ser Lys
         50                  55                  60

Leu Thr Phe Lys Glu Ser Met Val Val Ala Thr Asn Gly Lys Val
 65                  70                  75                  80

Leu Lys Lys Arg Arg Leu Ser Leu Ser Gln Ser Ile Thr Asp Asp Asp
                 85                  90                  95

Leu Glu Ala Ile Ala Asn Asp Ser Glu Glu Ile Leu Asp Leu Lys
                100                 105                 110
```

```
Ala Leu Lys Glu Lys Leu Lys Ala Leu Glu Glu Lys Leu Lys Ala Leu
        115                 120                 125
Glu Glu Lys Leu Lys Ala Leu Val Gly Glu Arg
    130                 135
```

<210> SEQ ID NO 27
<211> LENGTH: 86
<212> TYPE: PRT
<213> ORGANISM: Artificial Sequence
<220> FEATURE:
<223> OTHER INFORMATION: Fusion protein

<400> SEQUENCE: 27

```
Met Ser Ile Ser Glu Thr Ser Lys Thr Ser Lys Leu Thr Phe Lys Glu
 1               5                  10                  15
Ser Met Val Val Val Ala Thr Asn Gly Lys Val Leu Lys Lys Arg Arg
                20                  25                  30
Leu Ser Leu Ser Gln Ser Ile Thr Asp Asp Leu Glu Ala Ile Ala
            35                  40                  45
Asn Asp Ser Glu Glu Glu Ile Leu Asp Leu Lys Ala Leu Lys Glu Lys
    50                  55                  60
Leu Lys Ala Leu Glu Glu Lys Leu Lys Ala Leu Glu Glu Lys Leu Lys
65                  70                  75                  80
Ala Leu Val Gly Glu Arg
                85
```

<210> SEQ ID NO 28
<211> LENGTH: 10
<212> TYPE: PRT
<213> ORGANISM: Homo sapiens

<400> SEQUENCE: 28

```
Asn Gly Lys Val Leu Lys Lys Arg Arg Leu
 1               5                  10
```

<210> SEQ ID NO 29
<211> LENGTH: 4
<212> TYPE: PRT
<213> ORGANISM: Homo sapiens

<400> SEQUENCE: 29

```
Lys Lys Arg Arg
 1
```

<210> SEQ ID NO 30
<211> LENGTH: 7
<212> TYPE: PRT
<213> ORGANISM: Artificial Sequence
<220> FEATURE:
<223> OTHER INFORMATION: Synthetic nuclear localization signal sequence

<400> SEQUENCE: 30

```
Pro Lys Lys Lys Arg Lys Val
 1               5
```

<210> SEQ ID NO 31
<211> LENGTH: 516
<212> TYPE: DNA
<213> ORGANISM: Mesocricetus auratus
<220> FEATURE:
<221> NAME/KEY: CDS
<222> LOCATION: (1)...(516)

<400> SEQUENCE: 31

```
agt cag aaa tcc ttc tac gat gca agc tat ggg tca ctc cat gag aac      48
Ser Gln Lys Ser Phe Tyr Asp Ala Ser Tyr Gly Ser Leu His Glu Asn
 1               5                  10                  15 tgc aca gat aaa ttt gta tct ctg aga acc tct gaa acc tca aag atg      96
Cys Thr Asp Lys Phe Val Ser Leu Arg Thr Ser Glu Thr Ser Lys Met
             20                  25                  30 tcc agc tta acc ttt gaa gag agc cta gtg atg gtg gca gca aca tcc     144
Ser Ser Leu Thr Phe Glu Glu Ser Leu Val Met Val Ala Ala Thr Ser
         35                  40                  45 gac aaa ggg aag att ctg aag aag aga cga ctg ggt ttc aat cag gcc     192
Asp Lys Gly Lys Ile Leu Lys Lys Arg Arg Leu Gly Phe Asn Gln Ala
 50                  55                  60 ttt gcc gaa gat gac ctg gag acc ata acc cgc aat tta gaa gag acc     240
Phe Ala Glu Asp Asp Leu Glu Thr Ile Thr Arg Asn Leu Glu Glu Thr
 65                  70                  75                  80 atc caa tca gat tca gca cct tac gtc ttc cag agc aat atg aga tac     288
Ile Gln Ser Asp Ser Ala Pro Tyr Val Phe Gln Ser Asn Met Arg Tyr
                 85                  90                  95 aaa ctg ata agg cga gtc atg cag gag ttc gtc ctg aat gat tcc ctc     336
Lys Leu Ile Arg Arg Val Met Gln Glu Phe Val Leu Asn Asp Ser Leu
            100                 105                 110 aat caa aat atc tac ctg gat gca gac caa gtg cat ctc aaa gca gct     384
Asn Gln Asn Ile Tyr Leu Asp Ala Asp Gln Val His Leu Lys Ala Ala
        115                 120                 125 tcg tta aat gac ctg caa cat gaa gta aaa ttt gac atg tat gtc tac     432
Ser Leu Asn Asp Leu Gln His Glu Val Lys Phe Asp Met Tyr Val Tyr
130                 135                 140 tcg tca gaa gac gac tct aaa tat cct gtt act cta aaa atc tcg aat     480
Ser Ser Glu Asp Asp Ser Lys Tyr Pro Val Thr Leu Lys Ile Ser Asn
145                 150                 155                 160 act cag ctg ttt gtg agt gct cag ggt gaa gac cag                     516
Thr Gln Leu Phe Val Ser Ala Gln Gly Glu Asp Gln
                165                 170

<210> SEQ ID NO 32
<211> LENGTH: 172
<212> TYPE: PRT
<213> ORGANISM: Mesocricetus auratus

<400> SEQUENCE: 32

Ser Gln Lys Ser Phe Tyr Asp Ala Ser Tyr Gly Ser Leu His Glu Asn
 1               5                  10                  15

Cys Thr Asp Lys Phe Val Ser Leu Arg Thr Ser Glu Thr Ser Lys Met
             20                  25                  30

Ser Ser Leu Thr Phe Glu Glu Ser Leu Val Met Val Ala Ala Thr Ser
         35                  40                  45

Asp Lys Gly Lys Ile Leu Lys Lys Arg Arg Leu Gly Phe Asn Gln Ala
 50                  55                  60

Phe Ala Glu Asp Asp Leu Glu Thr Ile Thr Arg Asn Leu Glu Glu Thr
 65                  70                  75                  80

Ile Gln Ser Asp Ser Ala Pro Tyr Val Phe Gln Ser Asn Met Arg Tyr
                 85                  90                  95

Lys Leu Ile Arg Arg Val Met Gln Glu Phe Val Leu Asn Asp Ser Leu
            100                 105                 110

Asn Gln Asn Ile Tyr Leu Asp Ala Asp Gln Val His Leu Lys Ala Ala
        115                 120                 125

Ser Leu Asn Asp Leu Gln His Glu Val Lys Phe Asp Met Tyr Val Tyr
130                 135                 140
```

Ser Ser Glu Asp Asp Ser Lys Tyr Pro Val Thr Leu Lys Ile Ser Asn
145                 150                 155                 160

Thr Gln Leu Phe Val Ser Ala Gln Gly Glu Asp Gln
                165                 170

<210> SEQ ID NO 33
<211> LENGTH: 2014
<212> TYPE: DNA
<213> ORGANISM: Rattus sp.

<400> SEQUENCE: 33

| | | | | | |
|---|---|---|---|---|---|
| aaagtctcca | gggcacagag | ggagtcaact | cattggcgct | tgagtcggca | aagaaatcaa | 60 |
| gatggccaaa | gttcctgact | tgtttgaaga | cctaaagaac | tgctatagtg | aaaatgaaga | 120 |
| atacagttct | gccattgacc | atctgtctct | gaatcagaaa | tccttctatg | atgcaagcta | 180 |
| tggctcactt | catgagaact | gcacagataa | atttgtatct | ctgagaacct | ctgaaacatc | 240 |
| aaagatgtcc | accttcacct | tcaaggagag | ccgggtggtg | gtgtcagcaa | catcaaacaa | 300 |
| agggaagatt | ctgaagaaga | gacggctaag | tttcaatcag | cccttactg | aagatgacct | 360 |
| ggaggccata | gcccatgatt | tagaagagac | catccaaccc | agatcagcac | ctcacagctt | 420 |
| ccagaataat | ttgagataca | aattgataag | gatcgtcaag | caggagttca | tcatgaatga | 480 |
| ttccctcaac | caaaatatat | atgtggatat | ggacagaata | catctcaaag | ctgcttcgtt | 540 |
| aaatgacctg | cagcttgaag | taaaatttga | catgtatgcc | tactcatcgg | aggagacga | 600 |
| ctctaaatat | cctgtgactc | tcaaagtctc | aaatactcag | ctctttgtga | gtgctcaggg | 660 |
| agaagacaag | cctgtgttgc | tgaaggagat | tccggaaaca | ccaaaactca | tcacaggtag | 720 |
| tgagaccgac | ctcattttct | tctggaaaa | aatcaactct | aagaactact | tcacatccgc | 780 |
| agctttcca | gagctgttaa | ttgccacaaa | agaacaaagt | caggtgcacc | tggcacgggg | 840 |
| actgccctcc | atgatagatt | tccagatatc | ataaaaacag | ccttatttag | gagtctactt | 900 |
| tcttgagaag | tgctgacaat | ctgtatgtac | catgtacagg | aaatgttcct | cgtcctaagt | 960 |
| cactcgcatg | gcatgtgctg | agtctttgta | attctaaatg | aatgtttacc | ctctttgtaa | 1020 |
| gagaagagca | aagcctagtg | gaaccagccc | gacatatgat | actgtttgtt | atttaaagag | 1080 |
| taccctatag | tttgctcact | actaatcatt | ttaattatta | ttcttcatgg | tattcttagg | 1140 |
| agggtcaaaa | agactctgct | catattacag | atgggctaac | taagggataa | gacaactgaa | 1200 |
| aagtacactc | aattgcatct | ggaatgggaa | ttcacagacc | catgaaactt | atctcactgt | 1260 |
| gcaccttctg | cttctaaagt | gccggatggg | taggataaag | ttgtaagaac | gtaatgctat | 1320 |
| cattttcaaa | aggaagggga | caatagctac | atctttccta | cctcagtggg | ttttattcca | 1380 |
| gtaagagcat | ttggataaaa | tccttctgta | acagacctca | agaaggagac | agactgttga | 1440 |
| atgttatttt | taagttattt | tatatatgta | tttataaata | tatttatgat | aattatatta | 1500 |
| tttatggcac | atccttaaat | cctctgagct | tgccaggcat | cctcagcagc | agaattttct | 1560 |
| aggtggtcag | ttagatgcag | tgtcctctga | acaccatgc | tatagacaga | cgtacactgt | 1620 |
| ttccacatcc | gtggagctct | ctttacattc | ttgtccttag | gagccctgca | gtcatgatca | 1680 |
| ccaatctgta | ctgttcactt | cgttcattta | aaatgataac | tgggtcagtc | ttttgccctc | 1740 |
| ctgtccttaa | agctgtctgg | gtcttcttac | atcattcaac | tcacctgtaa | ttaaagctaa | 1800 |
| ccatctaaag | acgggaagaa | cctaactgtg | acaaccacat | ccctgttacc | tgaagtttct | 1860 |
| tttctaggat | gtaatcagtg | tttcctctgg | gttccaaatt | tgttctcaaa | ccagggtgtc | 1920 |

| | |
|---|---|
| acaaaaatat caacaataat aatcaactca tcattactat tgatcataat taaataaagc | 1980 |
| aagtttgagc tgaaaaaaaa aaaaaaaaaa aaaa | 2014 |

<210> SEQ ID NO 34
<211> LENGTH: 1330
<212> TYPE: DNA
<213> ORGANISM: Mus spp.

<400> SEQUENCE: 34

| | |
|---|---|
| tcgaggccta ataggctcat ctgggatcct ctccagccaa gcttccttgt gcaagtgtct | 60 |
| gaagcagcta tggcaactgt tcctgaactc aactgtgaaa tgccacctttt tgacagtgat | 120 |
| gagaatgacc tgttctttga agttgacgga ccccaaaaga tgaagggctg cttccaaacc | 180 |
| tttgacctgg gctgtccaga tgagagcatc cagcttcaaa tctcacagca gcacatcaac | 240 |
| aagagcttca ggcaggcagt atcactcatt gtggctgtgg agaagctgtg gcagctacct | 300 |
| gtgtctttcc cgtggacctt ccaggatgag gacatgagca ccttcttttc cttcatctttt | 360 |
| gaagaagagc ccatcctctg tgactcatgg gatgatgatg ataacctgct ggtgtgtgac | 420 |
| gttcccatta gacagctgca ctacaggctc gagatgaac aacaaaaaag cctcgtgctg | 480 |
| tcggacccat atgagctgaa agctctccac ctcaatggac agaatatcaa ccaacaagtg | 540 |
| atattctcca tgagctttgt acaaggagaa ccaagcaacg acaaaatacc tgtggccttg | 600 |
| ggcctcaaag gaaagaatct atacctgtcc tgtgtaatga agacggcac acccaccctg | 660 |
| cagctggaga gtgtggatcc caagcaatac ccaaagaaga gatggaaaa gcggtttgtc | 720 |
| ttcaacaaga tagaagtcaa gagcaaagtg gagtttgagt ctgcagagtt ccccaactgg | 780 |
| tacatcagca cctcacaagc agagcacaag cctgtcttcc tgggaaacaa cagtggtcag | 840 |
| gacataattg acttcaccat ggaatctgtg tcttcctaaa gtatgggctg gactgtttct | 900 |
| aatgccttcc ccagggcatg tgaaggagct cccttgtcat gaatgagcag acagctcaat | 960 |
| ctctaggaca ctccttagtc ctcggccaag acaggtcgct cagggtcaca agaaaccatg | 1020 |
| gcacattctg ttcaaagaga gcctgtgtttt tcctccttgc ctctgatggg caaccactta | 1080 |
| cctatttatt tatgtatttta ttgattggtt gatctattta agttgattca aggggacatt | 1140 |
| aggcagcact ctctagaaca gaacctagct gtcaacgtgt gggggatgaa ttggtcatag | 1200 |
| cctgcactga ggtctttcat tgaagctgag aataaatagg ttcctataat atggatgaga | 1260 |
| attttttatga atgaagcaca gacacttgct ttgatgagta tgaaataaat ttcattaaaa | 1320 |
| caaacaaaca | 1330 |

<210> SEQ ID NO 35
<211> LENGTH: 823
<212> TYPE: DNA
<213> ORGANISM: Macaca fascicularis
<220> FEATURE:
<221> NAME/KEY: CDS
<222> LOCATION: (7)...(819)

<400> SEQUENCE: 35

| | |
|---|---|
| gtcaag atg gcc aaa gtt ccg gac atg ttt gaa gac ctg aag aac tgt | 48 |
|       Met Ala Lys Val Pro Asp Met Phe Glu Asp Leu Lys Asn Cys | |
|       1          5              10 | |
| tac agt gaa aat gaa gaa gtc agt tcc tcc att gac cat ctg tct ctg | 96 |
| Tyr Ser Glu Asn Glu Glu Val Ser Ser Ser Ile Asp His Leu Ser Leu | |
| 15            20            25            30 | |
| aat cag aaa tcc ttc tat gat gta agc tat ggc cca ctc cat gaa ggc | 144 |
| Asn Gln Lys Ser Phe Tyr Asp Val Ser Tyr Gly Pro Leu His Glu Gly | |

```
                          35                  40                  45
tgc atg gat cag tct gtg tcc ctg agt atc tct gaa atc tct aaa aca        192
Cys Met Asp Gln Ser Val Ser Leu Ser Ile Ser Glu Ile Ser Lys Thr
             50                  55                  60 tcc aag ctg acc ttc aag cag agc atg gtg gta gta tca acc aat ggg        240
Ser Lys Leu Thr Phe Lys Gln Ser Met Val Val Val Ser Thr Asn Gly
             65                  70                  75 aag gtt ctg aag aag aga cgg ttg agt tta agc cag tcc atc act gat        288
Lys Val Leu Lys Lys Arg Arg Leu Ser Leu Ser Gln Ser Ile Thr Asp
 80                  85                  90 aat aac ctg gag gcc atc gcc aac gac tca gag gaa gaa atc atc aag        336
Asn Asn Leu Glu Ala Ile Ala Asn Asp Ser Glu Glu Glu Ile Ile Lys
 95                 100                 105                 110 ccc agg tcg gca cct ttt agc ttc cta agc aat atg aca tac cac ttt        384
Pro Arg Ser Ala Pro Phe Ser Phe Leu Ser Asn Met Thr Tyr His Phe
                115                 120                 125 ata agg atc atc aaa cac gaa ttc atc ctg aat gac acc ctc aat caa        432
Ile Arg Ile Ile Lys His Glu Phe Ile Leu Asn Asp Thr Leu Asn Gln
            130                 135                 140 act ata att cga gcc aat gat cag tac ctc acg gct gct gca ata cat        480
Thr Ile Ile Arg Ala Asn Asp Gln Tyr Leu Thr Ala Ala Ala Ile His
            145                 150                 155 aat ctg gat gaa gca gtg aaa ttt gac atg ggt gct tat acg tca tca        528
Asn Leu Asp Glu Ala Val Lys Phe Asp Met Gly Ala Tyr Thr Ser Ser
160                 165                 170 aag gat gat act aaa gtt cct gtg att cta aga atc tca aaa act caa        576
Lys Asp Asp Thr Lys Val Pro Val Ile Leu Arg Ile Ser Lys Thr Gln
175                 180                 185                 190 ttg tat gtg agt gcc caa gat gaa gac caa ccg gtg ctg ctg aag gag        624
Leu Tyr Val Ser Ala Gln Asp Glu Asp Gln Pro Val Leu Leu Lys Glu
                195                 200                 205 atg cct gag ata ccc aaa acc atc aca ggt agt gag acc aac ttc ctc        672
Met Pro Glu Ile Pro Lys Thr Ile Thr Gly Ser Glu Thr Asn Phe Leu
            210                 215                 220 ttc ttc tgg gaa act cat ggc act aag aac tac ttc ata tca gtt gcc        720
Phe Phe Trp Glu Thr His Gly Thr Lys Asn Tyr Phe Ile Ser Val Ala
            225                 230                 235 cat cca aac ttg ttt att gcc aca aag cat gac aat tgg gtg tgc ttg        768
His Pro Asn Leu Phe Ile Ala Thr Lys His Asp Asn Trp Val Cys Leu
            240                 245                 250 gca aag ggg cta ccc tct atc act gac ttt cag ata ctg gaa aac cag        816
Ala Lys Gly Leu Pro Ser Ile Thr Asp Phe Gln Ile Leu Glu Asn Gln
255                 260                 265                 270 gct tagg                                                               823
Ala

<210> SEQ ID NO 36
<211> LENGTH: 271
<212> TYPE: PRT
<213> ORGANISM: Macaca fascicularis

<400> SEQUENCE: 36

Met Ala Lys Val Pro Asp Met Phe Glu Asp Leu Lys Asn Cys Tyr Ser
 1               5                  10                  15

Glu Asn Glu Glu Val Ser Ser Ser Ile Asp His Leu Ser Leu Asn Gln
            20                  25                  30

Lys Ser Phe Tyr Asp Val Ser Tyr Gly Pro Leu His Glu Gly Cys Met
        35                  40                  45

Asp Gln Ser Val Ser Leu Ser Ile Ser Glu Ile Ser Lys Thr Ser Lys
```

-continued

```
                50                  55                  60
Leu Thr Phe Lys Gln Ser Met Val Val Ser Thr Asn Gly Lys Val
 65                  70                  75                  80

Leu Lys Lys Arg Arg Leu Ser Leu Ser Gln Ser Ile Thr Asp Asn Asn
                 85                  90                  95

Leu Glu Ala Ile Ala Asn Asp Ser Glu Glu Ile Ile Lys Pro Arg
                100                 105                 110

Ser Ala Pro Phe Ser Phe Leu Ser Asn Met Thr Tyr His Phe Ile Arg
                115                 120                 125

Ile Ile Lys His Glu Phe Ile Leu Asn Asp Thr Leu Asn Gln Thr Ile
            130                 135                 140

Ile Arg Ala Asn Asp Gln Tyr Leu Thr Ala Ala Ile His Asn Leu
145                 150                 155                 160

Asp Glu Ala Val Lys Phe Asp Met Gly Ala Tyr Thr Ser Ser Lys Asp
                165                 170                 175

Asp Thr Lys Val Pro Val Ile Leu Arg Ile Ser Lys Thr Gln Leu Tyr
                180                 185                 190

Val Ser Ala Gln Asp Glu Asp Gln Pro Val Leu Leu Lys Glu Met Pro
            195                 200                 205

Glu Ile Pro Lys Thr Ile Thr Gly Ser Glu Thr Asn Phe Leu Phe Phe
210                 215                 220

Trp Glu Thr His Gly Thr Lys Asn Tyr Phe Ile Ser Val Ala His Pro
225                 230                 235                 240

Asn Leu Phe Ile Ala Thr Lys His Asp Asn Trp Val Cys Leu Ala Lys
                245                 250                 255

Gly Leu Pro Ser Ile Thr Asp Phe Gln Ile Leu Glu Asn Gln Ala
            260                 265                 270
```

<210> SEQ ID NO 37
<211> LENGTH: 1820
<212> TYPE: DNA
<213> ORGANISM: Sus scrofa
<220> FEATURE:
<221> NAME/KEY: CDS
<222> LOCATION: (41)...(850)

<400> SEQUENCE: 37

```
gagtcatctc tttgtcgctc cagccagcac agaagtgaag atg gcc aaa gtc cct      55
                                              Met Ala Lys Val Pro
                                               1               5 gac ctc ttt gaa gac ctg aag aac tgc tac agt gaa aat gaa gaa tac     103
Asp Leu Phe Glu Asp Leu Lys Asn Cys Tyr Ser Glu Asn Glu Glu Tyr
         10                  15                  20 agt tct gat atc gac cat ctc tct ctg aat cag aag tcc ttc tat gat     151
Ser Ser Asp Ile Asp His Leu Ser Leu Asn Gln Lys Ser Phe Tyr Asp
             25                  30                  35 gcc agc tat gag cca ctt cct ggg gac ggc atg gat aaa ttt atg cct     199
Ala Ser Tyr Glu Pro Leu Pro Gly Asp Gly Met Asp Lys Phe Met Pro
         40                  45                  50 ctg agt acc tct aaa acc tct aag aca tcc agg cta aac ttc aag gac     247
Leu Ser Thr Ser Lys Thr Ser Lys Thr Ser Arg Leu Asn Phe Lys Asp
     55                  60                  65 agt gtg gtg atg gca gca gcc aac ggg aag att ctg aag aag aga cgg     295
Ser Val Val Met Ala Ala Ala Asn Gly Lys Ile Leu Lys Lys Arg Arg
 70                  75                  80                  85 ttg agt tta aat cag ttc atc acc gat gac gac ctg gaa gcc att gcc     343
Leu Ser Leu Asn Gln Phe Ile Thr Asp Asp Asp Leu Glu Ala Ile Ala
                 90                  95                 100
```

-continued

| | | |
|---|---|---|
| aat gac aca gaa gaa gaa atc atc aag ccc aga tca gca aca tac agc<br>Asn Asp Thr Glu Glu Glu Ile Ile Lys Pro Arg Ser Ala Thr Tyr Ser<br>105                          110                          115 | | 391 |
| ttc cag agc aac atg aaa tac aac ttc atg agg gtc atc aac cac cag<br>Phe Gln Ser Asn Met Lys Tyr Asn Phe Met Arg Val Ile Asn His Gln<br>          120                          125                          130 | | 439 |
| tgc atc ctg aat gat gcc cgc aat caa agc atc att cga gac ccg tca<br>Cys Ile Leu Asn Asp Ala Arg Asn Gln Ser Ile Ile Arg Asp Pro Ser<br>135                          140                          145 | | 487 |
| ggt caa tac ctc atg gct gct gtg cta aat aac ctg gat gag gca gtg<br>Gly Gln Tyr Leu Met Ala Ala Val Leu Asn Asn Leu Asp Glu Ala Val<br>150                          155                          160                          165 | | 535 |
| aaa ttt gac atg gct gct tat aca tca aat gat gat tcg caa ctt cct<br>Lys Phe Asp Met Ala Ala Tyr Thr Ser Asn Asp Asp Ser Gln Leu Pro<br>          170                          175                          180 | | 583 |
| gtg act cta aga atc tca gaa acc cga ctg ttt gtg agt gct caa aac<br>Val Thr Leu Arg Ile Ser Glu Thr Arg Leu Phe Val Ser Ala Gln Asn<br>185                          190                          195 | | 631 |
| gaa gac gaa ccc gtg ttg ctg aag gag ctg cct gag aca ccc aaa acc<br>Glu Asp Glu Pro Val Leu Leu Lys Glu Leu Pro Glu Thr Pro Lys Thr<br>          200                          205                          210 | | 679 |
| atc aaa gat gag acc agt ctc ctc ttc ttc tgg gaa aag cat ggc aat<br>Ile Lys Asp Glu Thr Ser Leu Leu Phe Phe Trp Glu Lys His Gly Asn<br>215                          220                          225 | | 727 |
| atg gac tac ttc aaa tca gcc gcc cat cca aag ttg ttt att gcc aca<br>Met Asp Tyr Phe Lys Ser Ala Ala His Pro Lys Leu Phe Ile Ala Thr<br>230                          235                          240                          245 | | 775 |
| agg cag gaa aaa ctg gtg cac atg gca ccg ggg ctg ccc tct gtc act<br>Arg Gln Glu Lys Leu Val His Met Ala Pro Gly Leu Pro Ser Val Thr<br>          250                          255                          260 | | 823 |
| gac ttt cag ata ctg gaa aac cag tct tgactctggt gtctacttac<br>Asp Phe Gln Ile Leu Glu Asn Gln Ser<br>265                          270 | | 870 | ctgtgaagtg ttgacaggcc gtatgtacca tgtacatgaa ggagttaaat ctttcactct     930 tagtcactcg ctgagcatgt gctgagcctt tgtaattcta aatgaatgtt tactctcttt     990 gtaagagagg gagcgaagtc tggtagaacc aacactaaca aataacatcg cttagtattt    1050 aaaaaacaca ctgtcattta caaactacca atcattttaa ttattattct gcataacaat    1110 cttgggagga ccagggttac tgactatggc taccaaaaag gttctaccca tattacagat    1170 gggttaacta aggcctgagg atattaagaa gtatccacaa tagcagctgg aatgagaagc    1230 tatggaccca ggatttcatt ccacctgctt acctttttgcc tttaagttgc tgatggaccc    1290 tatataacat tgtaagtttc tggaacctca atttaatctt aaaaatatat atatatacat    1350 atatatacac acacacatac atagcatata catgtacatt atgtatataa tatttattat    1410 tatatctatt atatctatgt aatagattat atctccttcc tgcctcaaca gtattctatg    1470 acagtgagct tgtttagta aaatgcttct tgaagctgag cctccagaag aaggcaaagc    1530 ctgaaatgtt attttaagtt attatttata tatacatatg tatttataat attatttcta    1590 atataagtag aacatatta tatatttatg tccaactcct tgtgatctct gagtatgacc    1650 agtcatcttc aatgatagca gacagtgttt tccaggttga atgagttgga ggtactaagg    1710 cattttgggc caagttgttg tactttttttt atggccatga aggtctgtat ggtagtagct    1770 gggagccctg taattatgat aataaattta cataattaaa aaaaaaaaa              1820

<210> SEQ ID NO 38

<211> LENGTH: 270
<212> TYPE: PRT
<213> ORGANISM: Sus scrofa

<400> SEQUENCE: 38

```
Met Ala Lys Val Pro Asp Leu Phe Glu Asp Leu Lys Asn Cys Tyr Ser
 1               5                  10                  15
Glu Asn Glu Glu Tyr Ser Ser Asp Ile Asp His Leu Ser Leu Asn Gln
            20                  25                  30
Lys Ser Phe Tyr Asp Ala Ser Tyr Glu Pro Leu Pro Gly Asp Gly Met
        35                  40                  45
Asp Lys Phe Met Pro Leu Ser Thr Ser Lys Thr Ser Lys Thr Ser Arg
 50                  55                  60
Leu Asn Phe Lys Asp Ser Val Val Met Ala Ala Asn Gly Lys Ile
 65                  70                  75                  80
Leu Lys Lys Arg Arg Leu Ser Leu Asn Gln Phe Ile Thr Asp Asp
                 85                  90                  95
Leu Glu Ala Ile Ala Asn Asp Thr Glu Glu Ile Ile Lys Pro Arg
                100                 105                 110
Ser Ala Thr Tyr Ser Phe Gln Ser Asn Met Lys Tyr Asn Phe Met Arg
            115                 120                 125
Val Ile Asn His Gln Cys Ile Leu Asn Asp Ala Arg Asn Gln Ser Ile
130                 135                 140
Ile Arg Asp Pro Ser Gly Gln Tyr Leu Met Ala Ala Val Leu Asn Asn
145                 150                 155                 160
Leu Asp Glu Ala Val Lys Phe Asp Met Ala Ala Tyr Thr Ser Asn Asp
                165                 170                 175
Asp Ser Gln Leu Pro Val Thr Leu Arg Ile Ser Glu Thr Arg Leu Phe
            180                 185                 190
Val Ser Ala Gln Asn Glu Asp Glu Pro Val Leu Leu Lys Glu Leu Pro
        195                 200                 205
Glu Thr Pro Lys Thr Ile Lys Asp Glu Thr Ser Leu Leu Phe Phe Trp
210                 215                 220
Glu Lys His Gly Asn Met Asp Tyr Phe Lys Ser Ala Ala His Pro Lys
225                 230                 235                 240
Leu Phe Ile Ala Thr Arg Gln Glu Lys Leu Val His Met Ala Pro Gly
                245                 250                 255
Leu Pro Ser Val Thr Asp Phe Gln Ile Leu Glu Asn Gln Ser
            260                 265                 270
```

<210> SEQ ID NO 39
<211> LENGTH: 1003
<212> TYPE: DNA
<213> ORGANISM: Bos taurus
<220> FEATURE:
<221> NAME/KEY: CDS
<222> LOCATION: (33)...(836)

<400> SEQUENCE: 39

```
tgttgctagc tcggttcagc aaagaagtga ag atg gcc aaa gtc cct gac ctc      53
                                   Met Ala Lys Val Pro Asp Leu
                                    1               5 ttt gaa gac ctg aag aac tgt tac agt gaa aat gaa gac tac agt tct     101
Phe Glu Asp Leu Lys Asn Cys Tyr Ser Glu Asn Glu Asp Tyr Ser Ser
         10                  15                  20 gaa att gac cac ctc tct ctc aat cag aag tcc ttc tat gat gca agc     149
Glu Ile Asp His Leu Ser Leu Asn Gln Lys Ser Phe Tyr Asp Ala Ser
     25                  30                  35
```

```
tat gag cca ctt cgt gag gac cag atg aat aag ttt atg tcc ctg gat      197
Tyr Glu Pro Leu Arg Glu Asp Gln Met Asn Lys Phe Met Ser Leu Asp
 40                  45                  50                  55 acc tcg gaa acc tct aag aca tcc aag ctt agc ttc aag gag aat gtg      245
Thr Ser Glu Thr Ser Lys Thr Ser Lys Leu Ser Phe Lys Glu Asn Val
                 60                  65                  70 gtg atg gtg gca gcc agt ggg aag att ctg aag aag aga cgg ttg agt      293
Val Met Val Ala Ala Ser Gly Lys Ile Leu Lys Lys Arg Arg Leu Ser
                     75                  80                  85 tta aat cag ttc atc acc gat gat gac ctg gaa gcc att gcc aat aat      341
Leu Asn Gln Phe Ile Thr Asp Asp Asp Leu Glu Ala Ile Ala Asn Asn
             90                  95                 100 aca gaa gaa gaa atc atc aag ccc aga tca gca cat tac agc ttc cag      389
Thr Glu Glu Glu Ile Ile Lys Pro Arg Ser Ala His Tyr Ser Phe Gln
        105                 110                 115 agt aac gtg aaa tac aac ttt atg aga gtc atc cac cag gaa tgc atc      437
Ser Asn Val Lys Tyr Asn Phe Met Arg Val Ile His Gln Glu Cys Ile
120                 125                 130                 135 ctg aac gac gcc ctc aat caa agt ata att cga gat atg tca ggt cca      485
Leu Asn Asp Ala Leu Asn Gln Ser Ile Ile Arg Asp Met Ser Gly Pro
                140                 145                 150 tac ctg acg gct act aca tta aat aat ctg gag gag gca gtg aaa ttt      533
Tyr Leu Thr Ala Thr Thr Leu Asn Asn Leu Glu Glu Ala Val Lys Phe
                    155                 160                 165 gac atg gtt gct tat gta tca gaa gag gat tct cag ctt cct gtg act      581
Asp Met Val Ala Tyr Val Ser Glu Glu Asp Ser Gln Leu Pro Val Thr
                        170                 175                 180 cta aga atc tca aaa act caa ctg ttt gtg agt gct caa aat gaa gac      629
Leu Arg Ile Ser Lys Thr Gln Leu Phe Val Ser Ala Gln Asn Glu Asp
            185                 190                 195 gaa ccc gtc ttg cta aag gag atg cct gag aca ccc aaa atc atc aaa      677
Glu Pro Val Leu Leu Lys Glu Met Pro Glu Thr Pro Lys Ile Ile Lys
200                 205                 210                 215 gat gag acc aac ctc ctc ttc ttc tgg gaa aag cat ggc tct atg gac      725
Asp Glu Thr Asn Leu Leu Phe Phe Trp Glu Lys His Gly Ser Met Asp
                    220                 225                 230 tac ttc aaa tca gtt gcc cat cca aag ttg ttt att gcc aca aag caa      773
Tyr Phe Lys Ser Val Ala His Pro Lys Leu Phe Ile Ala Thr Lys Gln
                235                 240                 245 gaa aaa ttg gtg cac atg gca agt ggg ccg ccc tcg atc act gac ttt      821
Glu Lys Leu Val His Met Ala Ser Gly Pro Pro Ser Ile Thr Asp Phe
            250                 255                 260 cag ata ttg gaa aaa tagccttgac tgtgcactct acttacttgt aaagtggtga     876
Gln Ile Leu Glu Lys
        265 ccatccgtat gtactatgta catgaaggag tcgagcccttt cactgttagt cactcgctga   936 gcatgtgctg agctttttgta attctaaatg aatgtttact ctctttgtaa gagagaacac   996 aaagtcc                                                             1003

<210> SEQ ID NO 40
<211> LENGTH: 268
<212> TYPE: PRT
<213> ORGANISM: Bos taurus

<400> SEQUENCE: 40

Met Ala Lys Val Pro Asp Leu Phe Glu Asp Leu Lys Asn Cys Tyr Ser
 1               5                  10                  15

Glu Asn Glu Asp Tyr Ser Ser Glu Ile Asp His Leu Ser Leu Asn Gln
```

```
                 20                  25                  30
Lys Ser Phe Tyr Asp Ala Ser Tyr Glu Pro Leu Arg Glu Asp Gln Met
             35                  40                  45

Asn Lys Phe Met Ser Leu Asp Thr Ser Glu Thr Ser Lys Thr Ser Lys
         50                  55                  60

Leu Ser Phe Lys Glu Asn Val Val Met Val Ala Ala Ser Gly Lys Ile
 65                  70                  75                  80

Leu Lys Lys Arg Arg Leu Ser Leu Asn Gln Phe Ile Thr Asp Asp Asp
                 85                  90                  95

Leu Glu Ala Ile Ala Asn Asn Thr Glu Glu Ile Ile Lys Pro Arg
             100                 105                 110

Ser Ala His Tyr Ser Phe Gln Ser Asn Val Lys Tyr Asn Phe Met Arg
         115                 120                 125

Val Ile His Gln Glu Cys Ile Leu Asn Asp Ala Leu Asn Gln Ser Ile
     130                 135                 140

Ile Arg Asp Met Ser Gly Pro Tyr Leu Thr Ala Thr Thr Leu Asn Asn
145                 150                 155                 160

Leu Glu Glu Ala Val Lys Phe Asp Met Val Ala Tyr Val Ser Glu Glu
                 165                 170                 175

Asp Ser Gln Leu Pro Val Thr Leu Arg Ile Ser Lys Thr Gln Leu Phe
             180                 185                 190

Val Ser Ala Gln Asn Glu Asp Glu Pro Val Leu Leu Lys Glu Met Pro
         195                 200                 205

Glu Thr Pro Lys Ile Ile Lys Asp Glu Thr Asn Leu Leu Phe Phe Trp
     210                 215                 220

Glu Lys His Gly Ser Met Asp Tyr Phe Lys Ser Val Ala His Pro Lys
225                 230                 235                 240

Leu Phe Ile Ala Thr Lys Gln Glu Lys Leu Val His Met Ala Ser Gly
                 245                 250                 255

Pro Pro Ser Ile Thr Asp Phe Gln Ile Leu Glu Lys
             260                 265

<210> SEQ ID NO 41
<211> LENGTH: 1781
<212> TYPE: DNA
<213> ORGANISM: Ovis spp.
<220> FEATURE:
<221> NAME/KEY: CDS
<222> LOCATION: (53)...(856)

<400> SEQUENCE: 41
gagggagcca gtcatctcat tgttgccagc tcggttcagc aaagaagtga ag atg gcc    58
                                                          Met Ala
                                                            1 aaa gtc cct gac ctc ttt gaa gac ctg aag aac tgt tac agt gaa aat    106
Lys Val Pro Asp Leu Phe Glu Asp Leu Lys Asn Cys Tyr Ser Glu Asn
        5                  10                  15 gaa gac tac agt tct gaa att gac cac ctc tct ctg aat cag aag tcc    154
Glu Asp Tyr Ser Ser Glu Ile Asp His Leu Ser Leu Asn Gln Lys Ser
     20                  25                  30 ttc tat gat gca agc tat gag cca ctt cgt gag gac cac atg aat aag    202
Phe Tyr Asp Ala Ser Tyr Glu Pro Leu Arg Glu Asp His Met Asn Lys
 35                  40                  45                  50 ttc atg tcc ctg gat acc tcg gaa acc tct aag aca tcc agg ctt agc    250
Phe Met Ser Leu Asp Thr Ser Glu Thr Ser Lys Thr Ser Arg Leu Ser
             55                  60                  65 ttc aag gag aat gtg gtg atg atg aca gcc aat ggc aag att ctg aag    298
```

-continued

| | | |
|---|---|---|
| Phe Lys Glu Asn Val Val Met Met Thr Ala Asn Gly Lys Ile Leu Lys<br>          70                        75                      80 | | |
| aag aga cgg ttg agt tta aat cag ttc atc acc gat gac gac ctg gaa<br>Lys Arg Arg Leu Ser Leu Asn Gln Phe Ile Thr Asp Asp Asp Leu Glu<br>          85                        90                      95 | 346 |
| gcc att gcc aat gat acc gaa gaa gaa atc atc aag ccc aga tca gca<br>Ala Ile Ala Asn Asp Thr Glu Glu Glu Ile Ile Lys Pro Arg Ser Ala<br>100                   105                      110 | 394 |
| cat tac agc ttc cag agt aac gtg aaa tac aac ttt atg aga gtc atc<br>His Tyr Ser Phe Gln Ser Asn Val Lys Tyr Asn Phe Met Arg Val Ile<br>115                     120                      125                      130 | 442 |
| cac cag gaa tgc atc ctg aac gac gcc ctc aat caa agt ata att cga<br>His Gln Glu Cys Ile Leu Asn Asp Ala Leu Asn Gln Ser Ile Ile Arg<br>                   135                      140                      145 | 490 |
| gat atg tca ggt cca tac ctg acg gct gct aca tta aat aat ctg gag<br>Asp Met Ser Gly Pro Tyr Leu Thr Ala Ala Thr Leu Asn Asn Leu Glu<br>                   150                      155                      160 | 538 |
| gag gca gtg aaa ttt gac atg gtt gct tat gta tca gaa gag gat tct<br>Glu Ala Val Lys Phe Asp Met Val Ala Tyr Val Ser Glu Glu Asp Ser<br>          165                        170                      175 | 586 |
| cag ctt cct gtg act cta aga atc tca aaa act caa ctg ttt gtg agt<br>Gln Leu Pro Val Thr Leu Arg Ile Ser Lys Thr Gln Leu Phe Val Ser<br>180                     185                      190 | 634 |
| gct caa aat gaa gac gaa ccc gtc ttg cta aag gag atg cct gag aca<br>Ala Gln Asn Glu Asp Glu Pro Val Leu Leu Lys Glu Met Pro Glu Thr<br>195                   200                      205                      210 | 682 |
| ccc aaa atc atc aaa gat gag acc aat ctc ctc ttc ttc tgg gaa aag<br>Pro Lys Ile Ile Lys Asp Glu Thr Asn Leu Leu Phe Phe Trp Glu Lys<br>                   215                      220                      225 | 730 |
| cat ggg tct atg gac tac ttc aaa tca gtt gcc cat cca aag ttg ttc<br>His Gly Ser Met Asp Tyr Phe Lys Ser Val Ala His Pro Lys Leu Phe<br>                   230                      235                      240 | 778 |
| att gcc aca aag caa gaa aaa ctg gtg cac atg gca agc ggg ccg ccc<br>Ile Ala Thr Lys Gln Glu Lys Leu Val His Met Ala Ser Gly Pro Pro<br>          245                        250                      255 | 826 |
| tcg atc act gac ttt cag ata ttg gaa aaa tagccttgat tgtgcactct<br>Ser Ile Thr Asp Phe Gln Ile Leu Glu Lys<br>260                   265 | 876 |
| acttacttgc aaagtggtga ccatccgtat gtactatgta catgaaggag tcgaatcctt | 936 |
| cactgttagt cactcgctga gcatgtgctg agcttttgta attctaaatg aatgtttact | 996 |
| ctcttcgtaa gagagaacac aaagtccagt agaaccaaca ctaacatata atgttgcttg | 1056 |
| ttatttaaag aacaccctat actttgcaag ctaccaatca atgtaattat tattctgcgc | 1116 |
| agtagtcttg ggaggactga ggctactatc tgcggctaca aaaggttctt tccatattat | 1176 |
| agatgagtaa actaaggcat aagaatacta ataccaaaaa aaaacacaga atactaatac | 1236 |
| ccatgacagc agttggaata agccgtggac acgatttc attccaactg ctcagctttt | 1296 |
| acttttaagc cgctatgagc cctttatcaa atactgtaag tttctggggt ctcagtttga | 1356 |
| ccttcttcaa aatcaaggta atggtgacta tagccctcct acctcagcag tactttatgc | 1416 |
| caatgagttc atttaagtaa aattttttctt gaagctgagc ctcaggaaga atgcaaagct | 1476 |
| tgaaatatta ttttaagtta ttatttatta ttaatataag tttatattta taagcattat | 1536 |
| ttctaagata ttattatttc taacatatta ttatatttat ggcaattcat tgcaatatct | 1596 |
| tagtatgacc aggtatcgtc aataatagta gacggtgttt tccaggctga gtgagtctga | 1656 |
| ggttcaaagt gcctttgca ttgtcatgaa cttctgtatt ccagtacctg agagccctgt | 1716 |

```
gattatgata ataaatttat attaattgcc ttgaaaaaaa aaaaaaaaaa aaaaaaaaaa    1776
aaaaa                                                                1781
```

<210> SEQ ID NO 42
<211> LENGTH: 268
<212> TYPE: PRT
<213> ORGANISM: Ovis spp.

<400> SEQUENCE: 42

```
Met Ala Lys Val Pro Asp Leu Phe Glu Asp Leu Lys Asn Cys Tyr Ser
 1               5                  10                  15

Glu Asn Glu Asp Tyr Ser Ser Glu Ile Asp His Leu Ser Leu Asn Gln
            20                  25                  30

Lys Ser Phe Tyr Asp Ala Ser Tyr Glu Pro Leu Arg Glu Asp His Met
        35                  40                  45

Asn Lys Phe Met Ser Leu Asp Thr Ser Glu Thr Ser Lys Thr Ser Arg
50                  55                  60

Leu Ser Phe Lys Glu Asn Val Val Met Met Thr Ala Asn Gly Lys Ile
65                  70                  75                  80

Leu Lys Lys Arg Arg Leu Ser Leu Asn Gln Phe Ile Thr Asp Asp Asp
                85                  90                  95

Leu Glu Ala Ile Ala Asn Asp Thr Glu Glu Ile Ile Lys Pro Arg
            100                 105                 110

Ser Ala His Tyr Ser Phe Gln Ser Asn Val Lys Tyr Asn Phe Met Arg
        115                 120                 125

Val Ile His Gln Glu Cys Ile Leu Asn Asp Ala Leu Asn Gln Ser Ile
    130                 135                 140

Ile Arg Asp Met Ser Gly Pro Tyr Leu Thr Ala Thr Leu Asn Asn
145                 150                 155                 160

Leu Glu Glu Ala Val Lys Phe Asp Met Val Ala Tyr Val Ser Glu Glu
                165                 170                 175

Asp Ser Gln Leu Pro Val Thr Leu Arg Ile Ser Lys Thr Gln Leu Phe
            180                 185                 190

Val Ser Ala Gln Asn Glu Asp Glu Pro Val Leu Leu Lys Glu Met Pro
        195                 200                 205

Glu Thr Pro Lys Ile Ile Lys Asp Glu Thr Asn Leu Leu Phe Phe Trp
    210                 215                 220

Glu Lys His Gly Ser Met Asp Tyr Phe Lys Ser Val Ala His Pro Lys
225                 230                 235                 240

Leu Phe Ile Ala Thr Lys Gln Glu Lys Leu Val His Met Ala Ser Gly
                245                 250                 255

Pro Pro Ser Ile Thr Asp Phe Gln Ile Leu Glu Lys
            260                 265
```

<210> SEQ ID NO 43
<211> LENGTH: 396
<212> TYPE: DNA
<213> ORGANISM: Canis familiaris

<400> SEQUENCE: 43

```
tgtccagaca gtcaaatcat cttctcgaac cccaagtgac aagccagtag ctcatgttgt     60
agcaaacccc gaagctgagg ggcagctcca gtggctgagc cgacgtgcca atgcccttct    120
ggccaacggc gtggagctga cagacaacca gctgatagtg ccgtcagatg ggttgtacct    180
catctactcc caggtcctct tcaagggcca agggtgccct tccacccatg tgctcctcac    240
```

```
ccacaccatc agccgcttcg ccgtctccta ccagacaaag gtcaacctac tctctgccat    300
caagagccct tgccaaaggg agaccccaga ggggaccgag gccaagccct ggtacgagcc    360
catctacctg ggagggtct tccaactgga gaaggg                               396
```

```
<210> SEQ ID NO 44
<211> LENGTH: 132
<212> TYPE: PRT
<213> ORGANISM: Canis familiaris

<400> SEQUENCE: 44
```

| Val | Gln | Thr | Val | Lys | Ser | Ser | Arg | Thr | Pro | Ser | Asp | Lys | Pro | Val |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Ala His Val Val Ala Asn Pro Glu Ala Glu Gly Gln Leu Gln Trp Leu
            20                  25                  30

Ser Arg Arg Ala Asn Ala Leu Leu Ala Asn Gly Val Glu Leu Thr Asp
        35                  40                  45

Asn Gln Leu Ile Val Pro Ser Asp Gly Leu Tyr Leu Ile Tyr Ser Gln
    50                  55                  60

Val Leu Phe Lys Gly Gln Gly Cys Pro Ser Thr His Val Leu Leu Thr
65                  70                  75                  80

His Thr Ile Ser Arg Phe Ala Val Ser Tyr Gln Thr Lys Val Asn Leu
                85                  90                  95

Leu Ser Ala Ile Lys Ser Pro Cys Gln Arg Glu Thr Pro Glu Gly Thr
            100                 105                 110

Glu Ala Lys Pro Trp Tyr Glu Pro Ile Tyr Leu Gly Gly Val Phe Gln
        115                 120                 125

Leu Glu Lys Gly
    130

```
<210> SEQ ID NO 45
<211> LENGTH: 816
<212> TYPE: DNA
<213> ORGANISM: Macaca mulatta
<220> FEATURE:
<221> NAME/KEY: CDS
<222> LOCATION: (1)...(813)

<400> SEQUENCE: 45
``` atg gcc aaa gtt cca gac atg ttt gaa gac ctg aag aac tgt tac agt     48
Met Ala Lys Val Pro Asp Met Phe Glu Asp Leu Lys Asn Cys Tyr Ser
1               5                   10                  15 gaa aat gaa gaa gac agt tcc tcc att gac cat ctg tct ctg aat cag     96
Glu Asn Glu Glu Asp Ser Ser Ser Ile Asp His Leu Ser Leu Asn Gln
            20                  25                  30 aaa tcc ttc tat gat gta agc tat ggc cca ctc cat gaa ggc tgc atg    144
Lys Ser Phe Tyr Asp Val Ser Tyr Gly Pro Leu His Glu Gly Cys Met
        35                  40                  45 gat cag tct gtg tcc ctg agt atc tct gaa atc tct aaa aca tcc aag    192
Asp Gln Ser Val Ser Leu Ser Ile Ser Glu Ile Ser Lys Thr Ser Lys
    50                  55                  60 ctg acc ttc aag cag agc atg gtg gta gta tca acc aat ggg aag gtt    240
Leu Thr Phe Lys Gln Ser Met Val Val Val Ser Thr Asn Gly Lys Val
65                  70                  75                  80 ctg aag aag aga cgg ttg agt tta agc cag tcc atc act gat aat aac    288
Leu Lys Lys Arg Arg Leu Ser Leu Ser Gln Ser Ile Thr Asp Asn Asn
                85                  90                  95 ctg gag gcc atc gcc aac gac tca gag gaa gaa atc atc aag ccc agg    336
Leu Glu Ala Ile Ala Asn Asp Ser Glu Glu Glu Ile Ile Lys Pro Arg
            100                 105                 110

```
tcg gca cct ttt agc ttc cta agc aat atg aca tac cac ttt ata agg    384
Ser Ala Pro Phe Ser Phe Leu Ser Asn Met Thr Tyr His Phe Ile Arg
        115                 120                 125 atc atc aaa cac gaa ttc atc ctg aat gac acc ctc aat caa act ata    432
Ile Ile Lys His Glu Phe Ile Leu Asn Asp Thr Leu Asn Gln Thr Ile
    130                 135                 140 att cga gcc aat gat cag cac ctc acg gct gct gca ata cat aat ctg    480
Ile Arg Ala Asn Asp Gln His Leu Thr Ala Ala Ala Ile His Asn Leu
145                 150                 155                 160 gat gaa gca gtg aaa ttt gac atg ggt gct tat acg tca tca aag gat    528
Asp Glu Ala Val Lys Phe Asp Met Gly Ala Tyr Thr Ser Ser Lys Asp
                165                 170                 175 gat act aaa gtt cct gtg att cta aga atc tca aaa act caa ttg tat    576
Asp Thr Lys Val Pro Val Ile Leu Arg Ile Ser Lys Thr Gln Leu Tyr
            180                 185                 190 gtg agt gcc caa gat gaa gac caa ccg gtg ctg ctg aag gag atg cct    624
Val Ser Ala Gln Asp Glu Asp Gln Pro Val Leu Leu Lys Glu Met Pro
        195                 200                 205 gag ata aac aaa acc atc aca ggt agt gag acc aac ttc ctc ttc ttc    672
Glu Ile Asn Lys Thr Ile Thr Gly Ser Glu Thr Asn Phe Leu Phe Phe
    210                 215                 220 tgg gaa act cat ggc act aag aac tac ttc ata tca gtt gcc cat cca    720
Trp Glu Thr His Gly Thr Lys Asn Tyr Phe Ile Ser Val Ala His Pro
225                 230                 235                 240 aac ttg ttt att gcc aca aag cat gac aat tgg gtg tgc ttg gca aag    768
Asn Leu Phe Ile Ala Thr Lys His Asp Asn Trp Val Cys Leu Ala Lys
                245                 250                 255 ggg cta ccc tct atc act gac ttt cag ata ctg gaa aac cag gcg        813
Gly Leu Pro Ser Ile Thr Asp Phe Gln Ile Leu Glu Asn Gln Ala
            260                 265                 270 tag                                                                816

<210> SEQ ID NO 46
<211> LENGTH: 271
<212> TYPE: PRT
<213> ORGANISM: Macaca mulatta

<400> SEQUENCE: 46

Met Ala Lys Val Pro Asp Met Phe Glu Asp Leu Lys Asn Cys Tyr Ser
1               5                   10                  15

Glu Asn Glu Glu Asp Ser Ser Ile Asp His Leu Ser Leu Asn Gln
            20                  25                  30

Lys Ser Phe Tyr Asp Val Ser Tyr Gly Pro Leu His Glu Gly Cys Met
        35                  40                  45

Asp Gln Ser Val Ser Leu Ser Ile Ser Glu Ile Ser Lys Thr Ser Lys
    50                  55                  60

Leu Thr Phe Lys Gln Ser Met Val Val Ser Thr Asn Gly Lys Val
65                  70                  75                  80

Leu Lys Lys Arg Arg Leu Ser Leu Ser Gln Ser Ile Thr Asp Asn Asn
                85                  90                  95

Leu Glu Ala Ile Ala Asn Asp Ser Glu Glu Ile Ile Lys Pro Arg
            100                 105                 110

Ser Ala Pro Phe Ser Phe Leu Ser Asn Met Thr Tyr His Phe Ile Arg
        115                 120                 125

Ile Ile Lys His Glu Phe Ile Leu Asn Asp Thr Leu Asn Gln Thr Ile
    130                 135                 140

Ile Arg Ala Asn Asp Gln His Leu Thr Ala Ala Ala Ile His Asn Leu
```

```
                145                 150                 155                 160
Asp Glu Ala Val Lys Phe Asp Met Gly Ala Tyr Thr Ser Ser Lys Asp
                    165                 170                 175

Asp Thr Lys Val Pro Val Ile Leu Arg Ile Ser Lys Thr Gln Leu Tyr
                180                 185                 190

Val Ser Ala Gln Asp Glu Asp Gln Pro Val Leu Leu Lys Glu Met Pro
            195                 200                 205

Glu Ile Asn Lys Thr Ile Thr Gly Ser Glu Thr Asn Phe Leu Phe Phe
        210                 215                 220

Trp Glu Thr His Gly Thr Lys Asn Tyr Phe Ile Ser Val Ala His Pro
225                 230                 235                 240

Asn Leu Phe Ile Ala Thr Lys His Asp Asn Trp Val Cys Leu Ala Lys
                245                 250                 255

Gly Leu Pro Ser Ile Thr Asp Phe Gln Ile Leu Glu Asn Gln Ala
                260                 265                 270

<210> SEQ ID NO 47
<211> LENGTH: 816
<212> TYPE: DNA
<213> ORGANISM: Cercocebus torquatus
<220> FEATURE:
<221> NAME/KEY: CDS
<222> LOCATION: (1)...(813)

<400> SEQUENCE: 47 atg gcc aaa gtt cca gac atg ttt gaa gac ctg aag aac tgt tac agt        48
Met Ala Lys Val Pro Asp Met Phe Glu Asp Leu Lys Asn Cys Tyr Ser
1               5                   10                  15 gaa aac gaa gaa gac agt tcc tcc att gac cat ctg ttt ctg aat cag        96
Glu Asn Glu Glu Asp Ser Ser Ser Ile Asp His Leu Phe Leu Asn Gln
            20                  25                  30 aaa tcc ttc tat gat gta agc tat ggc cca ctc cac gaa agc tgc atg       144
Lys Ser Phe Tyr Asp Val Ser Tyr Gly Pro Leu His Glu Ser Cys Met
        35                  40                  45 gat cag tct gtg tct ctg agt atc tct gaa atc tct aaa aca tcc aag       192
Asp Gln Ser Val Ser Leu Ser Ile Ser Glu Ile Ser Lys Thr Ser Lys
    50                  55                  60 ctg tcc ttc aag cag agc atg gtg gta gta tca acc aat ggg aag gtt       240
Leu Ser Phe Lys Gln Ser Met Val Val Val Ser Thr Asn Gly Lys Val
65                  70                  75                  80 ctg aag aag aga cgg ttg agt tta agc cag tcc atc gct gat gat aac       288
Leu Lys Lys Arg Arg Leu Ser Leu Ser Gln Ser Ile Ala Asp Asp Asn
                85                  90                  95 ctg gag gcc atc gcc aac gac tca gag gaa gaa atc atc aag ccc agg       336
Leu Glu Ala Ile Ala Asn Asp Ser Glu Glu Glu Ile Ile Lys Pro Arg
            100                 105                 110 tcg gca cct ttt agc ttc cta agc aat atg aca tac cac att ata agg       384
Ser Ala Pro Phe Ser Phe Leu Ser Asn Met Thr Tyr His Ile Ile Arg
        115                 120                 125 atc atc aaa cac gaa tcc atc ctg aat gac acc ctc aat caa act ata       432
Ile Ile Lys His Glu Ser Ile Leu Asn Asp Thr Leu Asn Gln Thr Ile
    130                 135                 140 att cga gcc aat gat cag tac ctc aca gct gct gca ata cat aat ctg       480
Ile Arg Ala Asn Asp Gln Tyr Leu Thr Ala Ala Ala Ile His Asn Leu
145                 150                 155                 160 gat gaa gca gtg aaa ttt gac atg ggt gct tat acg tca tca aag gat       528
Asp Glu Ala Val Lys Phe Asp Met Gly Ala Tyr Thr Ser Ser Lys Asp
                165                 170                 175 gat act aaa gtt cct gtg att cta aga atc tca aaa act caa ttg tat       576
```

```
Asp Thr Lys Val Pro Val Ile Leu Arg Ile Ser Lys Thr Gln Leu Tyr
            180                 185                 190 gtg agt gcc caa gat gaa gac caa ccg gtg ctg ctg aag gag atg cct      624
Val Ser Ala Gln Asp Glu Asp Gln Pro Val Leu Leu Lys Glu Met Pro
            195                 200                 205 gag ata ccc aaa acc acc aca ggt ggt gag acc aac tcc ctc tcc tcc      672
Glu Ile Pro Lys Thr Thr Thr Gly Gly Glu Thr Asn Ser Leu Ser Ser
    210                 215                 220 tgg gaa act cgc ggc act aag aac tac ttc ata tca gtt gcc cat cca      720
Trp Glu Thr Arg Gly Thr Lys Asn Tyr Phe Ile Ser Val Ala His Pro
225                 230                 235                 240 aac ttg ttt att gcc aca aag cac gac aat tgg gtg tgc ctg gca aag      768
Asn Leu Phe Ile Ala Thr Lys His Asp Asn Trp Val Cys Leu Ala Lys
                245                 250                 255 ggg cta ccc tct atc act gac ttt cag ata ctg gaa aac cag gcg          813
Gly Leu Pro Ser Ile Thr Asp Phe Gln Ile Leu Glu Asn Gln Ala
            260                 265                 270 tag                                                                    816
```

<210> SEQ ID NO 48
<211> LENGTH: 271
<212> TYPE: PRT
<213> ORGANISM: Cercocebus torquatus

<400> SEQUENCE: 48

```
Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Phe Leu Asn Gln
            20                  25                  30

Lys Ser Phe Tyr Asp Val Ser Tyr Gly Pro Leu His Glu Ser Cys Met
        35                  40                  45

Asp Gln Ser Val Ser Leu Ser Ile Ser Glu Ile Ser Lys Thr Ser Lys
    50                  55                  60

Leu Ser Phe Lys Gln Ser Met Val Val Ser Thr Asn Gly Lys Val
65              70                  75                  80

Leu Lys Lys Arg Arg Leu Ser Leu Ser Gln Ser Ile Ala Asp Asp Asn
            85                  90                  95

Leu Glu Ala Ile Ala Asn Asp Ser Glu Glu Ile Ile Lys Pro Arg
            100                 105                 110

Ser Ala Pro Phe Ser Phe Leu Ser Asn Met Thr Tyr His Ile Ile Arg
        115                 120                 125

Ile Ile Lys His Glu Ser Ile Leu Asn Asp Thr Leu Asn Gln Thr Ile
    130                 135                 140

Ile Arg Ala Asn Asp Gln Tyr Leu Thr Ala Ala Ile His Asn Leu
145                 150                 155                 160

Asp Glu Ala Val Lys Phe Asp Met Gly Ala Tyr Thr Ser Ser Lys Asp
                165                 170                 175

Asp Thr Lys Val Pro Val Ile Leu Arg Ile Ser Lys Thr Gln Leu Tyr
            180                 185                 190

Val Ser Ala Gln Asp Glu Asp Gln Pro Val Leu Leu Lys Glu Met Pro
            195                 200                 205

Glu Ile Pro Lys Thr Thr Thr Gly Gly Glu Thr Asn Ser Leu Ser Ser
    210                 215                 220

Trp Glu Thr Arg Gly Thr Lys Asn Tyr Phe Ile Ser Val Ala His Pro
225                 230                 235                 240

Asn Leu Phe Ile Ala Thr Lys His Asp Asn Trp Val Cys Leu Ala Lys
```

```
                245                 250                 255
Gly Leu Pro Ser Ile Thr Asp Phe Gln Ile Leu Glu Asn Gln Ala
            260                 265                 270

<210> SEQ ID NO 49
<211> LENGTH: 354
<212> TYPE: DNA
<213> ORGANISM: Homo sapiens
<220> FEATURE:
<221> NAME/KEY: source
<222> LOCATION: (1)...(354)
<223> OTHER INFORMATION: IL-1alpha cDNA corresponding to nucleotides
      1-354 and encoding amino acids 1-118

<400> SEQUENCE: 49
atggccaaag ttccagacat gtttgaagac ctgaagaact gttacagtga aaatgaagaa      60
gacagttcct ccattgatca tctgtctctg aatcagaaat ccttctatca tgtaagctat     120
ggcccactcc atgaaggctg catggatcaa tctgtgtctc tgagtatctc tgaaacctct     180
aaaacatcca agcttacctt caaggagagc atggtggtag tagcaaccaa cgggaaggtt     240
ctgaagaaga gacggttgag tttaagccaa tccatcactg atgatgacct ggaggccatc     300
gccaatgact cagaggaaga aatcatcaag cctaggtcag cacctttag cttc            354

<210> SEQ ID NO 50
<211> LENGTH: 696
<212> TYPE: DNA
<213> ORGANISM: Homo sapiens
<220> FEATURE:
<221> NAME/KEY: source
<222> LOCATION: (1)...(696)
<223> OTHER INFORMATION: IgG1 Fc region (GenBank Accession No. Z17370)

<400> SEQUENCE: 50
gagcccaaat cttgtgacaa aactcacaca tgcccaccgt gcccagcacc tgaactcctg      60
gggggaccgt cagtcttcct cttccccca aaacccaagg acaccctcat gatctcccgg     120
acccctgagg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgggt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaaagggca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga acaactacaa gaccacgcct     540
cccgtgctgg actccgacgg ctccttcttc ctctacagca agctcaccgt ggacaagagc     600
aggtggcagc aggggaacgt cttctcatgc tccgtgatgc atgaggctct gcacaaccac     660
tacacgcaga agagcctctc cctgtctccg ggtaaa                               696

<210> SEQ ID NO 51
<211> LENGTH: 1050
<212> TYPE: DNA
<213> ORGANISM: Artificial Sequence
<220> FEATURE:
<223> OTHER INFORMATION: IL-1alpha(1-118)-Fc fusion protein
<221> NAME/KEY: CDS
<222> LOCATION: (1)...(1050)

<400> SEQUENCE: 51 atg gcc aaa gtt cca gac atg ttt gaa gac ctg aag aac tgt tac agt       48
```

```
    Met Ala Lys Val Pro Asp Met Phe Glu Asp Leu Lys Asn Cys Tyr Ser
    1               5                   10                  15 gaa aat gaa gaa gac agt tcc tcc att gat cat ctg tct ctg aat cag      96
Glu Asn Glu Glu Asp Ser Ser Ser Ile Asp His Leu Ser Leu Asn Gln
            20                  25                  30 aaa tcc ttc tat cat gta agc tat ggc cca ctc cat gaa ggc tgc atg     144
Lys Ser Phe Tyr His Val Ser Tyr Gly Pro Leu His Glu Gly Cys Met
        35                  40                  45 gat caa tct gtg tct ctg agt atc tct gaa acc tct aaa aca tcc aag     192
Asp Gln Ser Val Ser Leu Ser Ile Ser Glu Thr Ser Lys Thr Ser Lys
    50                  55                  60 ctt acc ttc aag gag agc atg gtg gta gta gca acc aac ggg aag gtt     240
Leu Thr Phe Lys Glu Ser Met Val Val Val Ala Thr Asn Gly Lys Val
65                  70                  75                  80 ctg aag aag aga cgg ttg agt tta agc caa tcc atc act gat gat gac     288
Leu Lys Lys Arg Arg Leu Ser Leu Ser Gln Ser Ile Thr Asp Asp Asp
                85                  90                  95 ctg gag gcc atc gcc aat gac tca gag gaa gaa atc atc aag cct agg     336
Leu Glu Ala Ile Ala Asn Asp Ser Glu Glu Glu Ile Ile Lys Pro Arg
            100                 105                 110 tca gca cct ttt agc ttc gag ccc aaa tct tgt gac aaa act cac aca     384
Ser Ala Pro Phe Ser Phe Glu Pro Lys Ser Cys Asp Lys Thr His Thr
        115                 120                 125 tgc cca ccg tgc cca gca cct gaa ctc ctg ggg gga ccg tca gtc ttc     432
Cys Pro Pro Cys Pro Ala Pro Glu Leu Leu Gly Gly Pro Ser Val Phe
    130                 135                 140 ctc ttc ccc cca aaa ccc aag gac acc ctc atg atc tcc cgg acc cct     480
Leu Phe Pro Pro Lys Pro Lys Asp Thr Leu Met Ile Ser Arg Thr Pro
145                 150                 155                 160 gag gtc aca tgc gtg gtg gtg gac gtg agc cac gaa gac cct gag gtc     528
Glu Val Thr Cys Val Val Val Asp Val Ser His Glu Asp Pro Glu Val
                165                 170                 175 aag ttc aac tgg tac gtg gac ggc gtg gag gtg cat aat gcc aag aca     576
Lys Phe Asn Trp Tyr Val Asp Gly Val Glu Val His Asn Ala Lys Thr
            180                 185                 190 aag ccg cgg gag gag cag tac aac agc acg tac cgg gtg gtc agc gtc     624
Lys Pro Arg Glu Glu Gln Tyr Asn Ser Thr Tyr Arg Val Val Ser Val
        195                 200                 205 ctc acc gtc ctg cac cag gac tgg ctg aat ggc aag gag tac aag tgc     672
Leu Thr Val Leu His Gln Asp Trp Leu Asn Gly Lys Glu Tyr Lys Cys
    210                 215                 220 aag gtc tcc aac aaa gcc ctc cca gcc ccc atc gag aaa acc atc tcc     720
Lys Val Ser Asn Lys Ala Leu Pro Ala Pro Ile Glu Lys Thr Ile Ser
225                 230                 235                 240 aaa gcc aaa ggg cag ccc cga gaa cca cag gtg tac acc ctg ccc cca     768
Lys Ala Lys Gly Gln Pro Arg Glu Pro Gln Val Tyr Thr Leu Pro Pro
                245                 250                 255 tcc cgg gat gag ctg acc aag aac cag gtc agc ctg acc tgc ctg gtc     816
Ser Arg Asp Glu Leu Thr Lys Asn Gln Val Ser Leu Thr Cys Leu Val
            260                 265                 270 aaa ggc ttc tat ccc agc gac atc gcc gtg gag tgg gag agc aat ggg     864
Lys Gly Phe Tyr Pro Ser Asp Ile Ala Val Glu Trp Glu Ser Asn Gly
        275                 280                 285 cag ccg gag aac aac tac aag acc acg cct ccc gtg ctg gac tcc gac     912
Gln Pro Glu Asn Asn Tyr Lys Thr Thr Pro Pro Val Leu Asp Ser Asp
    290                 295                 300 ggc tcc ttc ttc ctc tac agc aag ctc acc gtg gac aag agc agg tgg     960
Gly Ser Phe Phe Leu Tyr Ser Lys Leu Thr Val Asp Lys Ser Arg Trp
305                 310                 315                 320
```

-continued

| | | |
|---|---|---|
| cag cag ggg aac gtc ttc tca tgc tcc gtg atg cat gag gct ctg cac<br>Gln Gln Gly Asn Val Phe Ser Cys Ser Val Met His Glu Ala Leu His<br>325                    330                    335 | 1008 |
| aac cac tac acg cag aag agc ctc tcc ctg tct ccg ggt aaa<br>Asn His Tyr Thr Gln Lys Ser Leu Ser Leu Ser Pro Gly Lys<br>340                    345                350 | 1050 |

<210> SEQ ID NO 52
<211> LENGTH: 350
<212> TYPE: PRT
<213> ORGANISM: Artificial Sequence
<220> FEATURE:
<223> OTHER INFORMATION: IL-1alpha(1-118)-Fc fusion protein

<400> SEQUENCE: 52

Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
            20                  25                  30

Lys Ser Phe Tyr His Val Ser Tyr Gly Pro Leu His Glu Gly Cys Met
        35                  40                  45

Asp Gln Ser Val Ser Leu Ser Ile Ser Glu Thr Ser Lys Thr Ser Lys
    50                  55                  60

Leu Thr Phe Lys Glu Ser Met Val Val Ala Thr Asn Gly Lys Val
65                  70                  75                  80

Leu Lys Lys Arg Arg Leu Ser Leu Ser Gln Ser Ile Thr Asp Asp Asp
                85                  90                  95

Leu Glu Ala Ile Ala Asn Asp Ser Glu Glu Ile Ile Lys Pro Arg
            100                 105                 110

Ser Ala Pro Phe Ser Phe Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His

```
                    325                 330                 335
Asn His Tyr Thr Gln Lys Ser Leu Ser Leu Ser Pro Gly Lys
            340                 345                 350

<210> SEQ ID NO 53
<211> LENGTH: 1794
<212> TYPE: DNA
<213> ORGANISM: Artificial Sequence
<220> FEATURE:
<223> OTHER INFORMATION: IL-1alpha(1-118)-Fc-EGFP fusion protein
<221> NAME/KEY: CDS
<222> LOCATION: (1)...(1791)

<400> SEQUENCE: 53 atg gcc aaa gtt cca gac atg ttt gaa gac ctg aag aac tgt tac agt        48
Met Ala Lys Val Pro Asp Met Phe Glu Asp Leu Lys Asn Cys Tyr Ser
 1               5                  10                  15 gaa aat gaa gaa gac agt tcc tcc att gat cat ctg tct ctg aat cag        96
Glu Asn Glu Glu Asp Ser Ser Ser Ile Asp His Leu Ser Leu Asn Gln
             20                  25                  30 aaa tcc ttc tat cat gta agc tat ggc cca ctc cat gaa ggc tgc atg       144
Lys Ser Phe Tyr His Val Ser Tyr Gly Pro Leu His Glu Gly Cys Met
         35                  40                  45 gat caa tct gtg tct ctg agt atc tct gaa acc tct aaa aca tcc aag       192
Asp Gln Ser Val Ser Leu Ser Ile Ser Glu Thr Ser Lys Thr Ser Lys
     50                  55                  60 ctt acc ttc aag gag agc atg gtg gta gta gca acc aac ggg aag gtt       240
Leu Thr Phe Lys Glu Ser Met Val Val Val Ala Thr Asn Gly Lys Val
 65                  70                  75                  80 ctg aag aag aga cgg ttg agt tta agc caa tcc atc act gat gat gac       288
Leu Lys Lys Arg Arg Leu Ser Leu Ser Gln Ser Ile Thr Asp Asp Asp
                 85                  90                  95 ctg gag gcc atc gcc aat gac tca gag gaa gaa atc atc aag cct agg       336
Leu Glu Ala Ile Ala Asn Asp Ser Glu Glu Glu Ile Ile Lys Pro Arg
            100                 105                 110 tca gca cct ttt agc ttc gag ccc aaa tct tgt gac aaa act cac aca       384
Ser Ala Pro Phe Ser Phe Glu Pro Lys Ser Cys Asp Lys Thr His Thr
        115                 120                 125 tgc cca ccg tgc cca gca cct gaa ctc ctg ggg gga ccg tca gtc ttc       432
Cys Pro Pro Cys Pro Ala Pro Glu Leu Leu Gly Gly Pro Ser Val Phe
    130                 135                 140 ctc ttc ccc cca aaa ccc aag gac acc ctc atg atc tcc cgg acc cct       480
Leu Phe Pro Pro Lys Pro Lys Asp Thr Leu Met Ile Ser Arg Thr Pro
145                 150                 155                 160 gag gtc aca tgc gtg gtg gtg gac gtg agc cac gaa gac cct gag gtc       528
Glu Val Thr Cys Val Val Val Asp Val Ser His Glu Asp Pro Glu Val
                165                 170                 175 aag ttc aac tgg tac gtg gac ggc gtg gag gtg cat aat gcc aag aca       576
Lys Phe Asn Trp Tyr Val Asp Gly Val Glu Val His Asn Ala Lys Thr
            180                 185                 190 aag ccg cgg gag gag cag tac aac agc acg tac cgg gtg gtc agc gtc       624
Lys Pro Arg Glu Glu Gln Tyr Asn Ser Thr Tyr Arg Val Val Ser Val
        195                 200                 205 ctc acc gtc ctg cac cag gac tgg ctg aat ggc aag gag tac aag tgc       672
Leu Thr Val Leu His Gln Asp Trp Leu Asn Gly Lys Glu Tyr Lys Cys
    210                 215                 220 aag gtc tcc aac aaa gcc ctc cca gcc ccc atc gag aaa acc atc tcc       720
Lys Val Ser Asn Lys Ala Leu Pro Ala Pro Ile Glu Lys Thr Ile Ser
225                 230                 235                 240 aaa gcc aaa ggg cag ccc cga gaa cca cag gtg tac acc ctg ccc cca       768
Lys Ala Lys Gly Gln Pro Arg Glu Pro Gln Val Tyr Thr Leu Pro Pro
```

-continued

|  |  |  |  |  |  |  |  |  |  |  |  |  |  |  |  |
|---|---|---|---|---|---|---|---|---|---|---|---|---|---|---|---|
|  |  | 245 |  |  |  |  | 250 |  |  |  |  | 255 |  |  |  |
| tcc | cgg | gat | gag | ctg | acc | aag | aac | cag | gtc | agc | ctg | acc | tgc | ctg | gtc | 816 |
| Ser | Arg | Asp | Glu | Leu | Thr | Lys | Asn | Gln | Val | Ser | Leu | Thr | Cys | Leu | Val |  |
|  |  |  | 260 |  |  |  |  | 265 |  |  |  |  | 270 |  |  |  |
| aaa | ggc | ttc | tat | ccc | agc | gac | atc | gcc | gtg | gag | tgg | gag | agc | aat | ggg | 864 |
| Lys | Gly | Phe | Tyr | Pro | Ser | Asp | Ile | Ala | Val | Glu | Trp | Glu | Ser | Asn | Gly |  |
|  |  | 275 |  |  |  |  | 280 |  |  |  |  | 285 |  |  |  |  |
| cag | ccg | gag | aac | aac | tac | aag | acc | acg | cct | ccc | gtg | ctg | gac | tcc | gac | 912 |
| Gln | Pro | Glu | Asn | Asn | Tyr | Lys | Thr | Thr | Pro | Pro | Val | Leu | Asp | Ser | Asp |  |
| 290 |  |  |  |  | 295 |  |  |  |  | 300 |  |  |  |  |  |  |
| ggc | tcc | ttc | ttc | ctc | tac | agc | aag | ctc | acc | gtg | gac | aag | agc | agg | tgg | 960 |
| Gly | Ser | Phe | Phe | Leu | Tyr | Ser | Lys | Leu | Thr | Val | Asp | Lys | Ser | Arg | Trp |  |
| 305 |  |  |  |  | 310 |  |  |  |  | 315 |  |  |  |  | 320 |  |
| cag | cag | ggg | aac | gtc | ttc | tca | tgc | tcc | gtg | atg | cat | gag | gct | ctg | cac | 1008 |
| Gln | Gln | Gly | Asn | Val | Phe | Ser | Cys | Ser | Val | Met | His | Glu | Ala | Leu | His |  |
|  |  |  |  | 325 |  |  |  |  | 330 |  |  |  |  | 335 |  |  |
| aac | cac | tac | acg | cag | aag | agc | ctc | tcc | ctg | tct | ccg | ggt | aaa | acg | acg | 1056 |
| Asn | His | Tyr | Thr | Gln | Lys | Ser | Leu | Ser | Leu | Ser | Pro | Gly | Lys | Thr | Thr |  |
|  |  |  | 340 |  |  |  |  | 345 |  |  |  |  | 350 |  |  |  |
| gat | cca | ccg | gtc | gcc | acc | atg | gtg | agc | aag | ggc | gag | gag | ctg | ttc | acc | 1104 |
| Asp | Pro | Pro | Val | Ala | Thr | Met | Val | Ser | Lys | Gly | Glu | Glu | Leu | Phe | Thr |  |
|  |  | 355 |  |  |  |  | 360 |  |  |  |  | 365 |  |  |  |  |
| ggg | gtg | gtg | ccc | atc | ctg | gtc | gag | ctg | gac | ggc | gac | gta | aac | ggc | cac | 1152 |
| Gly | Val | Val | Pro | Ile | Leu | Val | Glu | Leu | Asp | Gly | Asp | Val | Asn | Gly | His |  |
| 370 |  |  |  |  | 375 |  |  |  |  | 380 |  |  |  |  |  |  |
| aag | ttc | agc | gtg | tcc | ggc | gag | ggc | gag | ggc | gat | gcc | acc | tac | ggc | aag | 1200 |
| Lys | Phe | Ser | Val | Ser | Gly | Glu | Gly | Glu | Gly | Asp | Ala | Thr | Tyr | Gly | Lys |  |
| 385 |  |  |  |  | 390 |  |  |  |  | 395 |  |  |  |  | 400 |  |
| ctg | acc | ctg | aag | ttc | atc | tgc | acc | acc | ggc | aag | ctg | ccc | gtg | ccc | tgg | 1248 |
| Leu | Thr | Leu | Lys | Phe | Ile | Cys | Thr | Thr | Gly | Lys | Leu | Pro | Val | Pro | Trp |  |
|  |  |  |  | 405 |  |  |  |  | 410 |  |  |  |  | 415 |  |  |
| ccc | acc | ctc | gtg | acc | acc | ctg | acc | tac | ggc | gtg | cag | tgc | ttc | agc | cgc | 1296 |
| Pro | Thr | Leu | Val | Thr | Thr | Leu | Thr | Tyr | Gly | Val | Gln | Cys | Phe | Ser | Arg |  |
|  |  |  | 420 |  |  |  |  | 425 |  |  |  |  | 430 |  |  |  |
| tac | ccc | gac | cac | atg | aag | cag | cac | gac | ttc | ttc | aag | tcc | gcc | atg | ccc | 1344 |
| Tyr | Pro | Asp | His | Met | Lys | Gln | His | Asp | Phe | Phe | Lys | Ser | Ala | Met | Pro |  |
|  |  | 435 |  |  |  |  | 440 |  |  |  |  | 445 |  |  |  |  |
| gaa | ggc | tac | gtc | cag | gag | cgc | acc | atc | ttc | ttc | aag | gac | gac | ggc | aac | 1392 |
| Glu | Gly | Tyr | Val | Gln | Glu | Arg | Thr | Ile | Phe | Phe | Lys | Asp | Asp | Gly | Asn |  |
| 450 |  |  |  |  | 455 |  |  |  |  | 460 |  |  |  |  |  |  |
| tac | aag | acc | cgc | gcc | gag | gtg | aag | ttc | gag | ggc | gac | acc | ctg | gtg | aac | 1440 |
| Tyr | Lys | Thr | Arg | Ala | Glu | Val | Lys | Phe | Glu | Gly | Asp | Thr | Leu | Val | Asn |  |
| 465 |  |  |  |  | 470 |  |  |  |  | 475 |  |  |  |  | 480 |  |
| cgc | atc | gag | ctg | aag | ggc | atc | gac | ttc | aag | gag | gac | ggc | aac | atc | ctg | 1488 |
| Arg | Ile | Glu | Leu | Lys | Gly | Ile | Asp | Phe | Lys | Glu | Asp | Gly | Asn | Ile | Leu |  |
|  |  |  |  | 485 |  |  |  |  | 490 |  |  |  |  | 495 |  |  |
| ggg | cac | aag | ctg | gag | tac | aac | tac | aac | agc | cac | aac | gtc | tat | atc | atg | 1536 |
| Gly | His | Lys | Leu | Glu | Tyr | Asn | Tyr | Asn | Ser | His | Asn | Val | Tyr | Ile | Met |  |
|  |  |  | 500 |  |  |  |  | 505 |  |  |  |  | 510 |  |  |  |
| gcc | gac | aag | cag | aag | aac | ggc | atc | aag | gtg | aac | ttc | aag | atc | cgc | cac | 1584 |
| Ala | Asp | Lys | Gln | Lys | Asn | Gly | Ile | Lys | Val | Asn | Phe | Lys | Ile | Arg | His |  |
|  |  | 515 |  |  |  |  | 520 |  |  |  |  | 525 |  |  |  |  |
| aac | atc | gag | gac | ggc | agc | gtg | cag | ctc | gcc | gac | cac | tac | cag | cag | aac | 1632 |
| Asn | Ile | Glu | Asp | Gly | Ser | Val | Gln | Leu | Ala | Asp | His | Tyr | Gln | Gln | Asn |  |
| 530 |  |  |  |  | 535 |  |  |  |  | 540 |  |  |  |  |  |  |
| acc | ccc | atc | ggc | gac | ggc | ccc | gtg | ctg | ctg | ccc | gac | aac | cac | tac | ctg | 1680 |
| Thr | Pro | Ile | Gly | Asp | Gly | Pro | Val | Leu | Leu | Pro | Asp | Asn | His | Tyr | Leu |  |
| 545 |  |  |  |  | 550 |  |  |  |  | 555 |  |  |  |  | 560 |  |
| agc | acc | cag | tcc | gcc | ctg | agc | aaa | gac | ccc | aac | gag | aag | cgc | gat | cac | 1728 |

```
Ser Thr Gln Ser Ala Leu Ser Lys Asp Pro Asn Glu Lys Arg Asp His
            565                 570                 575 atg gtc ctg ctg gag ttc gtg acc gcc gcc ggg atc act ctc ggc atg      1776
Met Val Leu Leu Glu Phe Val Thr Ala Ala Gly Ile Thr Leu Gly Met
            580                 585                 590 gac gag ctg tac aag taa                                              1794
Asp Glu Leu Tyr Lys
            595

<210> SEQ ID NO 54
<211> LENGTH: 597
<212> TYPE: PRT
<213> ORGANISM: Artificial Sequence
<220> FEATURE:
<223> OTHER INFORMATION: IL-1alpha(1-118)-Fc-EGFP fusion protein

<400> SEQUENCE: 54

Met Ala Lys Val Pro Asp Met Phe Glu Asp Leu Lys Asn Cys Tyr Ser
 1               5                  10                  15

Glu Asn Glu Glu Asp Ser Ser Ser Ile Asp His Leu Ser Leu Asn Gln
            20                  25                  30

Lys Ser Phe Tyr His Val Ser Tyr Gly Pro Leu His Glu Gly Cys Met
        35                  40                  45

Asp Gln Ser Val Ser Leu Ser Ile Ser Glu Thr Ser Lys Thr Ser Lys
    50                  55                  60

Leu Thr Phe Lys Glu Ser Met Val Val Ala Thr Asn Gly Lys Val
65                  70                  75                  80

Leu Lys Lys Arg Arg Leu Ser Leu Ser Gln Ser Ile Thr Asp Asp Asp
                85                  90                  95

Leu Glu Ala Ile Ala Asn Asp Ser Glu Glu Ile Ile Lys Pro Arg
            100                 105                 110

Ser Ala Pro Phe Ser Phe Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
```

-continued

```
                305                 310                 315                 320
Gln Gln Gly Asn Val Phe Ser Cys Ser Val Met His Glu Ala Leu His
                325                 330                 335
Asn His Tyr Thr Gln Lys Ser Leu Ser Leu Ser Pro Gly Lys Thr Thr
                340                 345                 350
Asp Pro Pro Val Ala Thr Met Val Ser Lys Gly Glu Leu Phe Thr
                355                 360             365
Gly Val Val Pro Ile Leu Val Glu Leu Asp Gly Asp Val Asn Gly His
        370                 375                 380
Lys Phe Ser Val Ser Gly Glu Gly Glu Gly Asp Ala Thr Tyr Gly Lys
385                 390                 395                 400
Leu Thr Leu Lys Phe Ile Cys Thr Thr Gly Lys Leu Pro Val Pro Trp
                405                 410                 415
Pro Thr Leu Val Thr Thr Leu Thr Tyr Gly Val Gln Cys Phe Ser Arg
                420                 425                 430
Tyr Pro Asp His Met Lys Gln His Asp Phe Phe Lys Ser Ala Met Pro
                435                 440                 445
Glu Gly Tyr Val Gln Glu Arg Thr Ile Phe Phe Lys Asp Asp Gly Asn
                450                 455                 460
Tyr Lys Thr Arg Ala Glu Val Lys Phe Glu Gly Asp Thr Leu Val Asn
465                 470                 475                 480
Arg Ile Glu Leu Lys Gly Ile Asp Phe Lys Glu Asp Gly Asn Ile Leu
                485                 490                 495
Gly His Lys Leu Glu Tyr Asn Tyr Asn Ser His Asn Val Tyr Ile Met
                500                 505                 510
Ala Asp Lys Gln Lys Asn Gly Ile Lys Val Asn Phe Lys Ile Arg His
                515                 520                 525
Asn Ile Glu Asp Gly Ser Val Gln Leu Ala Asp His Tyr Gln Gln Asn
                530                 535                 540
Thr Pro Ile Gly Asp Gly Pro Val Leu Leu Pro Asp Asn His Tyr Leu
545                 550                 555                 560
Ser Thr Gln Ser Ala Leu Ser Lys Asp Pro Asn Glu Lys Arg Asp His
                565                 570                 575
Met Val Leu Leu Glu Phe Val Thr Ala Ala Gly Ile Thr Leu Gly Met
                580                 585                 590
Asp Glu Leu Tyr Lys
                595

<210> SEQ ID NO 55
<211> LENGTH: 177
<212> TYPE: DNA
<213> ORGANISM: Drosophila melanogaster
<220> FEATURE:
<221> NAME/KEY: CDS
<222> LOCATION: (1)...(177)

<400> SEQUENCE: 55 tgc cgg cac agc tca ctc tct ctc tcc ctc tct ctc tct ctc tcc gtc      48
Cys Arg His Ser Ser Leu Ser Leu Ser Leu Ser Leu Ser Leu Ser Val
  1               5                  10                  15 tcc ctc tgt ttt cgt cta tct ctt gtg tac gtg ctg aat ggt cag gtt      96
Ser Leu Cys Phe Arg Leu Ser Leu Val Tyr Val Leu Asn Gly Gln Val
                 20                  25                  30 cac aaa aaa aga gtt tac gca att tca caa ttt gcc gca aac aac aat     144
His Lys Lys Arg Val Tyr Ala Ile Ser Gln Phe Ala Ala Asn Asn Asn
             35                  40                  45
```

```
aag gct gga atc gga atc tcc ctg agc gag gaa                          177
Lys Ala Gly Ile Gly Ile Ser Leu Ser Glu Glu
    50                  55
```

<210> SEQ ID NO 56
<211> LENGTH: 59
<212> TYPE: PRT
<213> ORGANISM: Drosophila melanogaster

<400> SEQUENCE: 56

```
Cys Arg His Ser Ser Leu Ser Leu Ser Leu Ser Leu Ser Val
 1               5                  10                  15

Ser Leu Cys Phe Arg Leu Ser Leu Val Tyr Val Leu Asn Gly Gln Val
            20                  25                  30

His Lys Lys Arg Val Tyr Ala Ile Ser Gln Phe Ala Ala Asn Asn Asn
        35                  40                  45

Lys Ala Gly Ile Gly Ile Ser Leu Ser Glu Glu
    50                  55
```

<210> SEQ ID NO 57
<211> LENGTH: 185
<212> TYPE: DNA
<213> ORGANISM: Artificial Sequence
<220> FEATURE:
<223> OTHER INFORMATION: Drosophila melanogaster polypeptide coding
      sequence with Kozak sequence

<400> SEQUENCE: 57

```
ccaccatgtg ccggcacagc tcactctctc tctccctctc tctctctctc tccgtctccc     60
tctgttttcg tctatctctt gtgtacgtgc tgaatggtca ggttcacaaa aaaagagttt   120
acgcaatttc acaatttgcc gcaaacaaca ataaggctgg aatcggaatc tccctgagcg   180
aggaa                                                                185
```

<210> SEQ ID NO 58
<211> LENGTH: 921
<212> TYPE: DNA
<213> ORGANISM: Artificial Sequence
<220> FEATURE:
<223> OTHER INFORMATION: Drosophila melanogaster polypeptide-EGFP fusion
      protein
<221> NAME/KEY: CDS
<222> LOCATION: (1)...(918)

<400> SEQUENCE: 58

```
atg tgc cgg cac agc tca ctc tct ctc tcc ctc tct ctc tct ctc tcc      48
Met Cys Arg His Ser Ser Leu Ser Leu Ser Leu Ser Leu Ser Leu Ser
 1               5                  10                  15 gtc tcc ctc tgt ttt cgt cta tct ctt gtg tac gtg ctg aat ggt cag      96
Val Ser Leu Cys Phe Arg Leu Ser Leu Val Tyr Val Leu Asn Gly Gln
            20                  25                  30 gtt cac aaa aaa aga gtt tac gca att tca caa ttt gcc gca aac aac     144
Val His Lys Lys Arg Val Tyr Ala Ile Ser Gln Phe Ala Ala Asn Asn
        35                  40                  45 aat aag gct gga atc gga atc tcc ctg agc gag gaa cgg gat cca ccg     192
Asn Lys Ala Gly Ile Gly Ile Ser Leu Ser Glu Glu Arg Asp Pro Pro
    50                  55                  60 gtc gcc acc atg gtg agc aag ggc gag gag ctg ttc acc ggg gtg gtg     240
Val Ala Thr Met Val Ser Lys Gly Glu Glu Leu Phe Thr Gly Val Val
 65                  70                  75                  80 ccc atc ctg gtc gag ctg gac ggc gac gta aac ggc cac aag ttc agc     288
Pro Ile Leu Val Glu Leu Asp Gly Asp Val Asn Gly His Lys Phe Ser
                 85                  90                  95
```

```
gtg tcc ggc gag ggc gag ggc gat gcc acc tac ggc aag ctg acc ctg      336
Val Ser Gly Glu Gly Glu Gly Asp Ala Thr Tyr Gly Lys Leu Thr Leu
            100                 105                 110 aag ttc atc tgc acc acc ggc aag ctg ccc gtg ccc tgg ccc acc ctc      384
Lys Phe Ile Cys Thr Thr Gly Lys Leu Pro Val Pro Trp Pro Thr Leu
        115                 120                 125 gtg acc acc ctg acc tac ggc gtg cag tgc ttc agc cgc tac ccc gac      432
Val Thr Thr Leu Thr Tyr Gly Val Gln Cys Phe Ser Arg Tyr Pro Asp
130                 135                 140 cac atg aag cag cac gac ttc ttc aag tcc gcc atg ccc gaa ggc tac      480
His Met Lys Gln His Asp Phe Phe Lys Ser Ala Met Pro Glu Gly Tyr
145                 150                 155                 160 gtc cag gag cgc acc atc ttc ttc aag gac gac ggc aac tac aag acc      528
Val Gln Glu Arg Thr Ile Phe Phe Lys Asp Asp Gly Asn Tyr Lys Thr
                165                 170                 175 cgc gcc gag gtg aag ttc gag ggc gac acc ctg gtg aac cgc atc gag      576
Arg Ala Glu Val Lys Phe Glu Gly Asp Thr Leu Val Asn Arg Ile Glu
            180                 185                 190 ctg aag ggc atc gac ttc aag gag gac ggc aac atc ctg ggg cac aag      624
Leu Lys Gly Ile Asp Phe Lys Glu Asp Gly Asn Ile Leu Gly His Lys
        195                 200                 205 ctg gag tac aac tac aac agc cac aac gtc tat atc atg gcc gac aag      672
Leu Glu Tyr Asn Tyr Asn Ser His Asn Val Tyr Ile Met Ala Asp Lys
210                 215                 220 cag aag aac ggc atc aag gtg aac ttc aag atc cgc cac aac atc gag      720
Gln Lys Asn Gly Ile Lys Val Asn Phe Lys Ile Arg His Asn Ile Glu
225                 230                 235                 240 gac ggc agc gtg cag ctc gcc gac cac tac cag cag aac acc ccc atc      768
Asp Gly Ser Val Gln Leu Ala Asp His Tyr Gln Gln Asn Thr Pro Ile
                245                 250                 255 ggc gac ggc ccc gtg ctg ctg ccc gac aac cac tac ctg agc acc cag      816
Gly Asp Gly Pro Val Leu Leu Pro Asp Asn His Tyr Leu Ser Thr Gln
            260                 265                 270 tcc gcc ctg agc aaa gac ccc aac gag aag cgc gat cac atg gtc ctg      864
Ser Ala Leu Ser Lys Asp Pro Asn Glu Lys Arg Asp His Met Val Leu
        275                 280                 285 ctg gag ttc gtg acc gcc gcc ggg atc act ctc ggc atg gac gag ctg      912
Leu Glu Phe Val Thr Ala Ala Gly Ile Thr Leu Gly Met Asp Glu Leu
290                 295                 300 tac aag taa                                                           921
Tyr Lys
305

<210> SEQ ID NO 59
<211> LENGTH: 306
<212> TYPE: PRT
<213> ORGANISM: Artificial Sequence
<220> FEATURE:
<223> OTHER INFORMATION: Drosophila melanogaster polypeptide-EGFP fusion
      protein

<400> SEQUENCE: 59

Met Cys Arg His Ser Ser Leu Ser Leu Ser Leu Ser Leu Ser
1               5                   10                  15

Val Ser Leu Cys Phe Arg Leu Ser Leu Val Tyr Val Leu Asn Gly Gln
            20                  25                  30

Val His Lys Lys Arg Val Tyr Ala Ile Ser Gln Phe Ala Ala Asn Asn
        35                  40                  45

Asn Lys Ala Gly Ile Gly Ile Ser Leu Ser Glu Glu Arg Asp Pro Pro
    50                  55                  60
```

```
Val Ala Thr Met Val Ser Lys Gly Glu Glu Leu Phe Thr Gly Val Val
65                  70                  75                  80

Pro Ile Leu Val Glu Leu Asp Gly Asp Val Asn Gly His Lys Phe Ser
                85                  90                  95

Val Ser Gly Glu Gly Glu Gly Asp Ala Thr Tyr Gly Lys Leu Thr Leu
            100                 105                 110

Lys Phe Ile Cys Thr Thr Gly Lys Leu Pro Val Pro Trp Pro Thr Leu
            115                 120                 125

Val Thr Thr Leu Thr Tyr Gly Val Gln Cys Phe Ser Arg Tyr Pro Asp
    130                 135                 140

His Met Lys Gln His Asp Phe Phe Lys Ser Ala Met Pro Glu Gly Tyr
145                 150                 155                 160

Val Gln Glu Arg Thr Ile Phe Phe Lys Asp Asp Gly Asn Tyr Lys Thr
                165                 170                 175

Arg Ala Glu Val Lys Phe Glu Gly Asp Thr Leu Val Asn Arg Ile Glu
            180                 185                 190

Leu Lys Gly Ile Asp Phe Lys Glu Asp Gly Asn Ile Leu Gly His Lys
        195                 200                 205

Leu Glu Tyr Asn Tyr Asn Ser His Asn Val Tyr Ile Met Ala Asp Lys
    210                 215                 220

Gln Lys Asn Gly Ile Lys Val Asn Phe Lys Ile Arg His Asn Ile Glu
225                 230                 235                 240

Asp Gly Ser Val Gln Leu Ala Asp His Tyr Gln Gln Asn Thr Pro Ile
            245                 250                 255

Gly Asp Gly Pro Val Leu Leu Pro Asp Asn His Tyr Leu Ser Thr Gln
            260                 265                 270

Ser Ala Leu Ser Lys Asp Pro Asn Glu Lys Arg Asp His Met Val Leu
        275                 280                 285

Leu Glu Phe Val Thr Ala Ala Gly Ile Thr Leu Gly Met Asp Glu Leu
    290                 295                 300

Tyr Lys
305
```